(12) United States Patent
Jain

(10) Patent No.: US 11,869,673 B1
(45) Date of Patent: Jan. 9, 2024

(54) ELECTRONIC HEALTH RECORD PLATFORM

(71) Applicant: DOCEREE INC., Parsippany, NJ (US)

(72) Inventor: Harshit Jain, Parsippany, NJ (US)

(73) Assignee: DOCEREE INC., Parsippany, NJ (US)

( * ) Notice: Subject to any disclaimer, the term of this patent is extended or adjusted under 35 U.S.C. 154(b) by 0 days.

(21) Appl. No.: 18/116,290

(22) Filed: Mar. 1, 2023

Related U.S. Application Data

(63) Continuation-in-part of application No. 17/857,013, filed on Jul. 3, 2022.

(51) Int. Cl.
| | |
|---|---|
| *G16H 50/20* | (2018.01) |
| *G16H 20/30* | (2018.01) |
| *G16H 70/20* | (2018.01) |
| *G16H 10/60* | (2018.01) |
| *G16H 40/20* | (2018.01) |

(52) U.S. Cl.
CPC ............. *G16H 70/20* (2018.01); *G16H 10/60* (2018.01); *G16H 40/20* (2018.01)

(58) Field of Classification Search
CPC ......... G16H 70/20; G16H 10/60; G16H 40/20
See application file for complete search history.

(56) References Cited

U.S. PATENT DOCUMENTS

| | | | |
|---|---|---|---|
| 2012/0101847 A1* | 4/2012 | Johnson ................. | G16H 10/60 705/2 |
| 2020/0411186 A1* | 12/2020 | Blanchard ............ | A61B 5/4836 |
| 2022/0051276 A1* | 2/2022 | Zelocchi ................ | G16H 30/40 |

\* cited by examiner

*Primary Examiner* — Maroun P Kanaan
(74) *Attorney, Agent, or Firm* — Edmond DeFrank

(57) ABSTRACT

The embodiments disclose a medical product processing system including a first graphical user interface (GUI) coupled to an EHR platform and configured to display to a medical provider (MP) predefined conditions of a patient of the MP, a database with records stored therein containing predefined information relating to medical products related to the predefined conditions, a second GUI coupled to the database and configured to display to a medical product provider (MPP) adjustable condition trigger (CT) settings, wherein the adjustable CT settings are configurable by the MPP to associate a predefined condition with related predefined information, a processor coupled to the database, the first GUI and the second GUI, and wherein when the first GUI displays at least one condition to the MP, the processor automatically sends related predefined information from the database to be displayed on the first GUI based on the adjustable CT setting configured by the MPP.

20 Claims, 54 Drawing Sheets

FIG. 27

ELECTRONIC HEALTH RECORD PLATFORM

BACKGROUND

Physicians can deliver better care with relevant information but lack timely access. Healthcare is experiencing a significant digital transformation. But even with all the digitalization, healthcare providers do not have access to up-to-date, high-quality medical information that is only available from life sciences organizations. Research has proven that a healthcare provider's access to quality medical information can lead to optimal treatment outcomes.

BRIEF DESCRIPTION OF THE DRAWINGS

Figure 27:
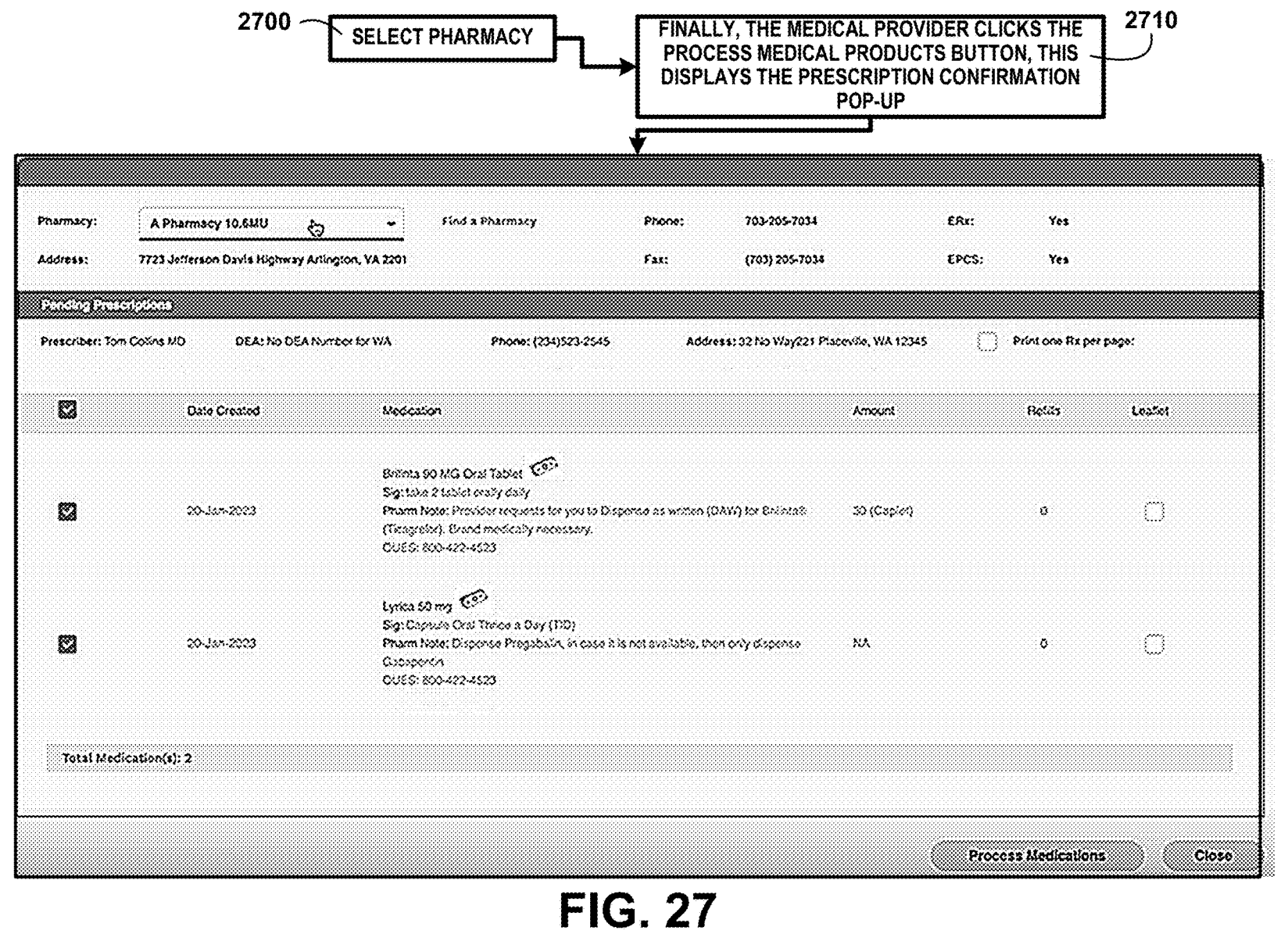

FIG. 27 shows for illustrative purposes only an example of a prescription conversation pop-up of one embodiment.

DETAILED DESCRIPTION OF THE INVENTION

Figure 1:
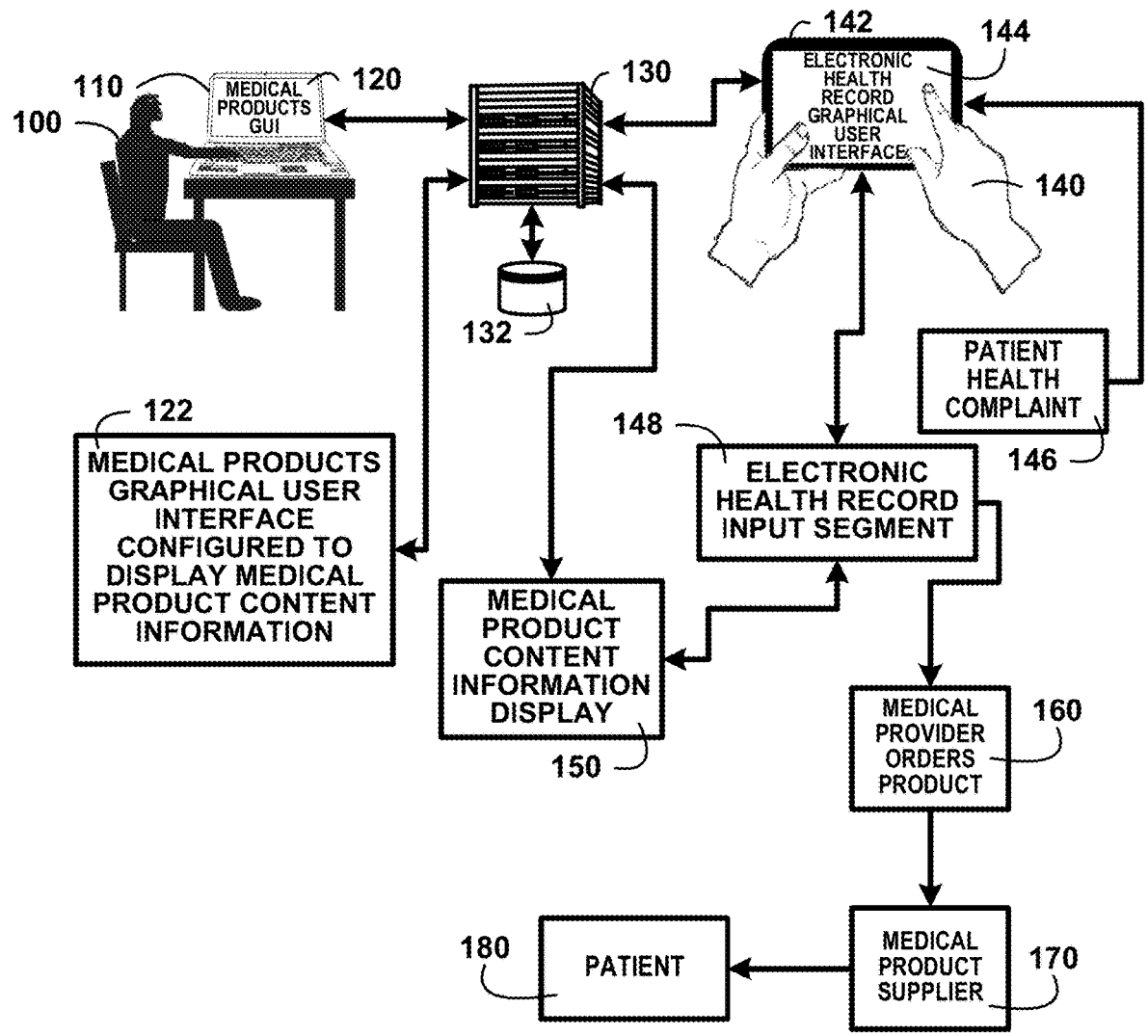
FIG. 1 shows a block diagram of an overview flow chart presenting predefined information of one embodiment.

In the following description, reference is made to the accompanying drawings, which form a part hereof, and which are shown by way of illustration a specific example in which the invention may be practiced. It is to be understood that other embodiments may be utilized, and structural changes may be made without departing from the scope of the present invention.
General Overview It should be noted that the descriptions that follow, for example, in terms of electronic medical record advertising platform method and devices are described for illustrative purposes and the underlying system can apply to any number and multiple types of Clinical triggers. In one embodiment of the present invention, the electronic medical record advertising platform method and devices can be configured using electronic health records. The electronic medical record advertising platform method and devices can be configured to include clinical alerts integrated into the electronic health records and can be configured to include disease awareness messaging integrated into the electronic health records using the present invention. Wherein Clinical triggers are defined as a specific event or condition that causes a particular outcome. The term "HVA" used herein and the term "National Provider Identifier" are used interchangeably without any change in meaning.

SUMMARY OF THE INVENTION

The electronic health record platform includes a medical product processing system using a first graphical user interface coupled to an electronic health record (EHR) platform to display to a medical provider predefined conditions of a patient of the medical provider. The patient's predefined conditions are entered into the patient's electronic health record during the interaction between the patient and the medical provider. The predefined conditions include definitions of the international classification of diseases (ICD) codes.

A database with plural records stored therein containing predefined information relating to plural medical products related to the predefined conditions. The predefined conditions are clinical triggers used to determine related predefined information to display the predefined information to the medical provider with the first graphical user interface. The database stored predefined information may include public service predefined information regarding drugs and medications and disease awareness, medical provider and patient educational materials, condition medical trial results, medical products potential benefits for a patient's conditions, side effects, marketing materials, availability, advertisements, graphical images, patient affordability information, and pricing, discounts, coupons, and copays.

A second graphical user interface is coupled to the database to display to a medical product provider adjustable condition trigger settings, wherein the adjustable condition trigger settings are configurable by the medical product provider to associate at least one predefined condition with related predefined information. A medical product provider may be a medical product supplier, distributor, advertiser, pharmaceutical company, and other entity providing predefined information targeted to the patient's predefined condition.

A processor coupled to the database, the first graphical user interface, and the second graphical user interface analyses the relationship between predefined conditions and predefined information stored in the database. The first graphical user interface displays at least one condition to the medical provider, the processor automatically sends the related predefined information from the database to be displayed on the first graphical user interface based on the adjustable clinical trigger setting selected by the medical product provider.

The presentation of predefined information is displayed to a medical provider using a first graphical user interface (GUI) on a point-of-care (POC) platform during the medical provider's interaction with the patient. The timely delivery of the predefined information related to the patient's predefined condition, for example, maybe a medication treatment for the patient's predefined condition of one embodiment FIG. 1 shows a block diagram of an overview flow chart presenting predefined information of one embodiment. FIG. 1 shows a medical products provider 100 using a medical products GUI (graphical user interface) 120 of a medical products provider computer 110. The medical products graphical user interface is configured to display medical product content information 122 on electronic health records medical provider and patient interaction segment screens during an appointment. The medical products GUI (graphical user interface) 120 stores the medical product content information and graphical displays on network platform databases and memory devices 132 coupled to network platform servers, communication devices, processors, graphic devices, and other digital devices 130. The medical provider 140 uses a medical provider mobile device 142 with an electronic health record graphical user interface 144 to input a patient health complaint 146. The medical provider 140 inputs the patient health complaint 146 and other conditions in an electronic health record input segment 148. The electronic health record input segment 148 is shown on the medical provider's mobile device 142. The patient health complaint 146 is transmitted to the network platform databases and memory devices 132. The patient health complaint 146 triggers a medical product content information display 150 in the electronic health record input segment 148 screen from the network platform databases and memory devices 132. The electronic health record graphical user interface 144 displays of the medical product content information including detailed information regarding the medical product. The medical provider 140 may use the medical product content information display 150 to prepare medical provider orders for product 160 and transmit the order to a medical product supplier 170 for example a pharmacy. The patient 180 can then pick up the order of the medical product from the medical product supplier 170 of one embodiment.

Clinical triggers based on a medical provider 140 point-of-care (POC) electronic workflow and patient real-time interaction discussed patient health complaint 130. The medical products provider's 100 pool of medical product content information associated with predefined clinical triggers including international classification of diseases (ICD) codes. A mapping device coupled to the database 132 is configured to correlate medical product content information to the predefined clinical triggers including international classification of diseases codes. Integrating the clinical triggers mapped medical product content information into POC platform segments.

Displaying mapped medical product content information into POC screens based on the medical provider 140 electronic health record graphical user interface 144 inputs during the patient real-time interaction. Facilitating medical provider 140 E-prescribing of clinical triggered medical products provider's 100 medical products. Displaying clinical trigger-based medical product content information displayed through the electronic health record graphical user interface 150 provides timely delivery of pertinent information to at least one targeted medical provider 140.

At least one predefined clinical trigger is configured to activate based on a patient health complaint 146 and medical provider 140 patient real-time interaction. A plurality of medical product content information is associated with predefined clinical triggers predefined to activate upon receipt of point-of-care data related to advertisements mapped to integrated business rules workflows. A mapping device coupled to the at least one predefined clinical trigger configured to correlate an advertiser's pool of advertisements to the predefined clinical triggers including international classification of diseases codes.

A platform integration device coupled to the mapping device configured to integrate the clinical triggers mapped advertiser's pool of advertisements into at least one point-of-care platform. An interactive electronic display device integrated into at least one point-of-care platform configured to display the mapped advertiser's pool of advertisements into point-of-care screens based on clinical triggers and when tapped further displays data regarding the properties of the advertised product or service. An electronic prescription interface integrated into the at least one point-of-care platform configured to provide the health care professional with point-of-care E-prescribing of clinical triggered advertiser's medications.

An advertising point-of-care integration network configured to display medical advertising and data related to a specialty of a health care professional during the health care professional's point-of-care electronic workflow and patient real-time interaction. A multi-platform conversion device coupled to the integration network configured to integrate advertising point-of-care integration network clinical triggers and services across multiple point-of-care platforms of one embodiment.

DETAILED DESCRIPTION

Figure 2:
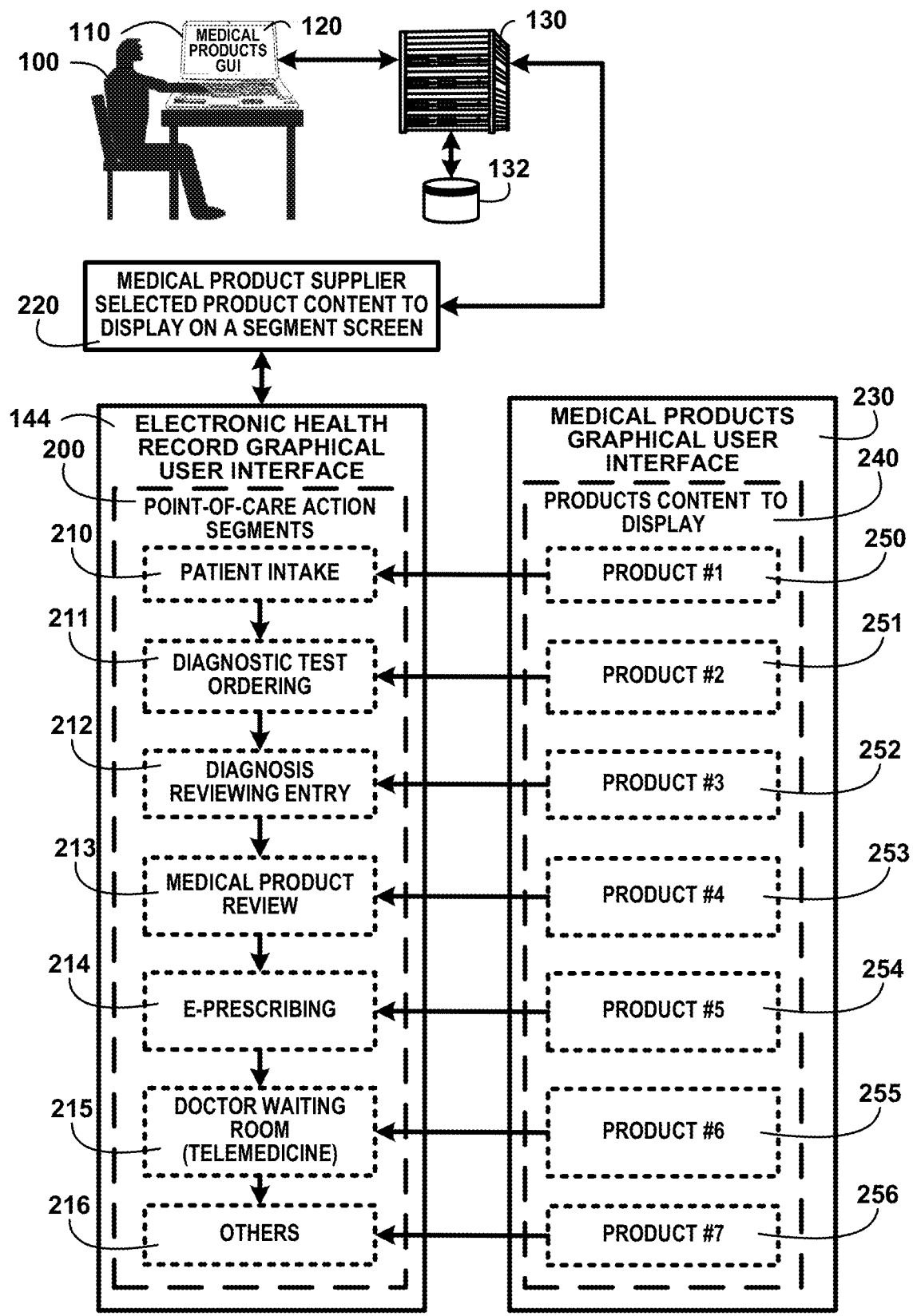
FIG. 2 shows a block diagram of an overview of presenting predefined information of one embodiment.

FIG. 2 shows a block diagram of an overview of presenting predefined information of one embodiment. FIG. 2 shows a medical products provider 100 using a medical products GUI (graphical user interface) 120 of a medical products provider computer 110. The medical products graphical user interface is configured to display medical product content information 122 on electronic health records medical provider and patient interaction segment screens during an appointment. The medical products GUI (graphical user interface) 120 stores the medical product content information and graphical displays on network platform databases and memory devices 132 coupled to network platform servers, communication devices, processors, graphic devices, and other digital devices 130.

FIG. 2 also shows a medical product supplier selected product content to display on a segment screen 220. The medical product supplier 170 of FIG. 1 stores the selected product content to display in the database 120. A medical products graphical user interface 230 is used by the medical product supplier 170 of FIG. 1 to prepare the product's content to display 240. The medical product supplier 170 of FIG. 1 associates the selected product content to display with electronic health record graphical user interface 150 point-of-care action segments 200.

In one embodiment the medical product supplier 170 of FIG. 1 associates product #1 250 with the patient intake 210 segment to display on this screen. Another association is made for product #2 251 for the diagnostic test ordering 211 segment to display on this screen. Product #3 252 is associated with the diagnosis reviewing entry 212 segment to display on this screen. Product #4 253 is associated with the medical product review 213 segment to display on this screen. An association is made for product #5 254 on the e-prescribing 214 segment to display on this screen. Product #6 255 is associated with the doctor waiting room (telemedicine) 215 segment to display on this screen. Product #7 256 is associated with others 216 segment to display on this screen of one embodiment.

Clinical triggers are mapped to segments of a point-of-care platform health care professional's workflow including health care professional (HCP) login, patient intake, diagnostic test, diagnosis review, medication review, E-prescribing, and other applicable segments. Clinical triggers are mapped to patient demographics (age and gender), patient's coverage profile, and clinical indicators of a patient (temperature, blood pressure, pulse, respiration, etc.). The prescribing behavior of an HCP, which includes: lab tests ordered (HCPCs), the diagnosis (ICD10), the prescription (NDC), and the pharmacy (NCPDP) recommended, also determines additional events that activate clinical triggers during a caregiving session.

The clinical workflow may vary from one POC platform to another, either in sequence or several overall segments, nevertheless, these clinical triggers are flexible and robust enough to be mapped to and meet these variable requirements. Once a specific clinical trigger is activated (a configured business rule is met), on a POC platform during the ongoing HCP and patient interaction, the most applicable advertisement related to a medical brand is delivered to the targeted HCP enabling the HCP, to view the advertisement, and take appropriate action. All this happens in real time and displayed advertisements change with the selection of the corresponding trigger parameter selection on the POC platform of one embodiment. The descriptions continue in FIG. 3.

Figure 3:
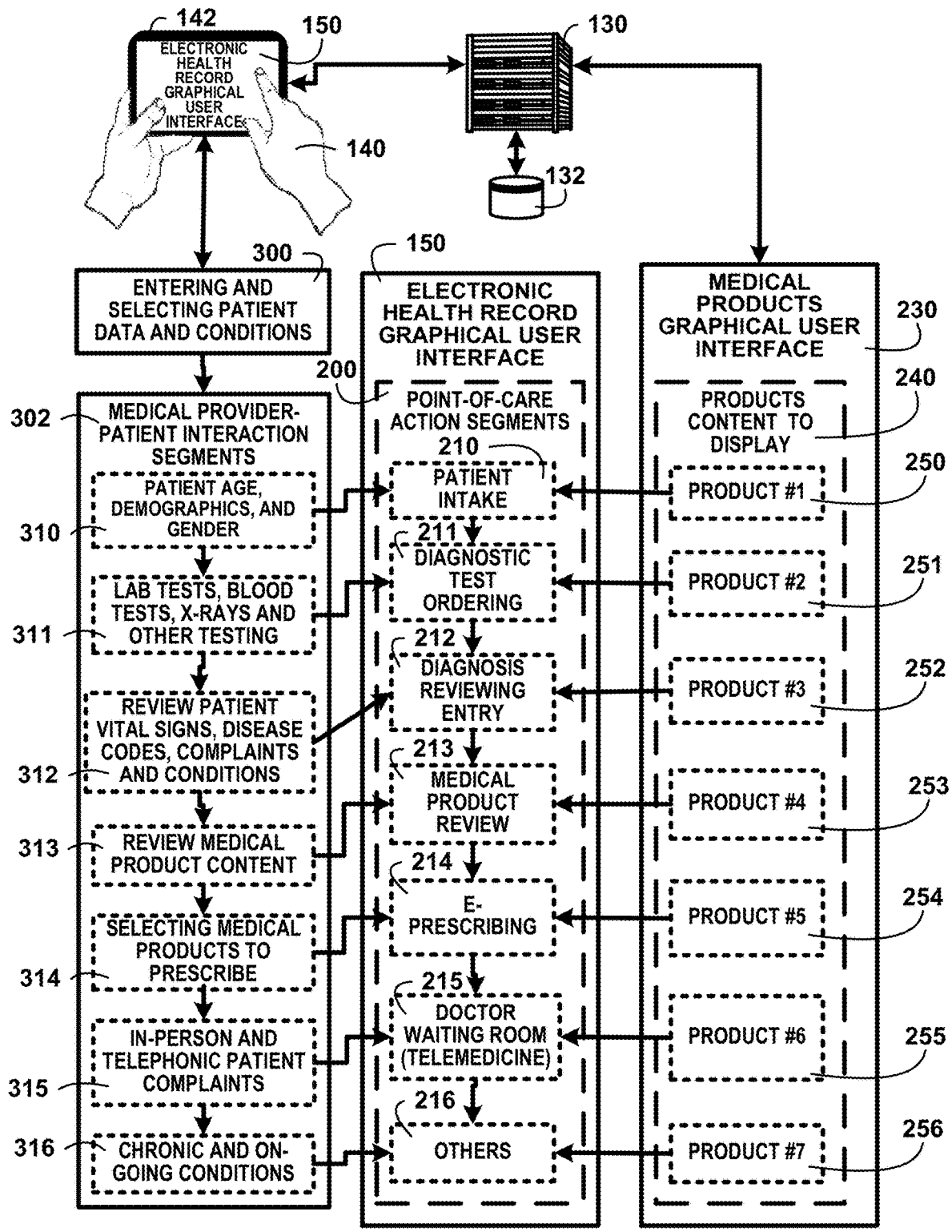
FIG. 3 shows a block diagram of an overview of presenting predefined information of medical products of one embodiment.

Presenting Predefined Information about Medical Products:

FIG. 3 shows a block diagram of an overview of presenting predefined information of medical products of one embodiment. FIG. 3 shows a continuation from FIG. 2. FIG. 3 shows the medical provider 140 uses a medical provider mobile device 142 with an electronic health record graphical user interface 144 to input a patient health complaint 146 of FIG. 1. The medical provider 140 inputs the patient health complaint 146 and other conditions in an electronic health record input segment 148 of FIG. 1. The electronic health record input segment 148 is shown on the medical provider mobile device 142. The patient health complaint 146 of FIG. 1 is transmitted to the network platform databases and memory devices 132. The patient health complaint 146 of FIG. 1 triggers a medical product content information display 150 in the electronic health record input segment 148 of FIG. 1 screen from the network platform databases and memory devices 132.

The medical products provider 100 of FIG. 1 using a medical products GUI (graphical user interface) 120 of FIG.

1 of a medical products provider computer 110 of FIG. 1 stored the medical product content information and graphical displays on network platform databases and memory devices 132 coupled to network platform servers, communication devices, processors, graphic devices and other digital devices 130.

The medical products GUI (graphical user interface) 120 stores the medical product content information and graphical displays on network platform databases and memory devices 132 coupled to network platform servers, communication devices, processors, graphic devices, and other digital devices 130.

The medical provider 140 is entering and selecting patient data and conditions 300 during a medical provider-patient interaction 302. In one embodiment, for example, the medical provider enters a patient's age, demographics, and gender 310 into the patient intake 210 screen. Upon entering the patient data the product #1 250 is displayed on the screen. The medical provider 140 is able to review the product #1 250 content associations with the patient's intake data.

The medical provider 140 continues with subsequent segments filling in patient conditions and clinical information and upon entering and selecting drop-down entries is further able to review other product content as they are displayed. The following are other examples of medical product content displays. The medical provider 140 selects from a drop-down list lab tests, blood tests, x-rays, and other testing 311 of the diagnostic test ordering 211 segment, and product #2 251 is displayed for review. The medical provider 140 proceeds to review patient vital signs, disease codes, complaints, and conditions 312 on the diagnosis reviewing entry 212 segment and product #3 252 is displayed with the associations of the for example disease codes.

A review of medical product content 313 by the medical provider 140 in the medical product review 213 segment provides a review of product #4 253 content for the medical provider to review. The medical provider 140 continues with selecting medical products to prescribe 314 in the e-prescribing 214 segment and displayed is product #5 254. The medical provider 140 may click on product #5 254 to review and use the content information to prepare a prescription and order product #5 254 from a pharmacy for the patient to pick up. The medical provider 140 continues with in-person and telephonic patient complaints 315 in the doctor waiting room (telemedicine) 215 segment and product #6 255 is displayed. Chronic and ongoing conditions 316 of a patient are also reviewed in the others 216 segment and product #7 256 is displayed that provides content related to the specific chronic conditions.

The benefits, of these triggers, for medical brands, include the delivery of precise brand messages to HCPs around a specific drug or therapy at a specific moment of an ongoing care delivery process. Either at the time of patient intake, at the time of diagnosis, recommending a medical procedure, or at the time of writing a prescription. Clinical triggers provide medical brands to hyper-target HCPs at the time when they are most receptive to brand messages during an ongoing caregiving procedure. This enables HCPs to receive critical clinical information in real-time and make informed treatment-related decisions for enhanced patient management.

The medical products provider 100 of FIG. 1 may analyze interest and responses to the displayed product content based on medical provider 140 segment display activity. For example, how often is displayed product content followed by being prescribed during the e-prescribing 214 segment? Medical brands can leverage this mechanism to monitor new drug launches, review HCP prescription behavior, decide upon formulary availability of specific medications, determine the pricing of new drugs, get inputs regarding the expansion of their brand products, and above all reap a higher return on investment (ROI) for their brand campaigns of one embodiment.

Figure 4:
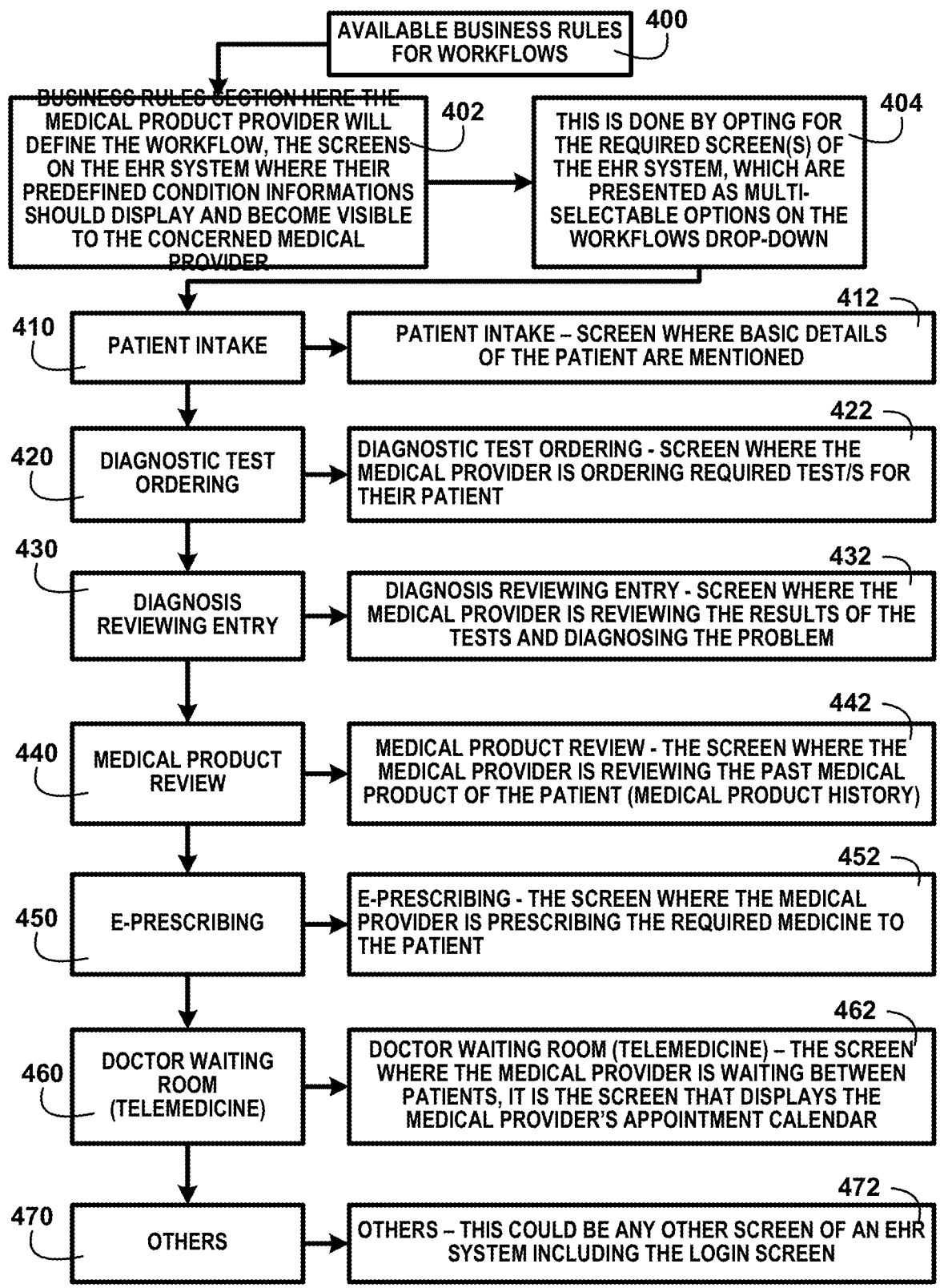
FIG. 4 shows a block diagram of an overview of business rules for workflows of one embodiment.

Business Rules for Workflows:

FIG. 4 shows a block diagram of an overview of business rules for workflows of one embodiment. FIG. 4 shows available business rules for workflows 400. Business rules section here the advertiser will define the workflow, and the screens on the EHR system where their ads should display and become visible to the concerned physician 402. This is done by opting for the required screen(s) of the EHR system, which is presented as multi-selectable options on the workflows drop-down 404. Patient intake 410. Patient intake screen where basic details of the patient are mentioned 412. Diagnostic test ordering 420. Diagnostic test ordering—screen where the physician is ordering required test/s for their patient 422. Diagnosis reviewing entry 430. Diagnosis reviewing entry—screen where the physician is reviewing the results of the tests and diagnosing the problem 432.

Medication review 440. Medication review—the screen where the physician is reviewing the past medication of the patient (medication history) 442. E-prescribing 450. E-prescribing—the screen where the physician is prescribing the required medicine to the patient 452. The doctor waiting room and telemedicine 460. Doctor waiting room (telemedicine)—the screen where the physician is waiting between patients, it is the screen that displays the physician's appointment calendar 462. Others 470. Others—this could be any other screen of an EHR system including the login screen 472 of one embodiment.

Figure 5:
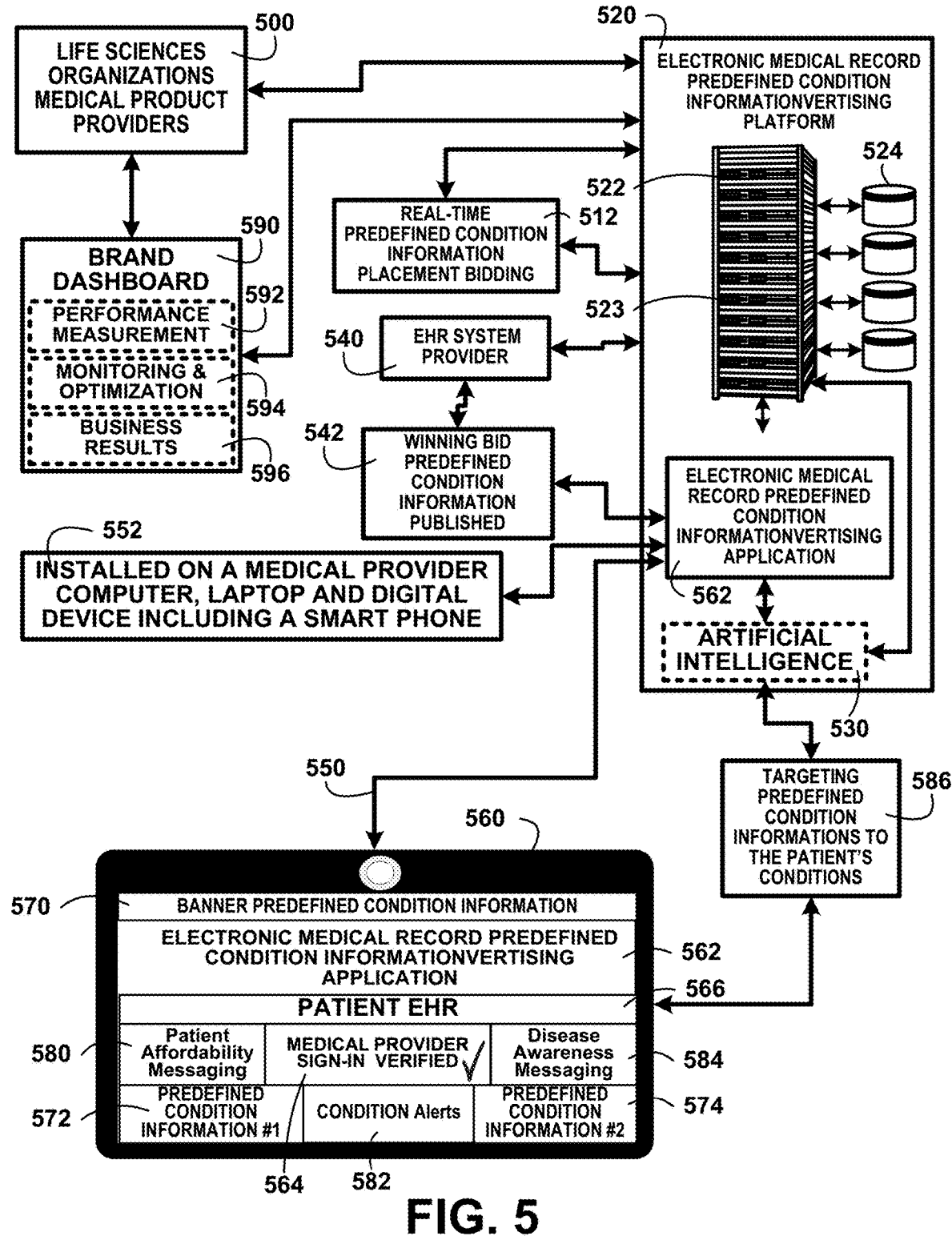
FIG. 5 shows for illustrative purposes only an example of an overview of an electronic medical record advertising platform of one embodiment.

An Electronic Medical Record Advertising Platform:

FIG. 5 shows for illustrative purposes only an example of an overview of an electronic medical record advertising platform of one embodiment. FIG. 5 shows in one embodiment, for example, a life sciences organization advertisers 500 participating in real-time ad placement bidding 512 through an electronic medical record advertising platform 520. The electronic medical record advertising platform 520 comprises a plurality of servers 522, a plurality of processors 523, a plurality of databases 524, a computer having an electronic medical record advertising application 562, and artificial intelligence 530 for analysis of data. In one embodiment, for example, the selection of a winning bid ad published 542 for the EHR system is performed by an electronic health record (EHR) system provider 540 and the electronic medical record advertising platform 520.

In one embodiment, for example, the winning bid ad published 542 is transmitted to the physician 550 with the electronic medical record advertising platform 520. In one embodiment, for example, the winning bid ad published 542 is transmitted with the electronic medical record advertising application 562 to a physician's digital tablet 560, during the physician's workflow with a patient. In one embodiment, for example, the physician sign-in verified 564 to the electronic medical record advertising platform 520 with the electronic medical record advertising application 562 on the physician's digital tablet 560 displays a patient EHR 566. In other embodiments, the electronic medical record advertising application 562 can be installed on a physician's computer, laptop, and digital device including a smartphone 552 allowing the physician to review the patient EHR, Clinical triggers, lab results, disease awareness messaging, patient affordability messaging 580, clinical alerts 582, prescriptions of life sciences organization advertisers 500 products, life science advertiser/supplier product prescription data 674 of FIG. 6 and the e-prescribing of advertiser products.

The EHR system webpages show a banner ad 570 on the top edge and below ads at both corners including ad #1 572 and ad #2 574. The physician can advise the patient on coupons and other cost savings with patient affordability messaging 580 displayed on the physician's digital tablet 560 when tapped by the physician. Tapping the clinical alerts 582 tab provides the physician with up-to-date concerns expressed by life sciences organizations for the physician's diagnosis.

Both the physician and the patient have available disease awareness messaging 584 to be better informed about any new and improved treatments and symptoms of disease mutations and potential side effects of available medications. The life sciences organization advertisers 500 is targeting ads to the patient's conditions 586 to be a relevant source of information and present the latest medications and treatments available for the specific patient's conditions 586.

The electronic medical record advertising platform 520 tracks and records the EHR system webpages ad hits, messaging traffic, and prescriptions of life sciences organization advertisers 500 products. The tracking data is made available to the life sciences organization advertisers 500 on an electronic medical record advertising application 562 brand dashboard 590 to keep the life sciences organization advertisers 500 up to date on a performance measurement 592 for the ads placed, monitoring & optimization 594 of the effectiveness of the ads and the business results 596 of the targeted advertising on the physician EHR system of one embodiment.

Figure 6:
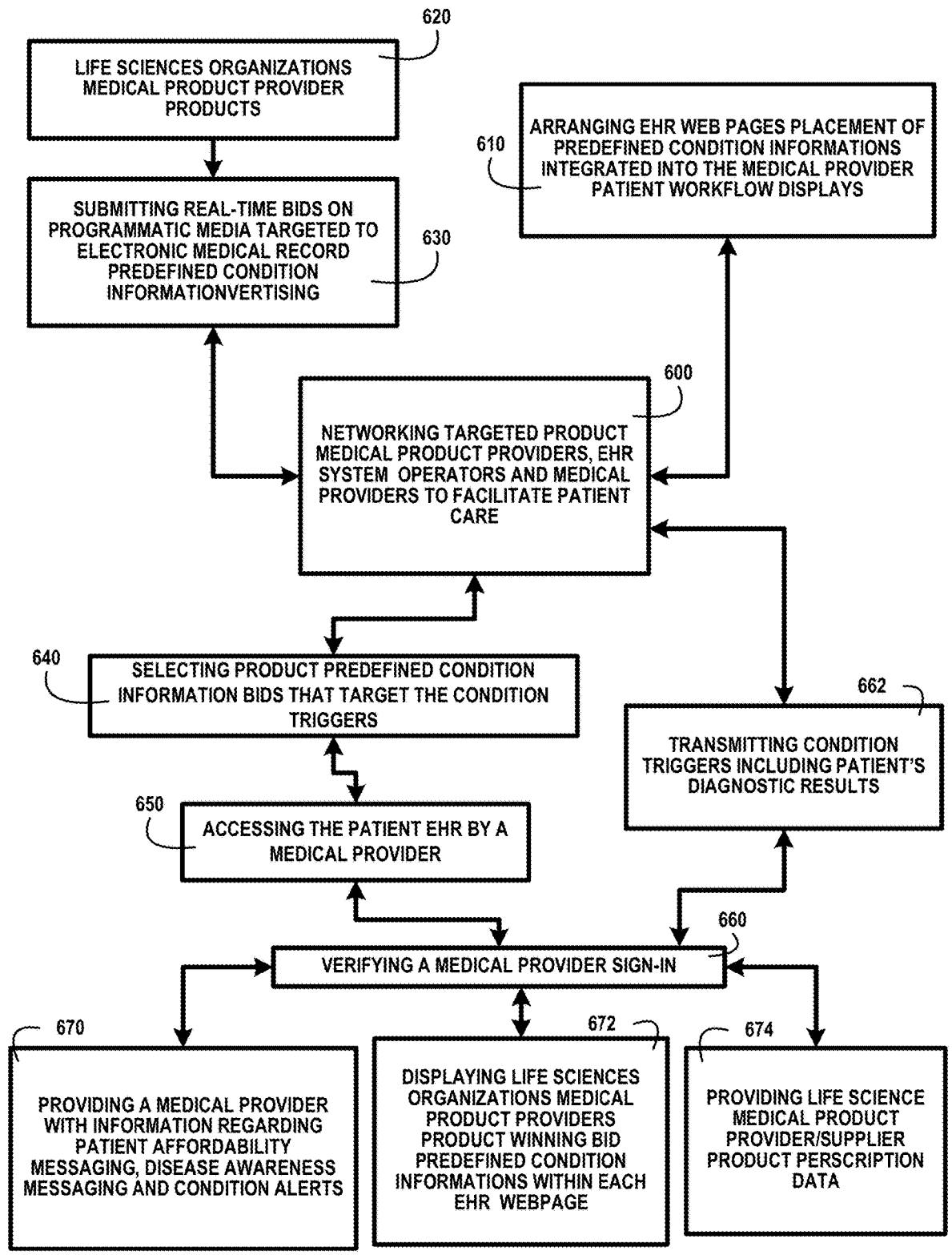
FIG. 6 shows a block diagram of an overview flow chart of targeting life science advertiser/supplier products of one embodiment.

Targeting Life Science Advertiser/Supplier Products:

FIG. 6 shows a block diagram of an overview flow chart of targeting life science advertiser/supplier products of one embodiment. FIG. 6 shows a collaboration of networking targeted product advertisers, EHR system operators, and physicians to facilitate patient care 600 facilitated by the electronic medical record advertising platform 520 of FIG. 5. The electronic medical record advertising platform 520 of FIG. 5 is arranging EHR web pages placement of ads integrated into the physician-patient workflow displays 610. The suppliers' life sciences organizations advertiser products 620 targeted to healthcare providers patient conditions.

The product suppliers are submitting real-time bids on programmatic media targeted to electronic medical record advertising 630. The EHR system providers and electronic medical record advertising platform 520 of FIG. 5 join in selecting product ad bids that target the Clinical triggers 640. The targeted ads are displayed when accessing the patient EHR by a physician 650. EHR system is verifying a physician sign-in 660 and through the electronic medical record advertising platform 520 of FIG. 5 extracting using a data mining processor and transmitting Clinical triggers including patient's diagnostic results 662 and safeguarding privacy in compliance with the Health Insurance Portability and Accountability Act of 1996 (HIPAA).

The displayed information includes integrated targeted ads that provide information on new and effective treatments and additionally are providing a physician with information regarding patient affordability messaging, disease awareness messaging, and clinical alerts 670. Displaying using at least one electronic publishing device the life science advertiser/supplier product winning bid ads within each EHR webpage 672 is also providing accessible life science advertiser/supplier product prescription data 674 the physician can utilize in prescribing medications for the patient of one embodiment.

A Winning Bid Selection Processor

Figure 7:
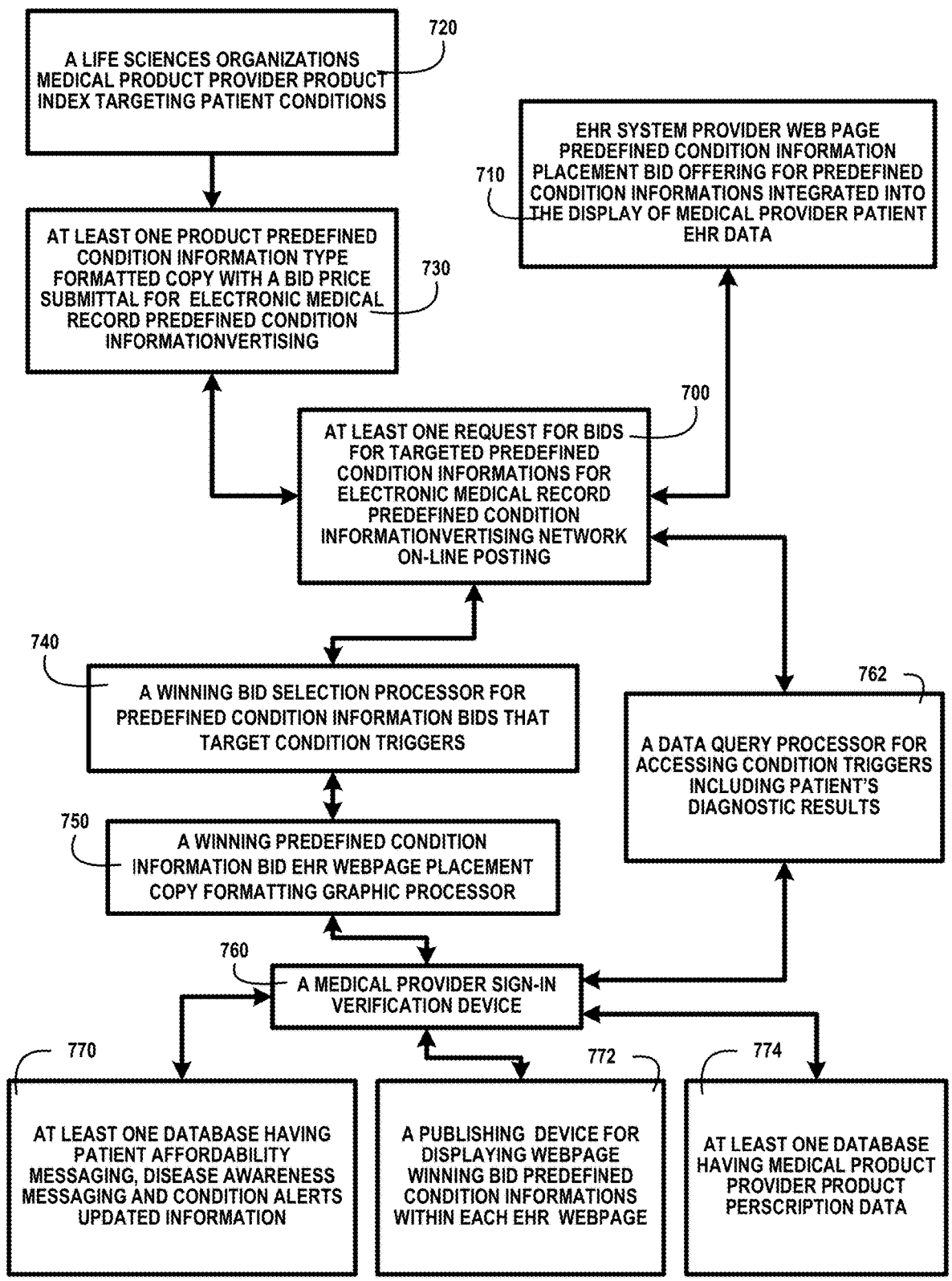
FIG. 7 shows a block diagram of an overview of a winning bid selection processor of one embodiment.

FIG. 7 shows a block diagram of an overview of a winning bid selection processor of one embodiment. FIG. 7 shows at least one request for bids for targeted ads for electronic medical record advertising network online posting 700. The bids are for EHR system provider web page ad placement bid offering for ads integrated into the display of physician-patient EHR data 710. Bidding will be made by a life sciences organizations advertiser product index targeting patient conditions 720.

The life sciences organizations advertiser will submit at least one product ad type formatted copy with a bid price submittal for electronic medical record advertising 730. A winning bid selection processor for ad bids that target Clinical triggers 740 will analyze and also use a winning ad bid EHR webpage placement copy formatting graphic processor 750 for conformity in ad placement size and any reformatting needed to fit the web page layout. A physician sign-in verification device 760 will confirm the physician is licensed and a subscriber to the EHR system.

A data query processor for accessing Clinical triggers including patient's diagnostic results 762 queries the EHR records for Clinical triggers for retrieving at least one database having patient affordability messaging, disease awareness messaging, and clinical alerts updated information 770 and targeted ads for providing the physician with up-to-date information. A publishing device for displaying webpage winning bid ads within each EHR webpage 772 and patient condition messaging including product information from at least one database having advertiser product prescription data 774 of one embodiment.

An Electronic Medical Record Advertising Platform

Figure 8:
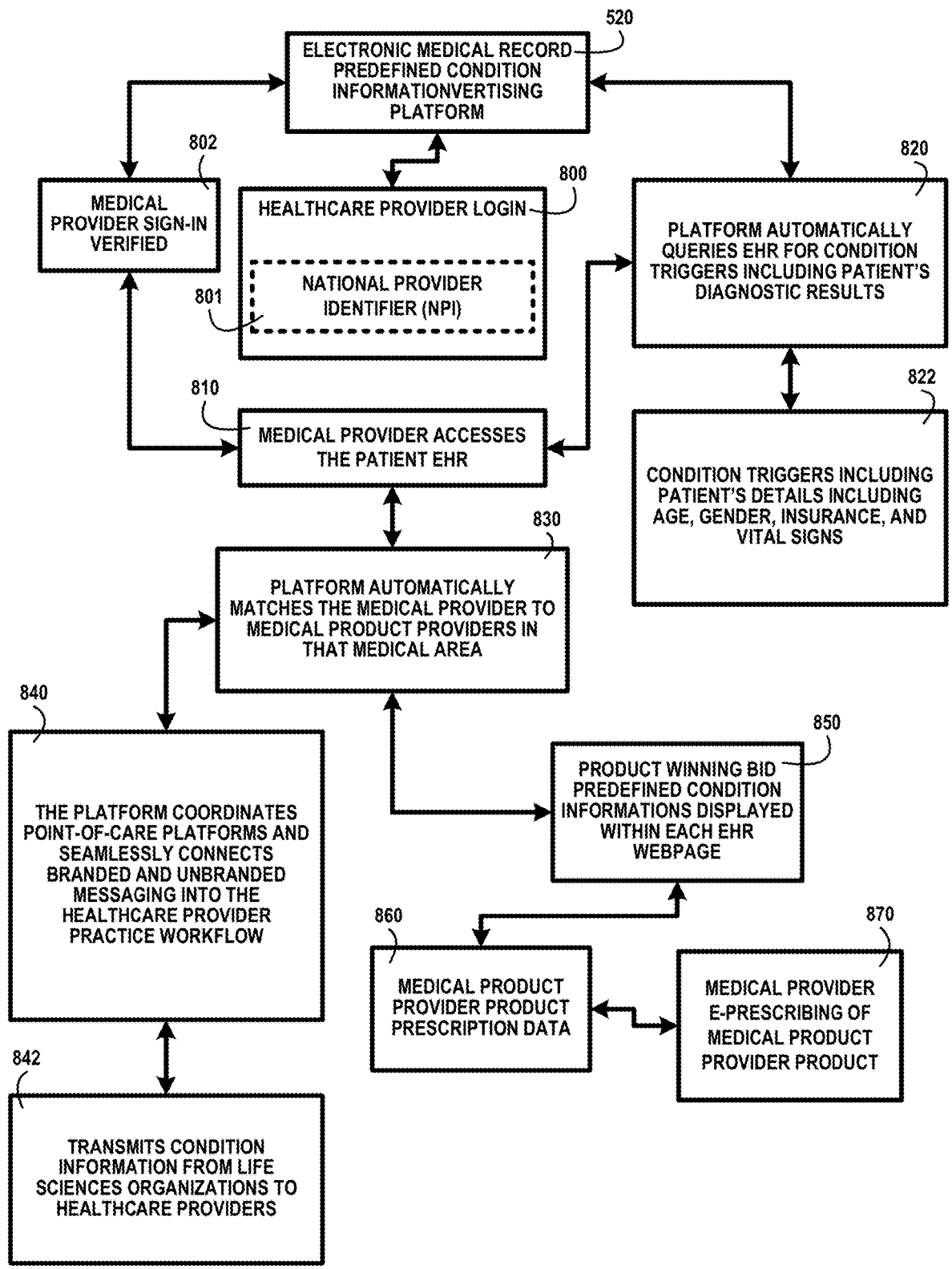
FIG. 8 shows a block diagram of an overview of an electronic medical record advertising platform of one embodiment.

FIG. 8 shows a block diagram of an overview of an electronic medical record advertising platform of one embodiment. FIG. 8 shows electronic medical record advertising POC platforms that integrate an EHR point of care platform with live science organization advertising. A health care provider login 800 includes the national provider identifier 801 (NPI) to allow a physician sign-in to be verified 802 to gain access to the EHR point of care platform. When the physician accesses the patient's EHR 810 the platform automatically queries EHR for Clinical triggers including the patient's diagnostic results 820.

Clinical triggers include patient's details including age, gender, insurance, and vital signs 822. The platform automatically matches the physician to advertisers in that medical area 830 and any specialty. The platform coordinates point-of-care platforms and seamlessly connects branded and unbranded messaging into the healthcare provider practice workflow 840. The platform transmits clinical information from life sciences organizations to health care providers 842. The product winning bid ads displayed within each EHR webpage 850 includes an advertiser product prescription data 860. The advertiser product prescription data 860 aids the physician in e-prescribing of advertiser product 870 of one embodiment.

Figure 9:
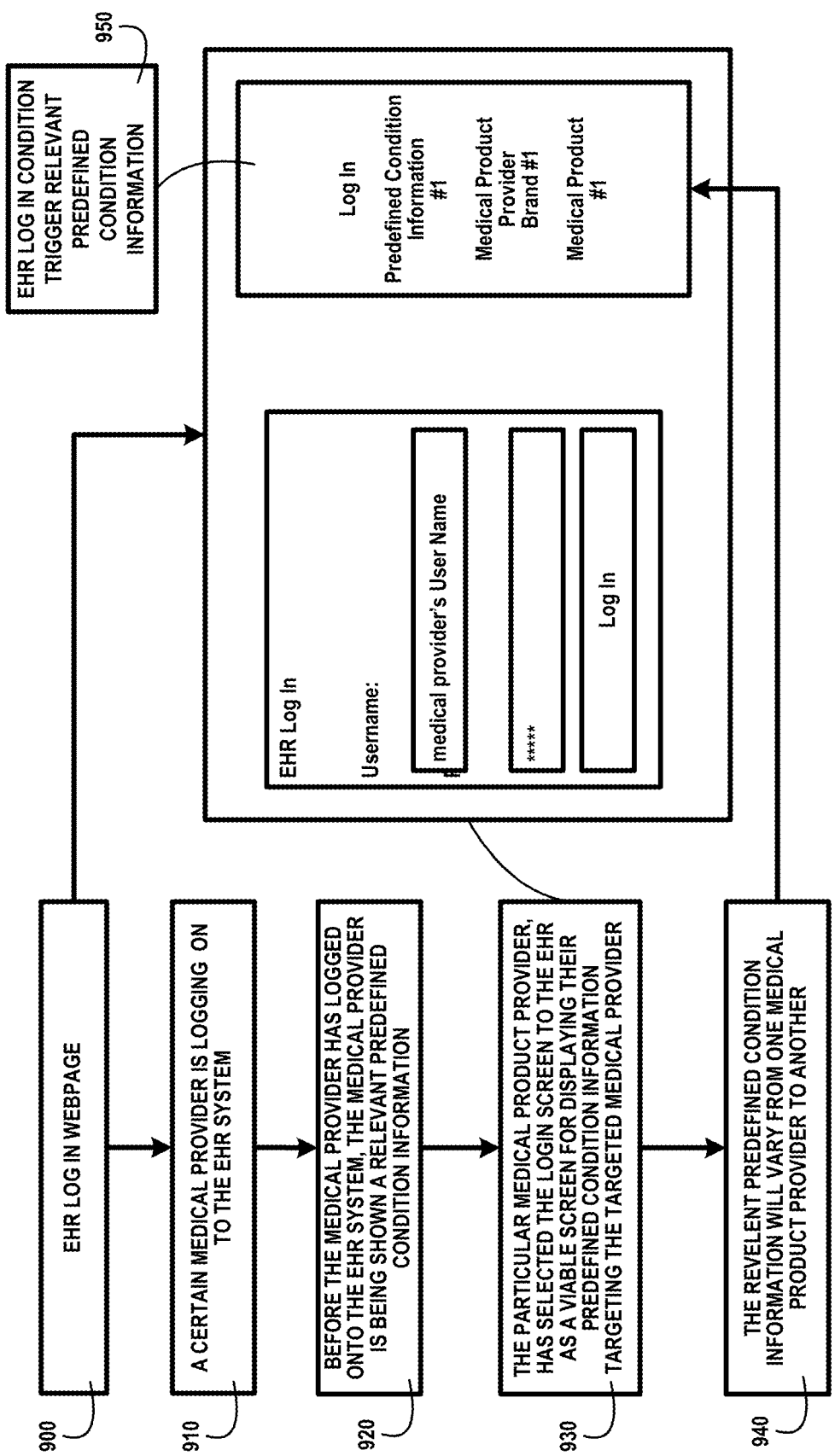
FIG. 9 shows for illustrative purposes only an example of an EHR log-in clinical trigger of one embodiment.

An EHR Log-In Clinical Trigger:

FIG. 9 shows for illustrative purposes only an example of an EHR log-in clinical trigger of one embodiment. FIG. 9 shows an EHR login webpage 900. A certain HCP is logging on to the EHR system 910. Before the HCP has logged onto the EHR system, the HCP is shown a relevant ad 920 on the login screen. The particular advertiser has selected the login screen to the EHR as a viable screen for displaying their ad targeting the targeted physician 930. The relevant ad will vary from one advertiser to another 940. The EHR login clinical trigger relevant ad 950 will also vary with different HCPs specialties of one embodiment.

The EHR login webpage 900 provides entry boxes the certain HCP enters the HCP's User name and Password. The EHR login webpage 900 displays a relevant ad to the right of the EHR Log In area. The relevant ad relates to the specialty of the HCP. Advertisers bid on the placement of ads in the EHR workflow webpages. The certain HCP may see a different ad when logging in depending on how many relevant ads are available for display on the EHR login webpage 900 of one embodiment.

Figure 10:
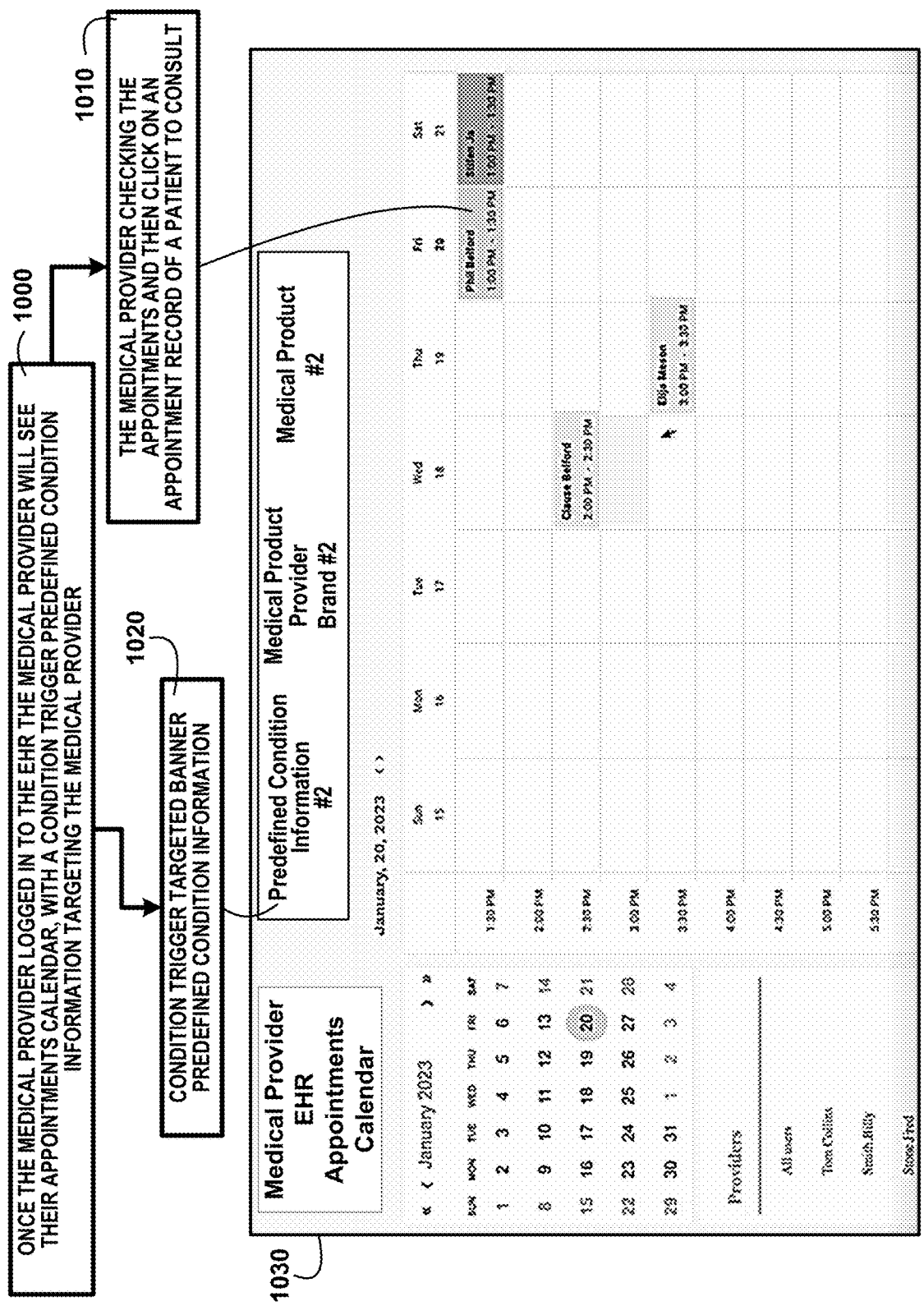
FIG. 10 shows for illustrative purposes only an example of an appointment calendar of one embodiment.

Appointments Calendar:

FIG. 10 shows for illustrative purposes only an example of an appointment calendar of one embodiment. FIG. 10 shows once the physician logs in to the EHR the HCP will see their appointments calendar, with a clinical trigger ad targeting the HCP 1000. The physician checks the appointments and then clicks on an appointment record of a patient to consult 1010. The information for the patient for the scheduled appointment when clicked displays the patient chart. Clinical trigger targeted banner ad 1020 is displayed on the clinical targeted page. The HCP EHR Appointments Calendar 1030 is a clinical target and is linked to the patient chart of one embodiment.

Figure 11:
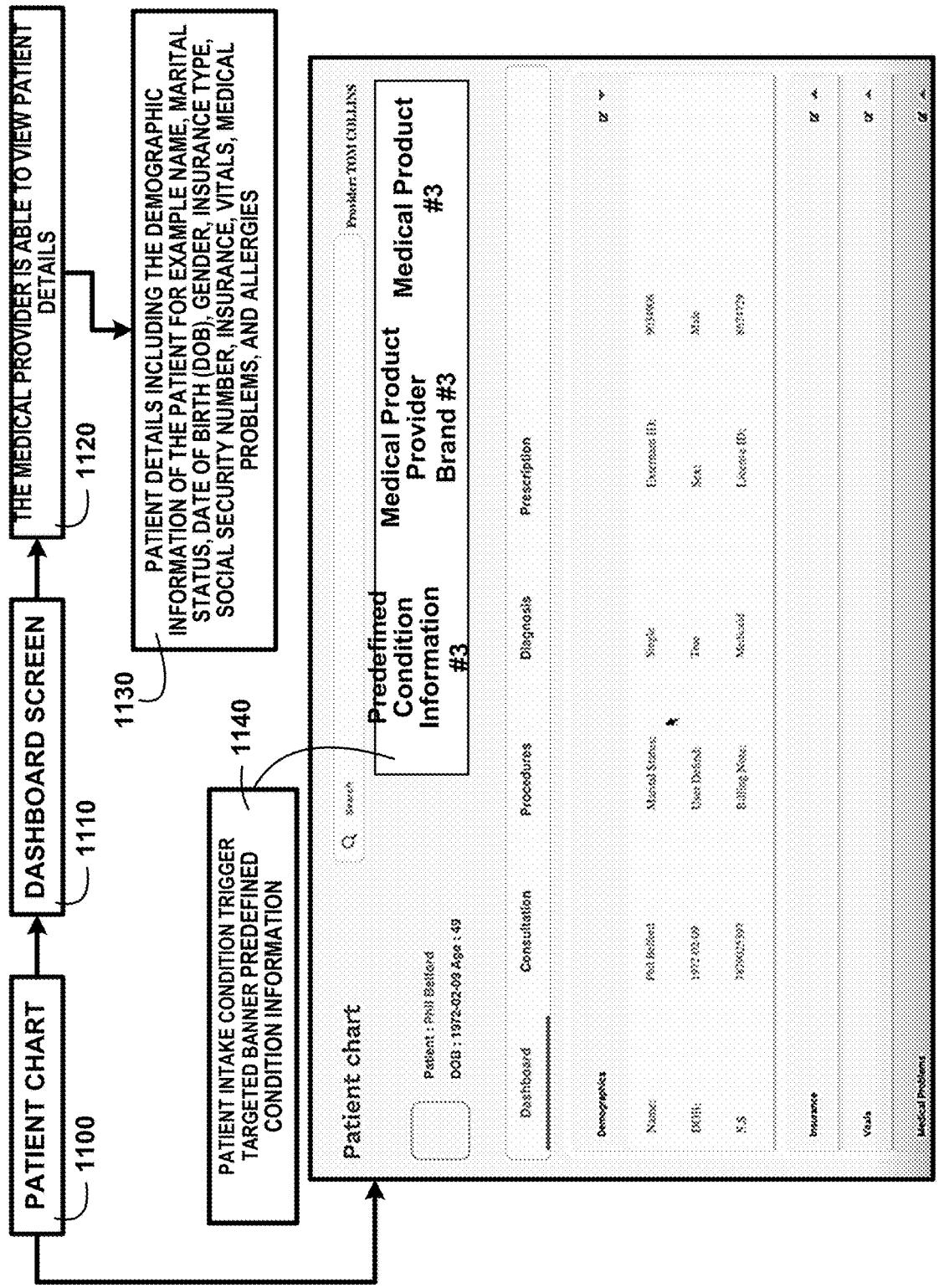
FIG. 11 shows for illustrative purposes only an example of a dashboard screen of one embodiment.

Dashboard Screen:

FIG. 11 shows for illustrative purposes only an example of a dashboard screen of one embodiment. FIG. 11 shows a patient chart 1100 display after the physician clicked the patient appointment. The patient chart 1100 includes a dashboard screen 1110. The dashboard screen 1110 provides tabs for links to the patient EHR so the physician can view patient details 1120. Patient details include the demographic information of the patient for example name, marital status, date of birth (DOB), gender, insurance type, social security number, insurance, vitals, medical problems, and allergies 1130. The physician can see the patient intake clinical trigger targeted banner ad 1140 of one embodiment.

Figure 12:
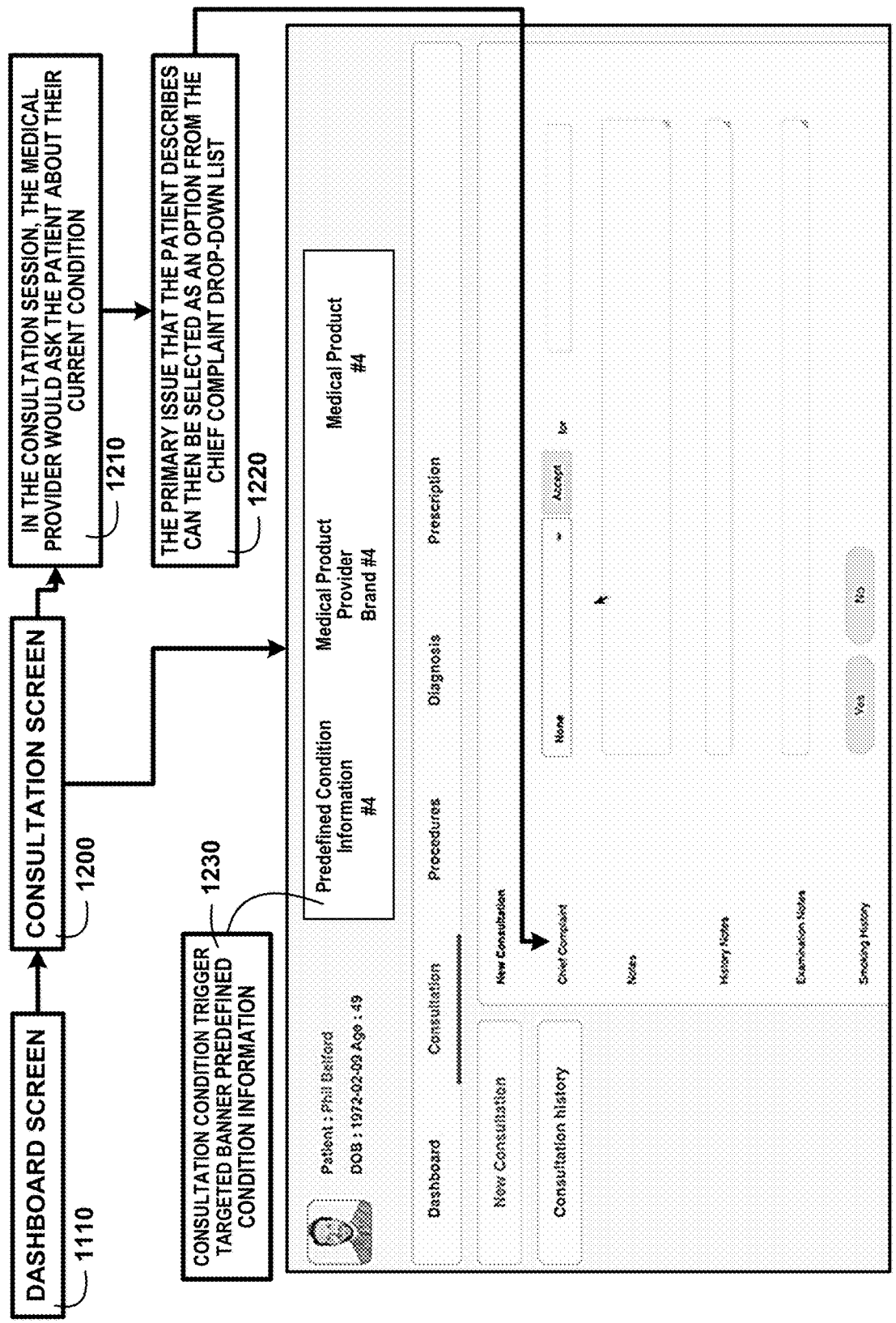
FIG. 12 shows for illustrative purposes only an example of a consultation screen of one embodiment.

Consultation Screen:

FIG. 12 shows for illustrative purposes only an example of a consultation screen of one embodiment. FIG. 12 shows the dashboard screen 1110. The dashboard screen 1110 includes a tab for a consultation screen 1200. In the consultation session, the physician would ask the patient about their current condition 1210. The primary issue that the patient describes can then be selected as an option from the chief complaint drop-down list 1220. The physician can see the consultation clinical trigger targeted banner ad 1230 of one embodiment.

Figure 13:
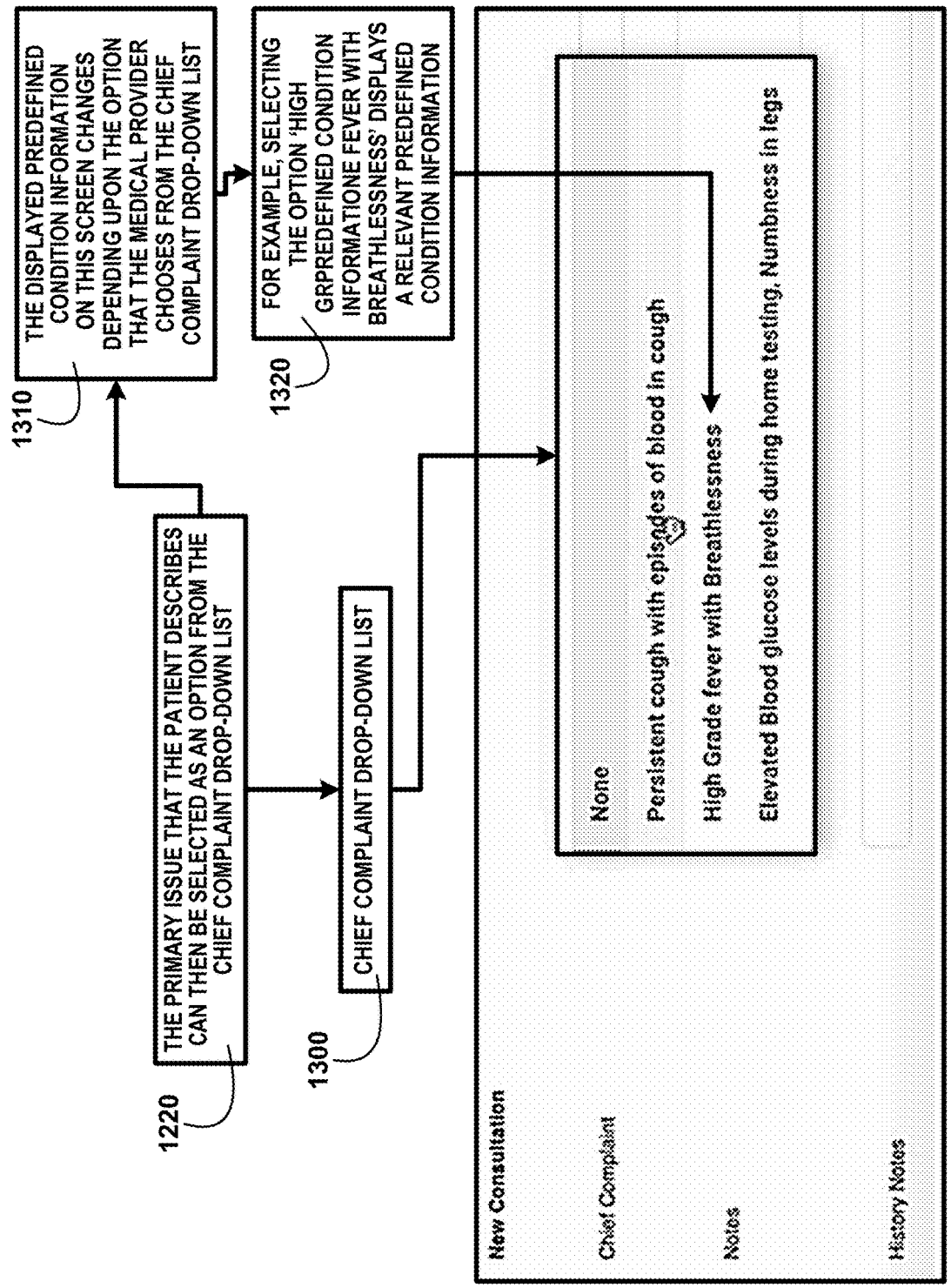
FIG. 13 shows for illustrative purposes only an example of a chief complaint drop-down list of one embodiment.

Chief Complaint Drop-Down List:

FIG. 13 shows for illustrative purposes only an example of a chief complaint drop-down list of one embodiment. FIG. 13 shows the primary issue that the patient describes can then be selected as an option from the chief complaint drop-down list 1220. Chief complaint drop-down list 1300. The displayed ad on this screen changes depending upon the option that the physician chooses from the chief complaint drop-down list 1310. For example, selecting the option 'high grade fever with breathlessness' displays a relevant ad 1320 of one embodiment.

Figure 14:
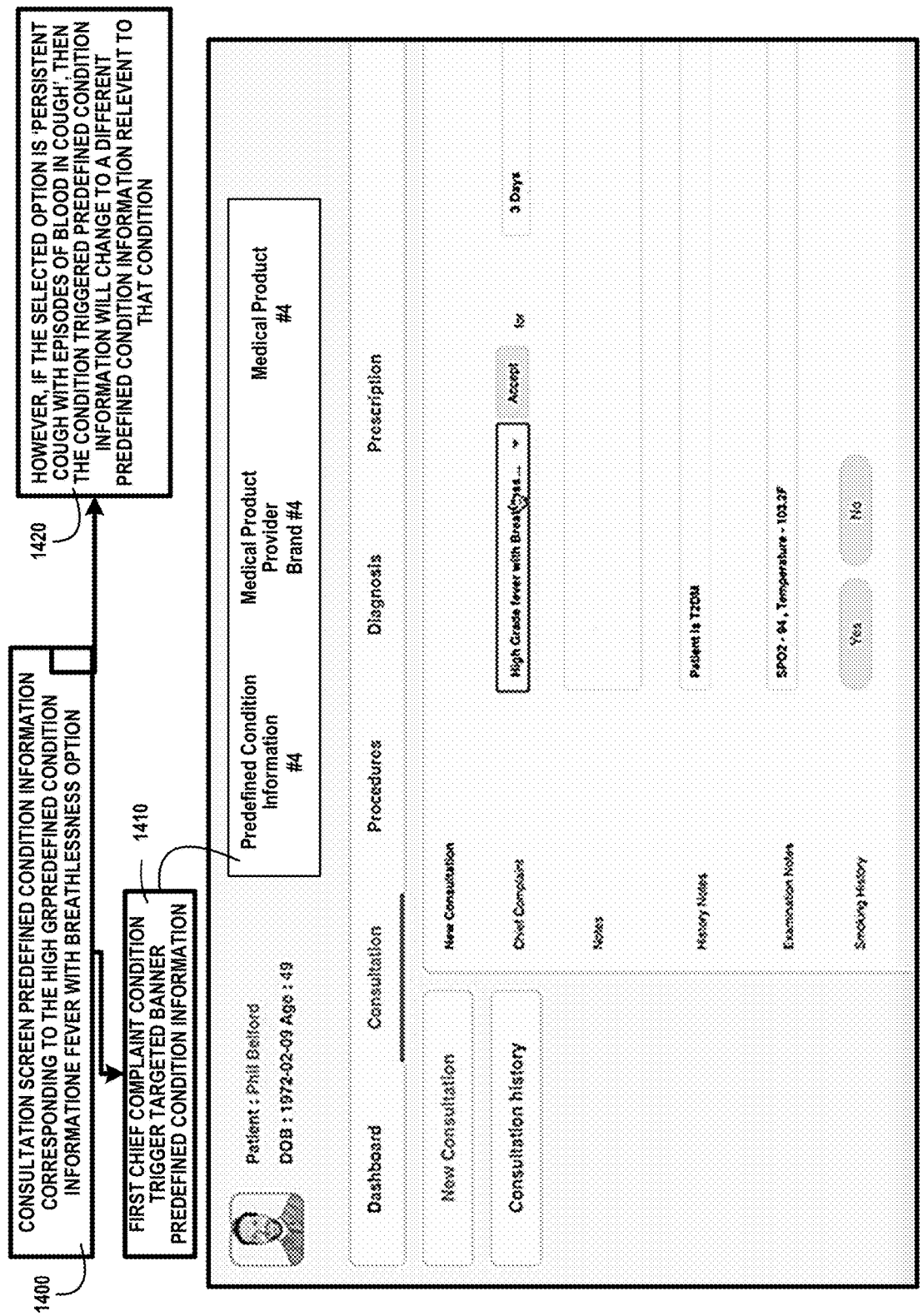
FIG. 14 shows for illustrative purposes only an example of the first chief complaint clinical trigger targeted banner ad of one embodiment.

First Chief Complaint Clinical Trigger Targeted Banner Ad:

FIG. 14 shows for illustrative purposes only an example of the first chief complaint clinical trigger targeted banner ad of one embodiment. FIG. 14 shows a consultation screen ad corresponding to the 'high grade fever with breathlessness' option 1400. The first chief complaint clinical trigger targeted banner ad 1410 is displayed as a clear view for the physician. However, if the selected option is 'persistent cough with episodes of blood in cough', then the clinical triggered ad will change to a different ad relevant to that condition 1420 of one embodiment.

Figure 15:
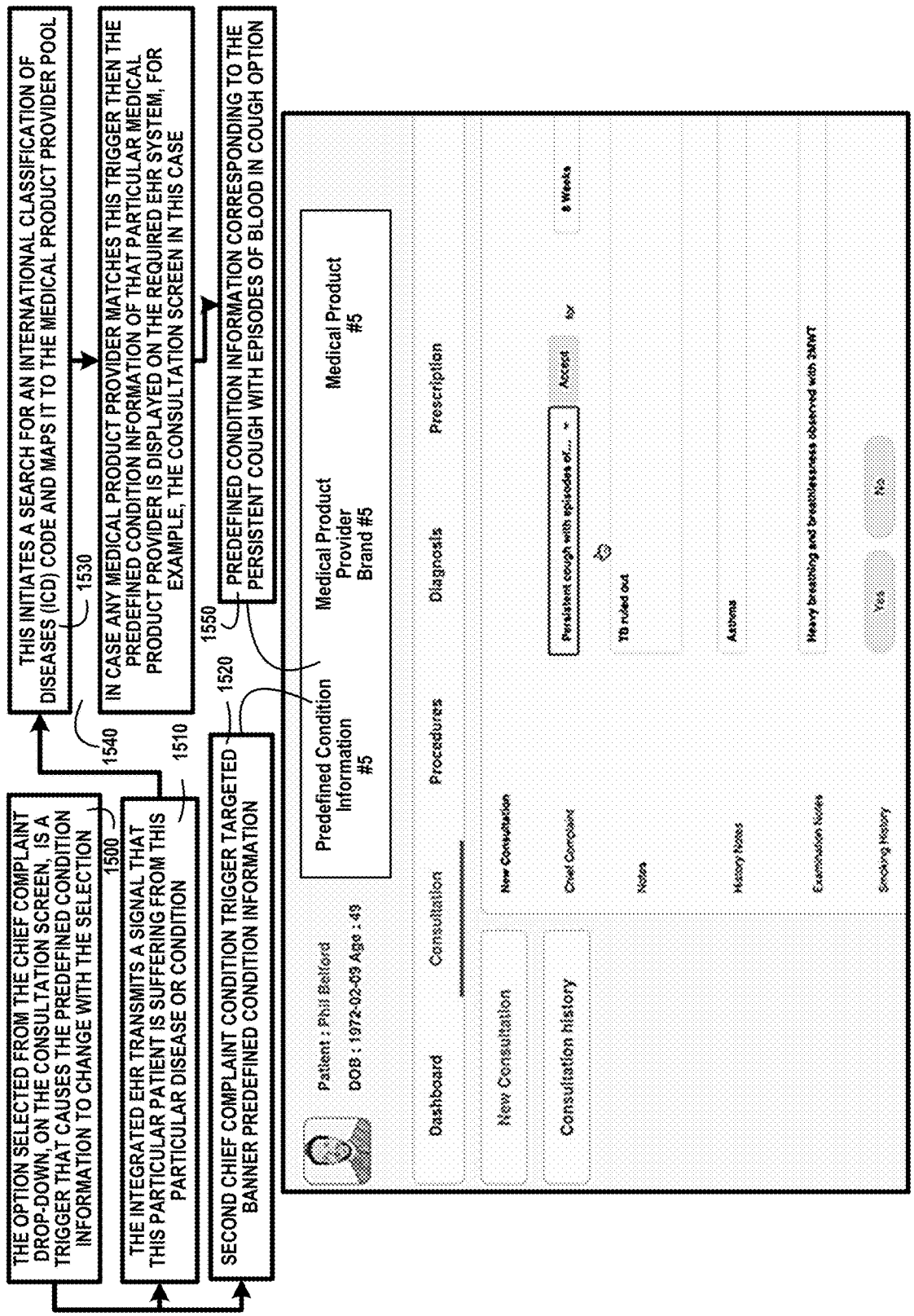
FIG. 15 shows for illustrative purposes only an example of a second chief complaint clinical trigger targeted banner ad of one embodiment.

Second Chief Complaint Clinical Trigger Targeted Banner Ad:

FIG. 15 shows for illustrative purposes only an example of a second chief complaint clinical trigger targeted banner ad of one embodiment. FIG. 15 shows the option selected from the chief complaint drop-down, on the consultation screen, which is a trigger that causes the ad to change with the selection 1500. The integrated EHR transmits a signal that this particular patient is suffering from this particular disease or condition 1510. A second chief complaint clinical trigger targeted banner ad 1520 is displayed when the complaint is changed. This initiates a search for an international classification of diseases (ICD) code and maps it to the advertiser pool 1530. In case any advertiser matches this trigger then the ad of that particular advertiser is displayed on the required EHR system, for example, the consultation screen in this case 1540. An ad corresponding to the persistent cough with episodes of blood in cough option 1550 is displayed of one embodiment.

Figure 16:
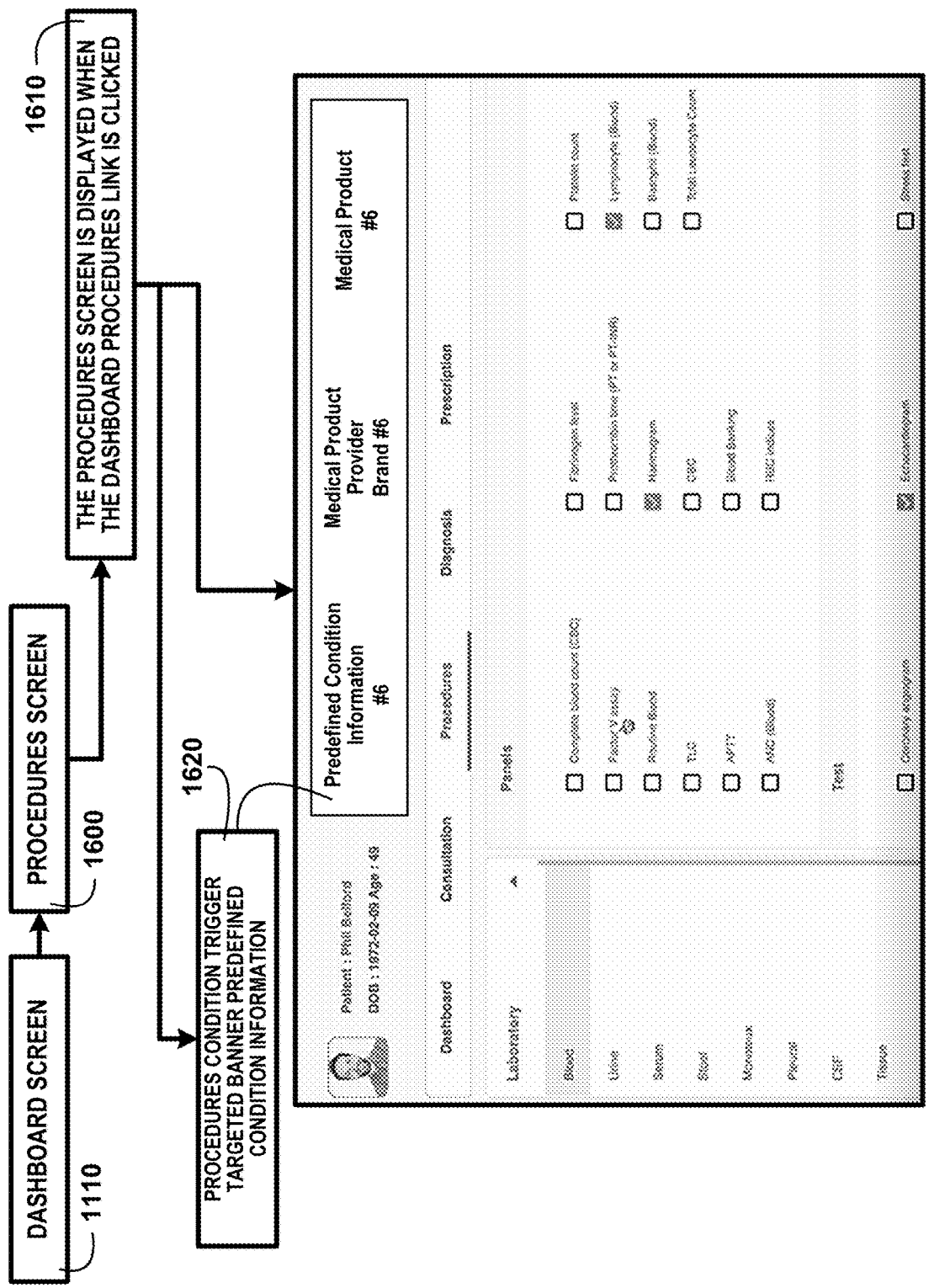
FIG. 16 shows for illustrative purposes only an example of procedures screen of one embodiment.

Procedures Screen:

FIG. 16 shows for illustrative purposes only an example of procedures screen of one embodiment. FIG. 16 shows the dashboard screen 1110. The procedures screen 1600 is displayed. The procedures screen is displayed when the dashboard procedures link is clicked 1610. Displayed is a procedures clinical trigger targeted banner ad 1620 for the physician to observe of one embodiment.

Figure 17:
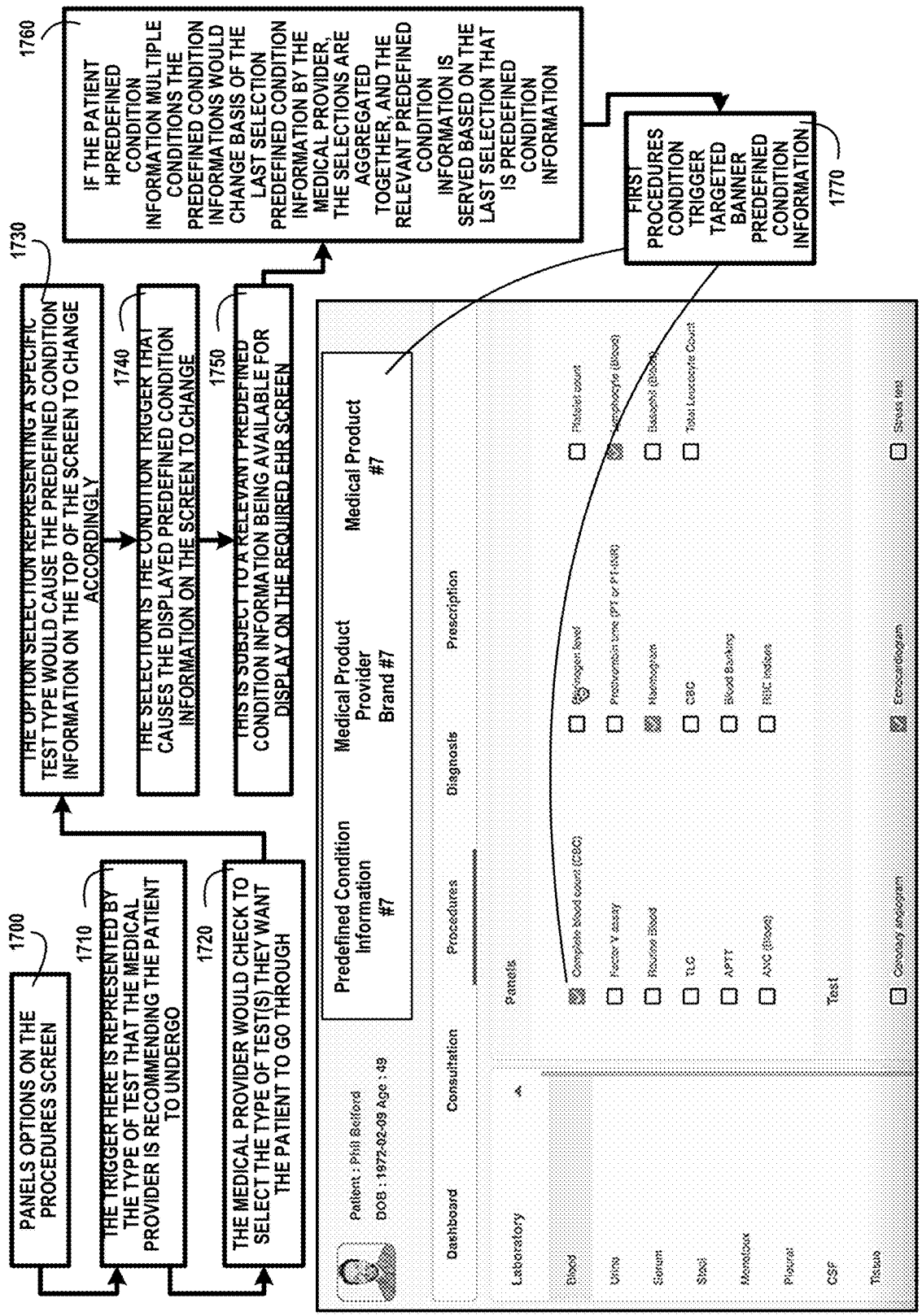
FIG. 17 shows for illustrative purposes only an example of specific tests and clinical triggers of one embodiment.

Specific Tests and Clinical Triggers:

FIG. 17 shows for illustrative purposes only an example of specific tests and clinical triggers of one embodiment. FIG. 17 shows panel options on the procedures screen 1700. The trigger here is represented by the type of test that the physician is recommending the patient undergo 1710. The physician would check to select the type of test(s) they want the patient to go through 1720. The option selection representing a specific test type would cause the ad on the top of the screen to change accordingly 1730. The selection is the clinical trigger that causes the displayed ad on the screen to change 1740. This is subject to a relevant ad being available for display on the required EHR screen 1750. If the patient had multiple conditions the ads would change the basis of the last selection made by the physician, the selections are aggregated together, and the relevant ad is served based on the last selection that is made 1760. Based on the first procedure selected a first procedures clinical trigger targeted banner ad 1770 is displayed of one embodiment.

Figure 18:
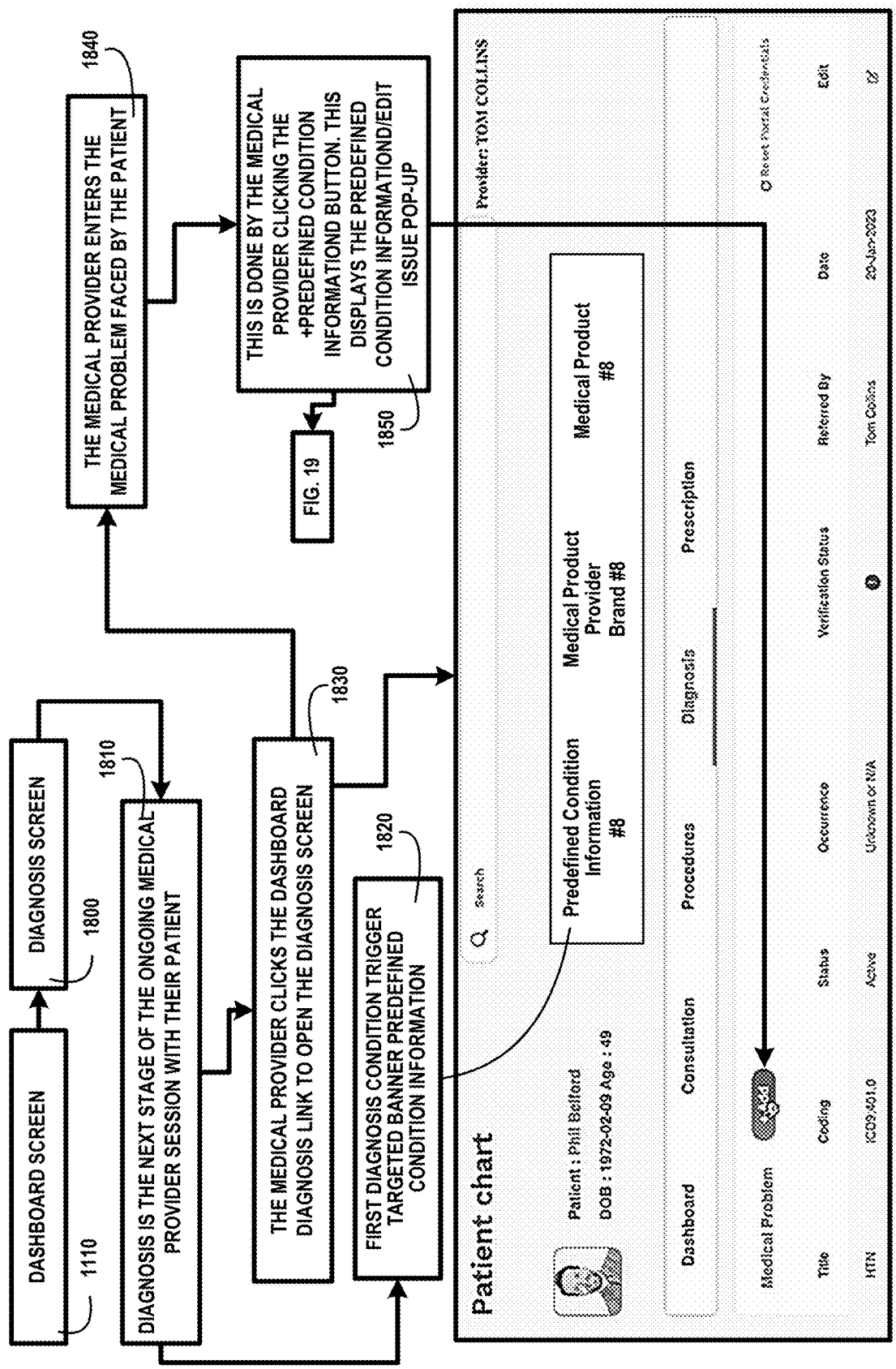
FIG. 18 shows for illustrative purposes only an example of a diagnosis screen of one embodiment.

Diagnosis Screen:

FIG. 18 shows for illustrative purposes only an example of a diagnosis screen of one embodiment. FIG. 18 shows the dashboard screen 1110 with the diagnosis screen 1800 opened. Diagnosis is the next stage of the ongoing physician session with patient 1810. A first diagnosis clinical trigger targeted banner ad 1820 is displayed on the diagnosis screen 1800. The physician clicks the dashboard diagnosis link to open the diagnosis screen 1830. The physician enters the medical problem faced by the patient 1840. This is done by the physician clicking the +add button. This displays the add/edit issue pop-up 1850 of one embodiment. The descriptions continue in FIG. 19.

Figure 19:
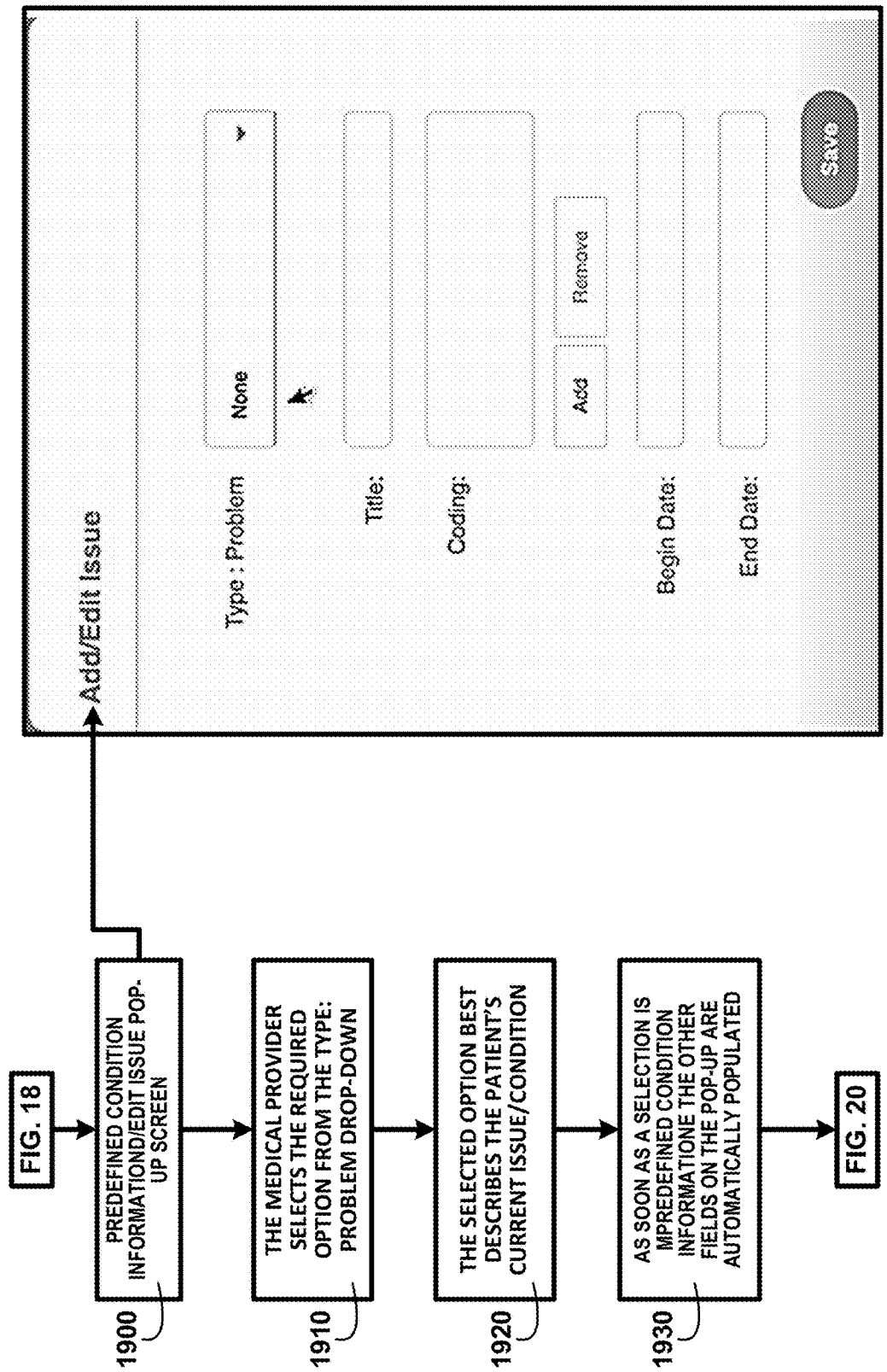
FIG. 19 shows for illustrative purposes only an example of add/edit issue pop-up screen of one embodiment.

Add/Edit Issue Pop-Up Screen:

FIG. 19 shows for illustrative purposes only an example of add/edit issue pop-up screen of one embodiment. FIG. 19 shows a continuation from FIG. 18. The add/edit issue pop-up screen 1900 is displayed after the physician has tapped that tab. The physician selects the required option from the type: problem drop-down 1910. The selected option best describes the patient's current issue/condition 1920. As soon as a selection is made the other fields on the pop-up are automatically populated 1930. The descriptions continue in FIG. 20.

Figure 20:
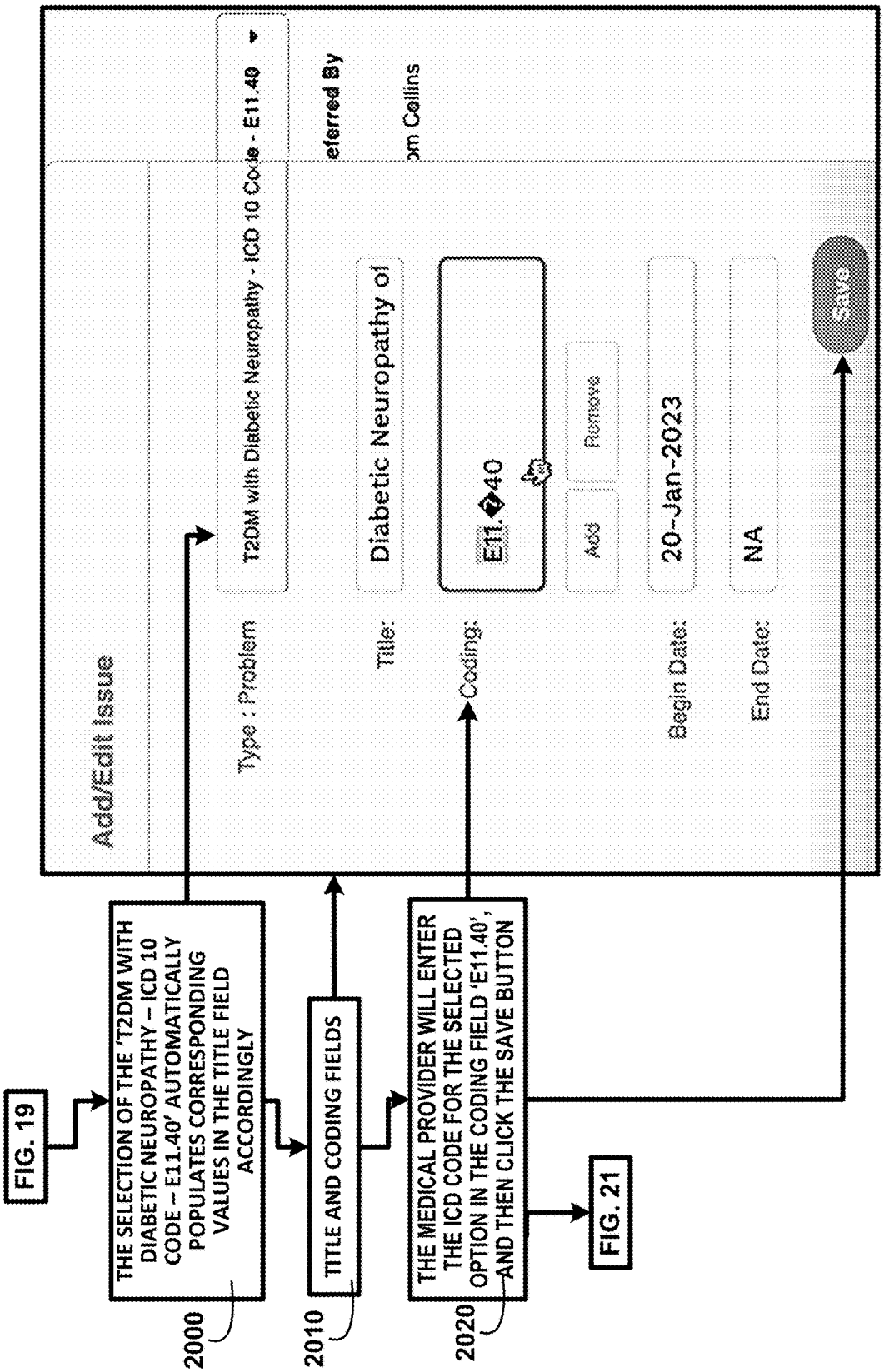
FIG. 20 shows for illustrative purposes only an example of the title and coding fields of one embodiment.

Title and Coding Fields:

FIG. 20 shows for illustrative purposes only an example of the title and coding fields of one embodiment. FIG. 20 shows a continuation from FIG. 19. The selection of the 't2dm with diabetic neuropathy—ICD 10 code—E11.40' automatically populates corresponding values in the title field accordingly 2000. The title and coding fields 2010 will populate data based on the physician's entry of the ICD code. The physician will enter the ICD code for the selected option in the coding field 'e11.40', and then click the save button 2020 of one embodiment. The descriptions continue in FIG. 21.

Figure 21:
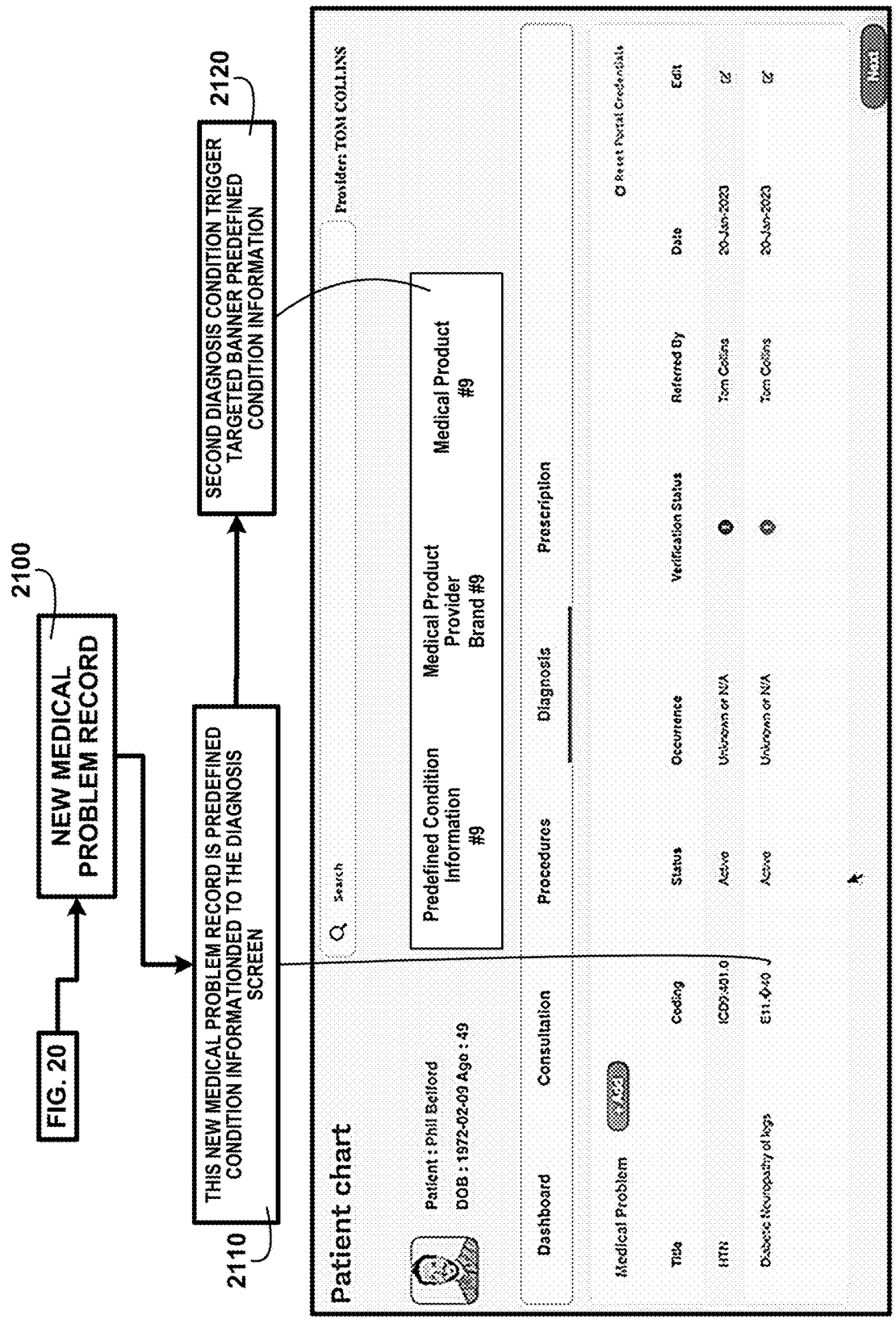
FIG. 21 shows for illustrative purposes only an example of a new medical problem record of one embodiment.

New Medical Problem Record:

FIG. 21 shows for illustrative purposes only an example of a new medical problem record of one embodiment. FIG. 21 shows a continuation from FIG. 20. The physician will proceed to create a new medical problem record 2100 of the patient's condition. This new medical problem record is added to the diagnosis screen 2110. A second diagnosis clinical trigger targeted banner ad 2120 is prompted by the new medical problem addition of one embodiment.

Figure 22:
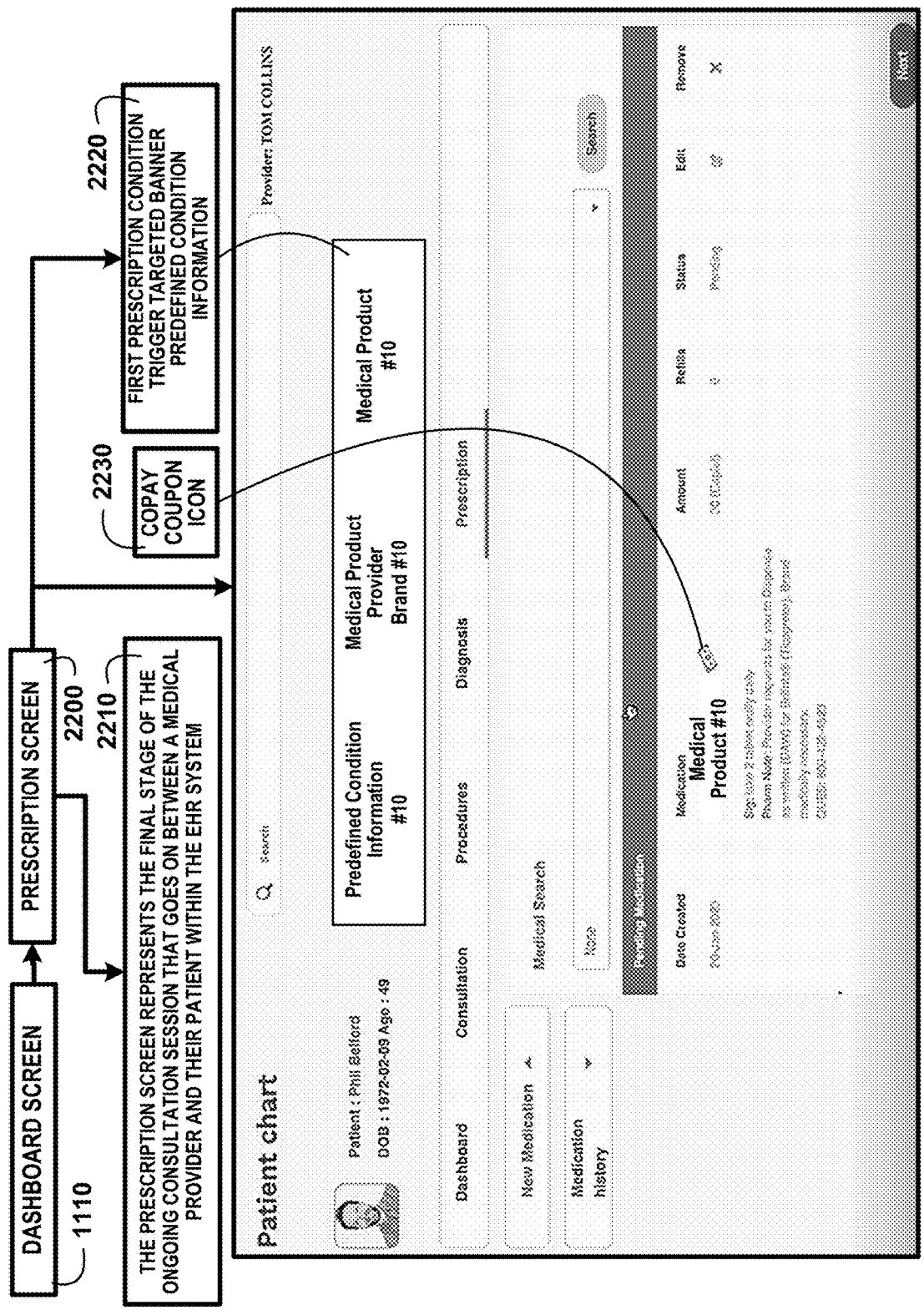
FIG. 22 shows for illustrative purposes only an example of a prescription screen of one embodiment.

Prescription Screen:

FIG. 22 shows for illustrative purposes only an example of a prescription screen of one embodiment. FIG. 22 shows the dashboard screen 1110 with the prescription screen 2200 displayed. The prescription screen represents the final stage of the ongoing consultation session that goes on between a physician and their patient within the EHR system 2210. A first prescription clinical trigger targeted banner ad 2220 is displayed that also shows a copay coupon icon 2230 indicating a discount coupon is available for that medication at this pharmacy of one embodiment.

Figure 23:
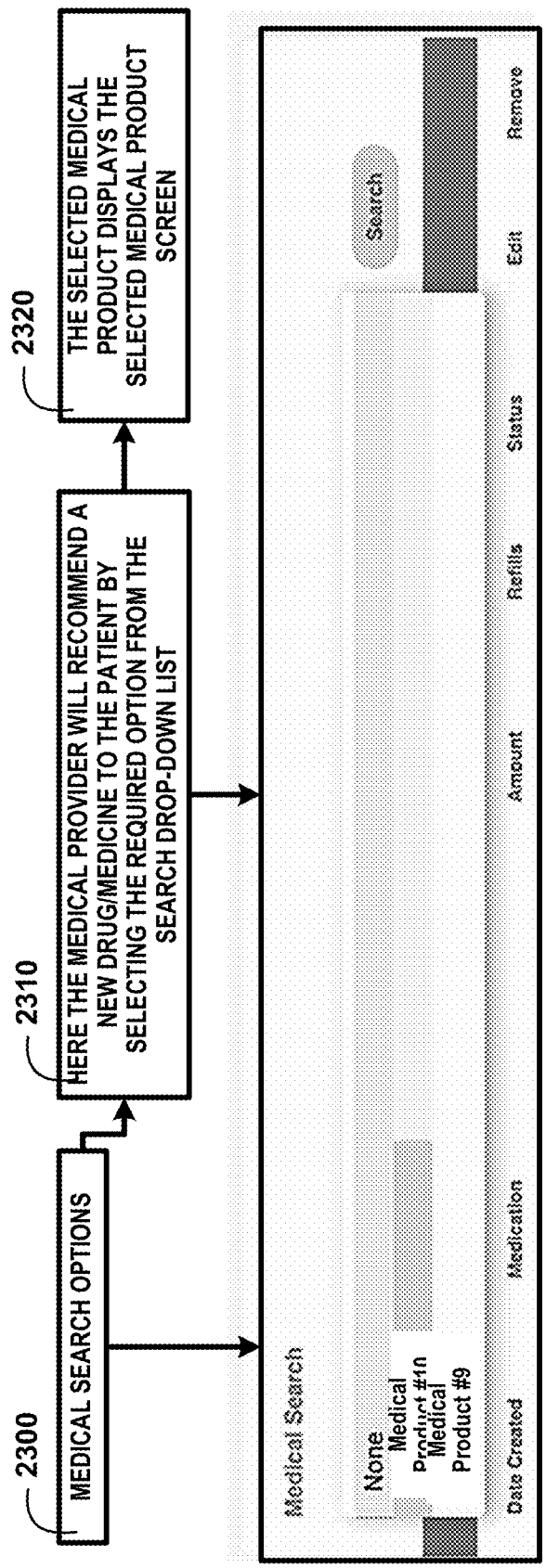
FIG. 23 shows for illustrative purposes only an example of a new drug/medicine of one embodiment.

New Drug/Medicine:

FIG. 23 shows for illustrative purposes only an example of a new drug/medicine of one embodiment. FIG. 23 shows medical search options 2300. Here the physician will recommend a new drug/medicine to the patient by selecting the required option from the search drop-down list 2310. The selected medication displays the selected medication screen 2320 of one embodiment.

Figure 24:
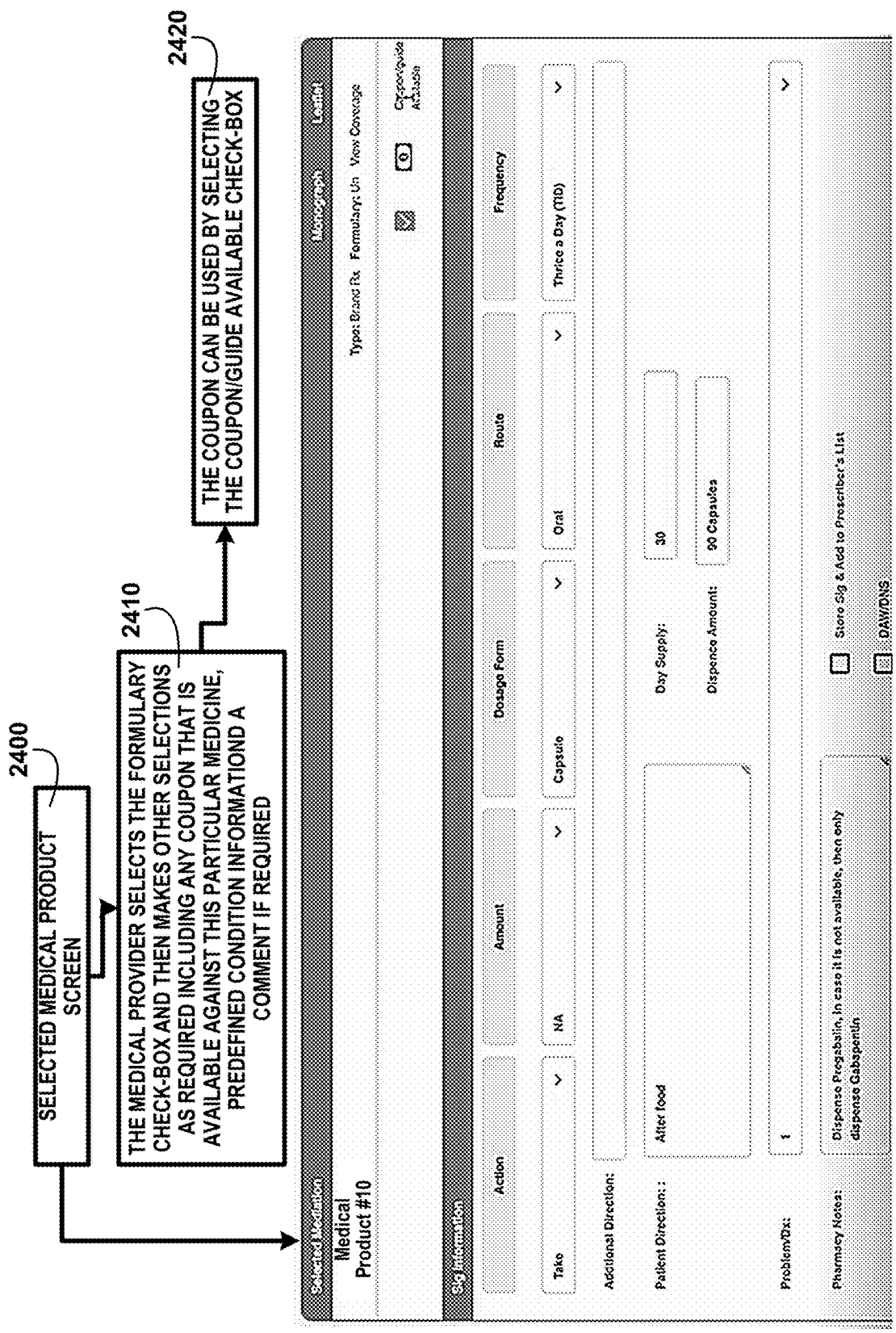
FIG. 24 shows for illustrative purposes only an example of a selected medication screen of one embodiment.

Selected Medication Screen:

FIG. 24 shows for illustrative purposes only an example of a selected medication screen of one embodiment. FIG. 24 shows a selected medication screen 2400. The physician selects the formulary check-box and then makes other selections as required including any coupon that is available against this particular medicine, add a comment if required 2410. The coupon can be used by selecting the coupon/guide available check-box 2420 of one embodiment.

Figure 25:
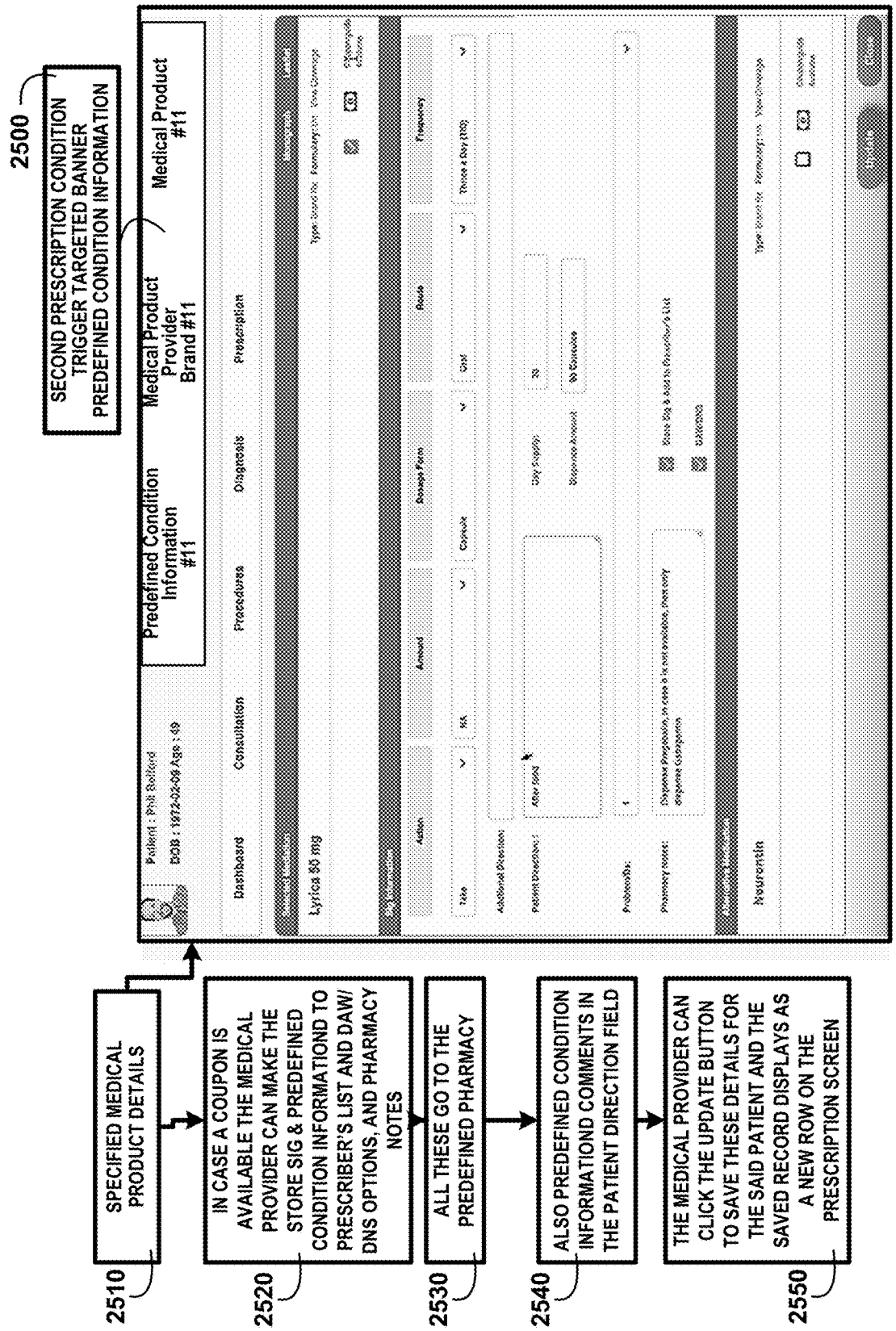
FIG. 25 shows for illustrative purposes only an example of specified medication details of one embodiment.

Specified Medication Details:

FIG. 25 shows for illustrative purposes only an example of specified medication details of one embodiment. FIG. 25 shows a second prescription clinical trigger targeted banner ad 2500 is displayed related to the new medication selected. Specified medication details 2510 are displayed for the new medication selected. In case a coupon is available the physician can make the store sig & add it to the prescriber's list and daw/dns options, and pharmacy notes 2520. All these go to the predefined pharmacy 2530. The physician can also add comments in the patient direction field 2540. The physician can click the update button to save these details for the said patient and the saved record displays as a new row on the prescription screen 2550 of one embodiment.

Figure 26:
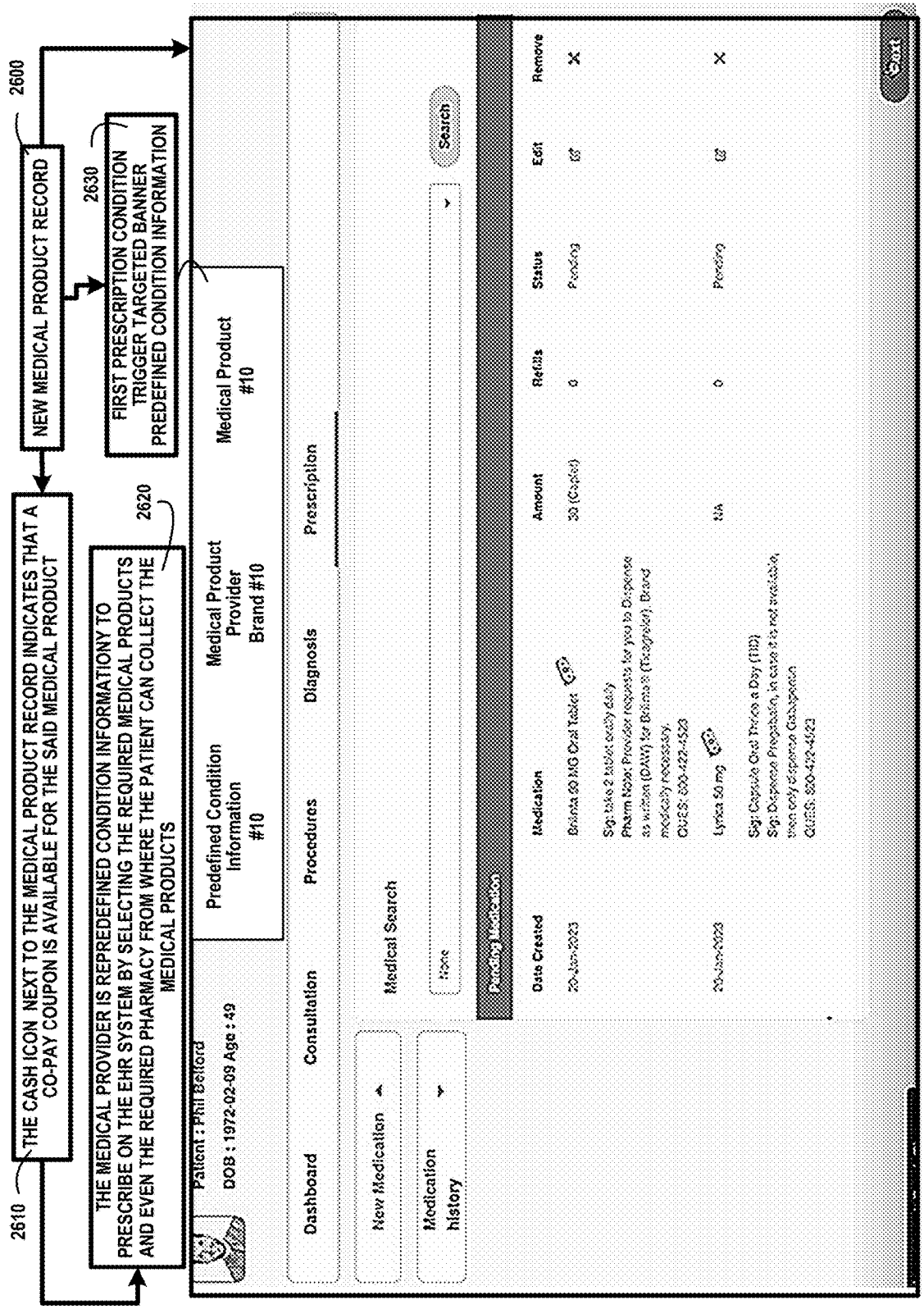
FIG. 26 shows for illustrative purposes only an example of a prescription clinical trigger targeted banner ad of one embodiment.

Prescription Clinical Trigger Targeted Banner Ad:

FIG. 26 shows for illustrative purposes only an example of a prescription clinical trigger targeted banner ad of one embodiment. FIG. 26 shows a new medication record 2600. The cash icon next to the medication record indicates that a co-pay coupon is available for the said medication 2610. The physician is ready to prescribe on the EHR system by selecting the required medications and even the required pharmacy from where the patient can collect the medications 2620. The first prescription clinical trigger targeted banner ad 2630 is also displayed in preparation for ordering the prescription to the pharmacy of one embodiment.

Prescription Conversation Pop-Up:

FIG. 27 shows for illustrative purposes only an example of a prescription confirmation pop-up of one embodiment. FIG. 27 shows the screen to select pharmacy 2700. Finally, the physician clicks the process medications button, which displays the prescription confirmation pop-up 2710 of one embodiment.

Figure 28:
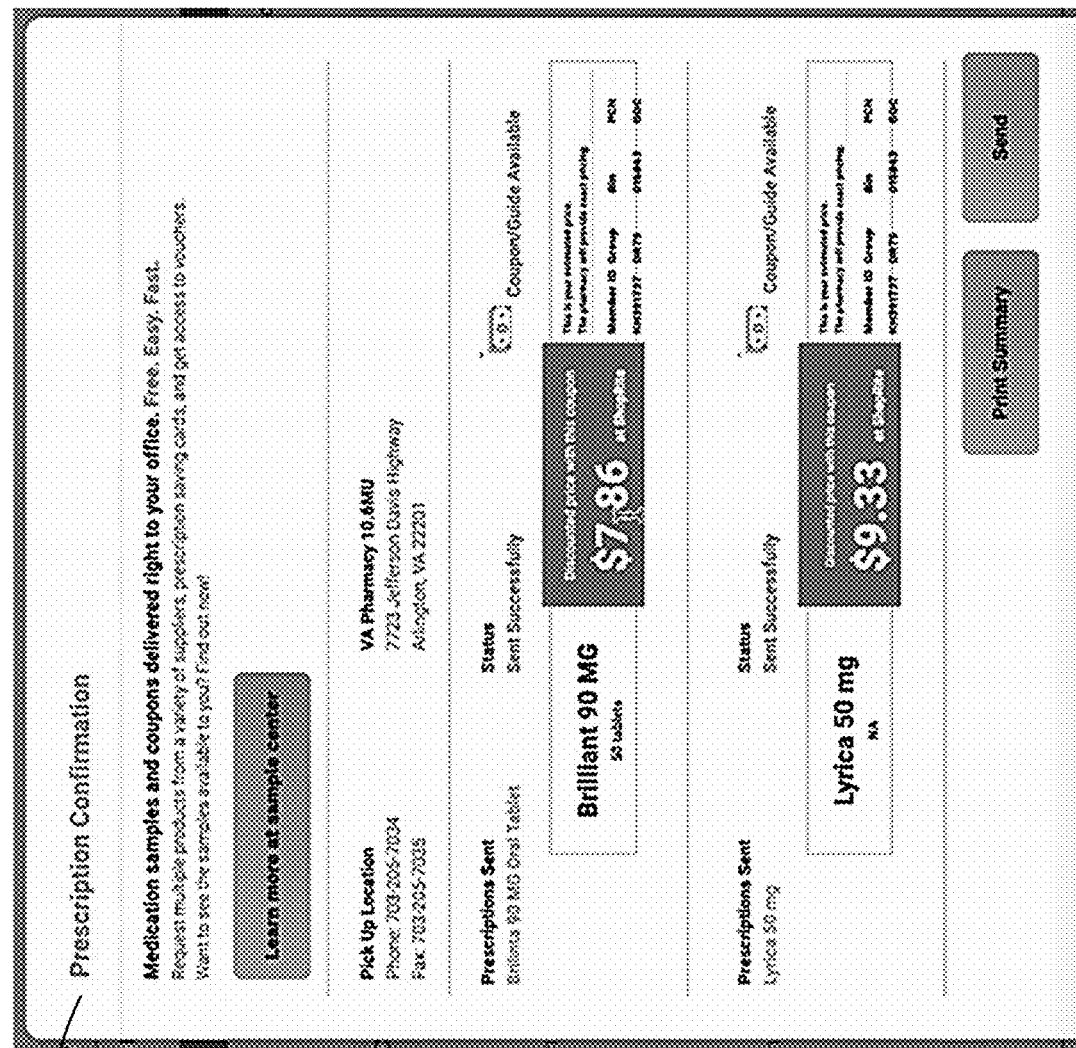
FIG. 28 shows for illustrative purposes only an example of a prescription confirmation pop-up of one embodiment.
Figure 28:
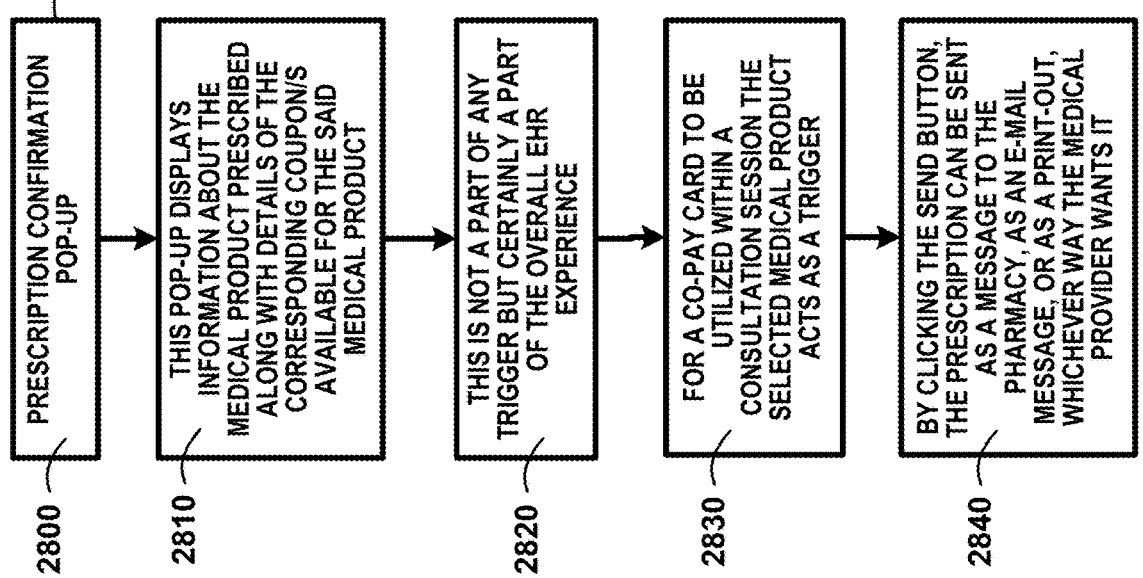

Prescription Confirmation Pop-Up:

FIG. 28 shows for illustrative purposes only an example of a prescription confirmation pop-up of one embodiment. FIG. 28 shows a prescription confirmation pop-up 2800. This pop-up displays information about the medication prescribed along with details of the corresponding coupon/s available for the said medication 2810. This is not a part of any trigger but certainly a part of the overall EHR experience 2820. For a co-pay card to be utilized within a consultation session the selected medication acts as a trigger 2830. By clicking the send button, the prescription can be sent as a message to the pharmacy, as an e-mail message, or as a print-out, whichever way the physician wants it 2840 of one embodiment.

Figure 29:
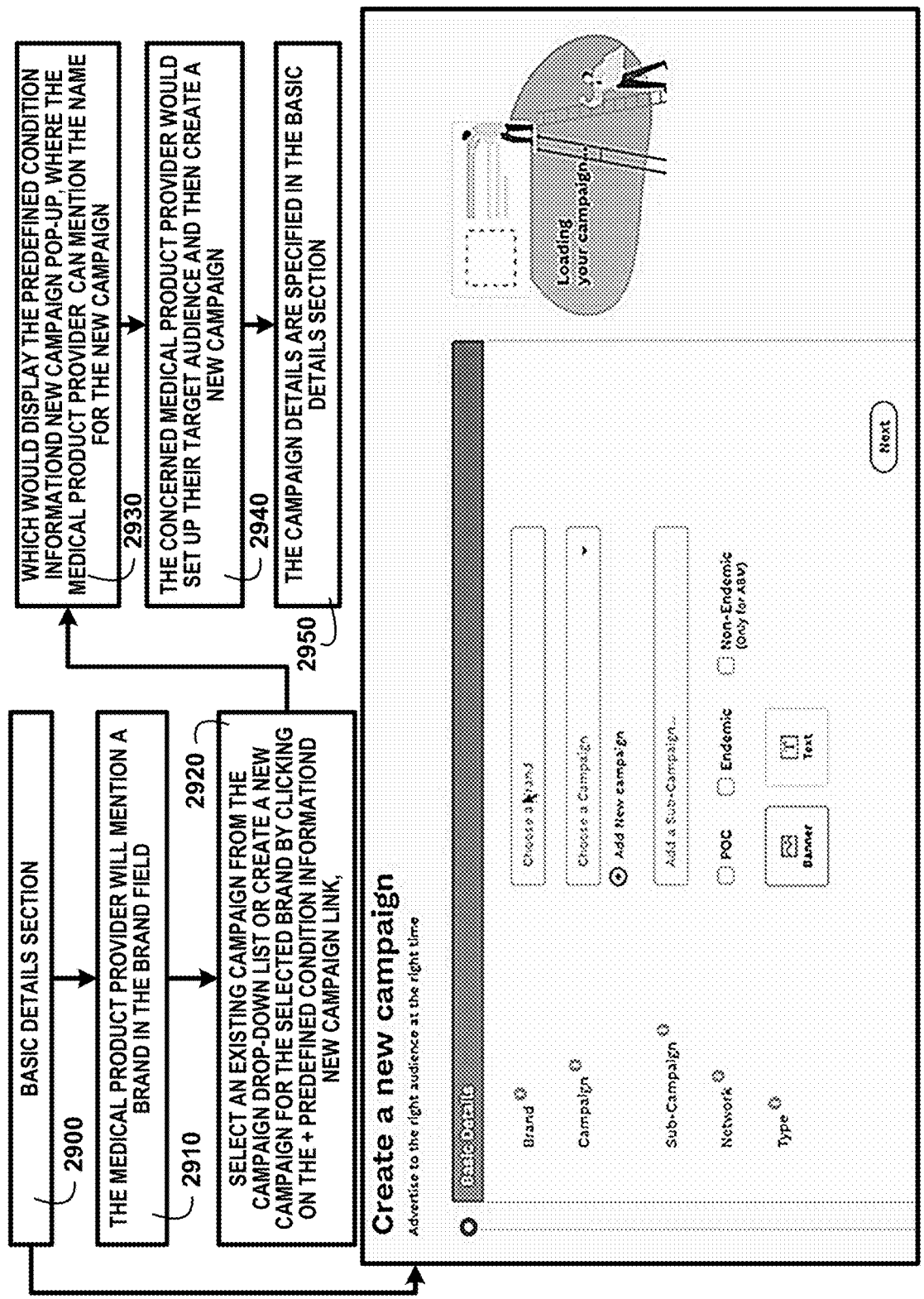
FIG. 29 shows for illustrative purposes only an example of creating a new campaign of one embodiment.

Create a New Campaign:

FIG. 29 shows for illustrative purposes only an example of creating a new campaign of one embodiment. FIG. 29 shows a basic details section 2900 the advertiser uses to begin the creation of a new campaign. The advertiser will mention a brand in the brand field 2910. The advertiser can select an existing campaign from the campaign drop-down list or create a new campaign for the selected brand by clicking on the +add new campaign link 2920. The +add new campaign link which would display the add new campaign pop-up, where the advertiser can mention the name of the new campaign 2930. The concerned advertiser would set up their target audience and then create a new campaign 2940. The campaign details are specified in the basic details section 2950 for review of one embodiment.

Figure 30:
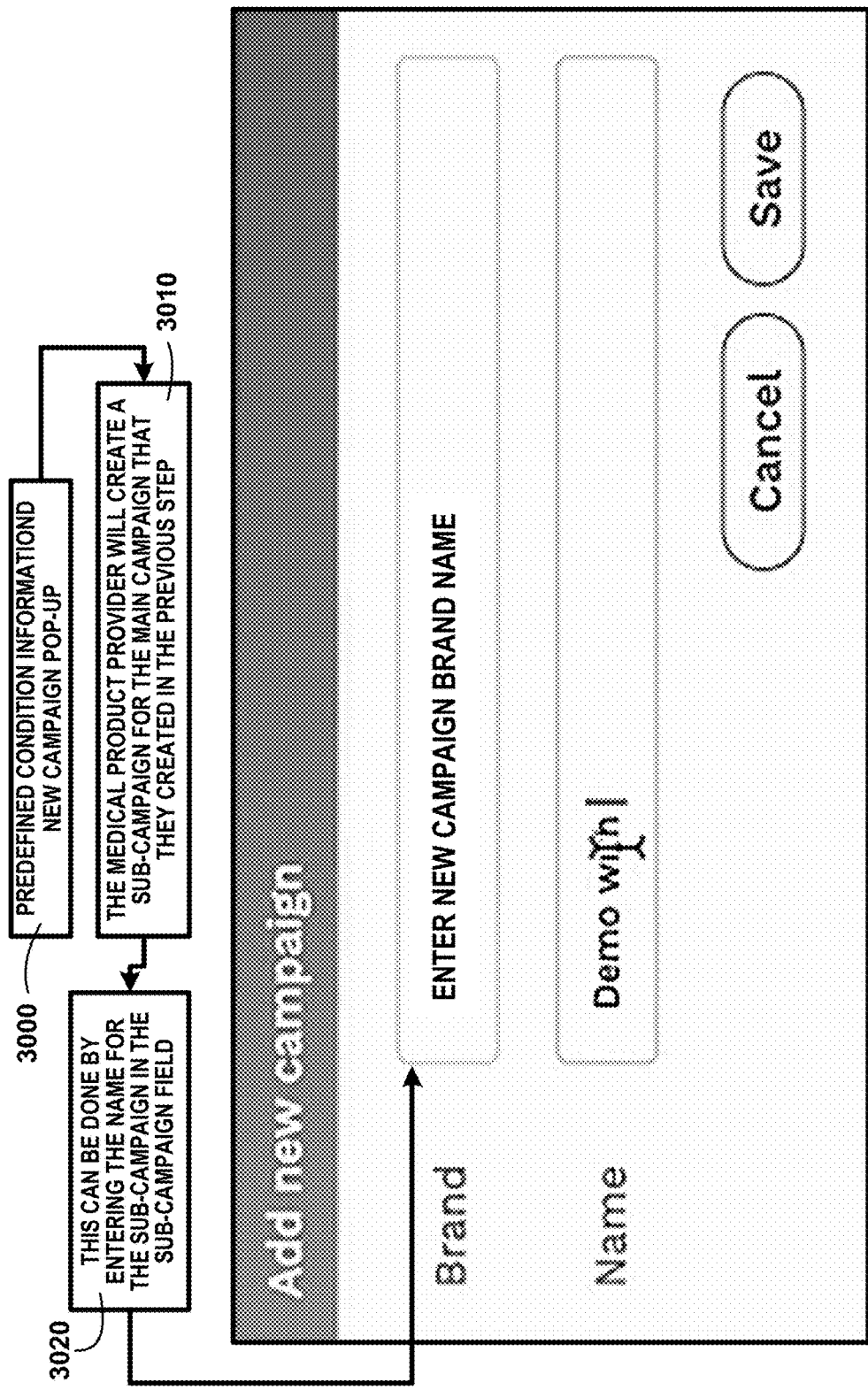
FIG. 30 shows for illustrative purposes only an example of an add new campaign pop-up of one embodiment.

Add New Campaign Pop-Up:

FIG. 30 shows for illustrative purposes only an example of add new campaign pop-up of one embodiment. FIG. 30 shows the add new campaign pop-up 3000. The advertiser will create a sub-campaign for the main campaign that they created in the previous step 3010. This can be done by entering the name for the sub-campaign in the sub-campaign field 3020 of one embodiment.

Figure 31:
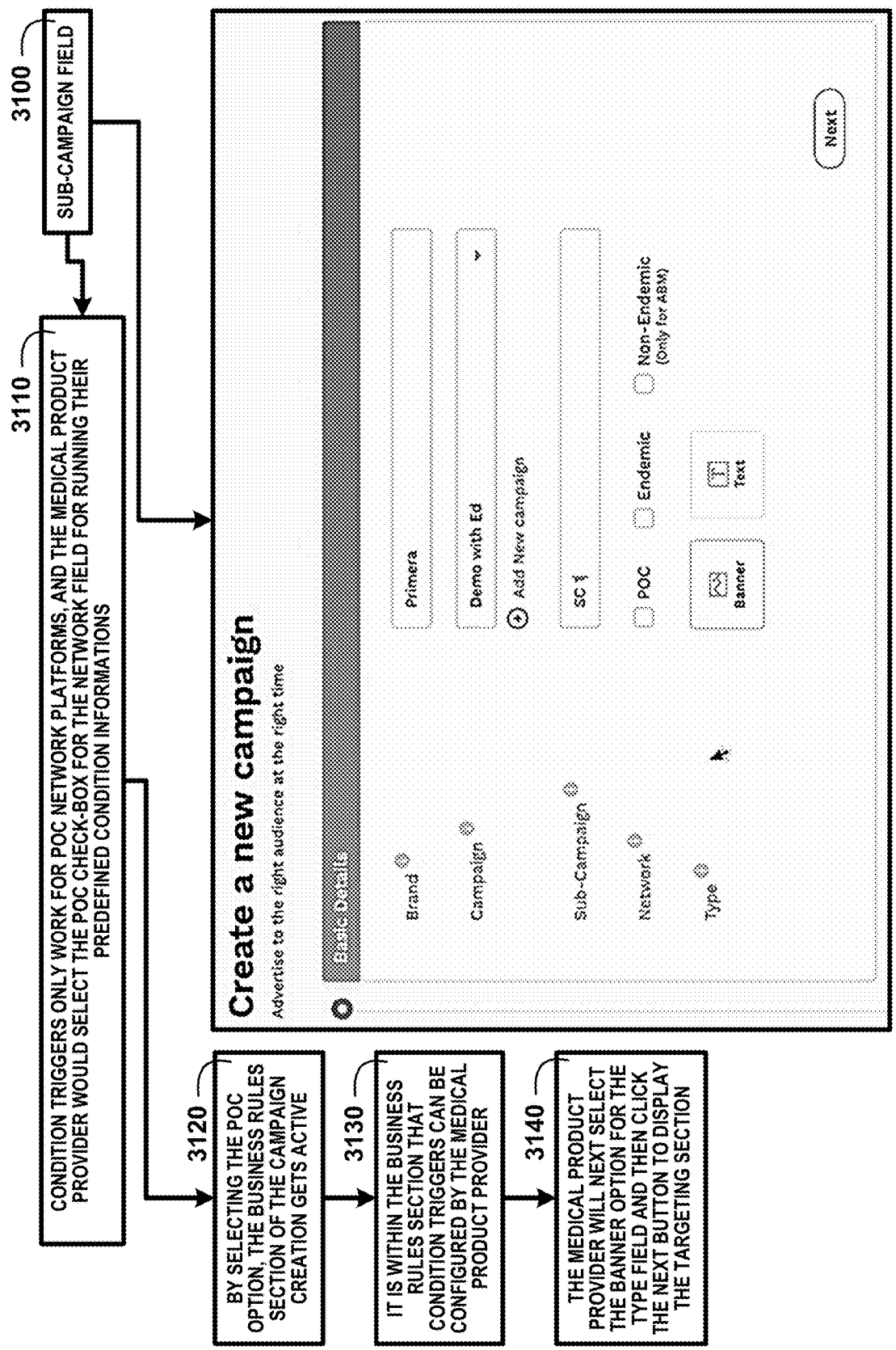
FIG. 31 shows for illustrative purposes only an example of the POC selection of one embodiment.

POC Selection:

FIG. 31 shows for illustrative purposes only an example of the POC selection of one embodiment. FIG. 31 shows a sub-campaign field 3100. Clinical triggers only work for POC network platforms, and the advertiser would select the POC check-box for the network field for running their advertisements 3110. By selecting the POC option, the business rules section of the campaign creation gets active 3120. It is within the business rules section that clinical triggers can be configured by the advertiser 3130. The advertiser will next select the banner option for the type field and then click the next button to display the targeting section 3140 of one embodiment.

Figure 32:
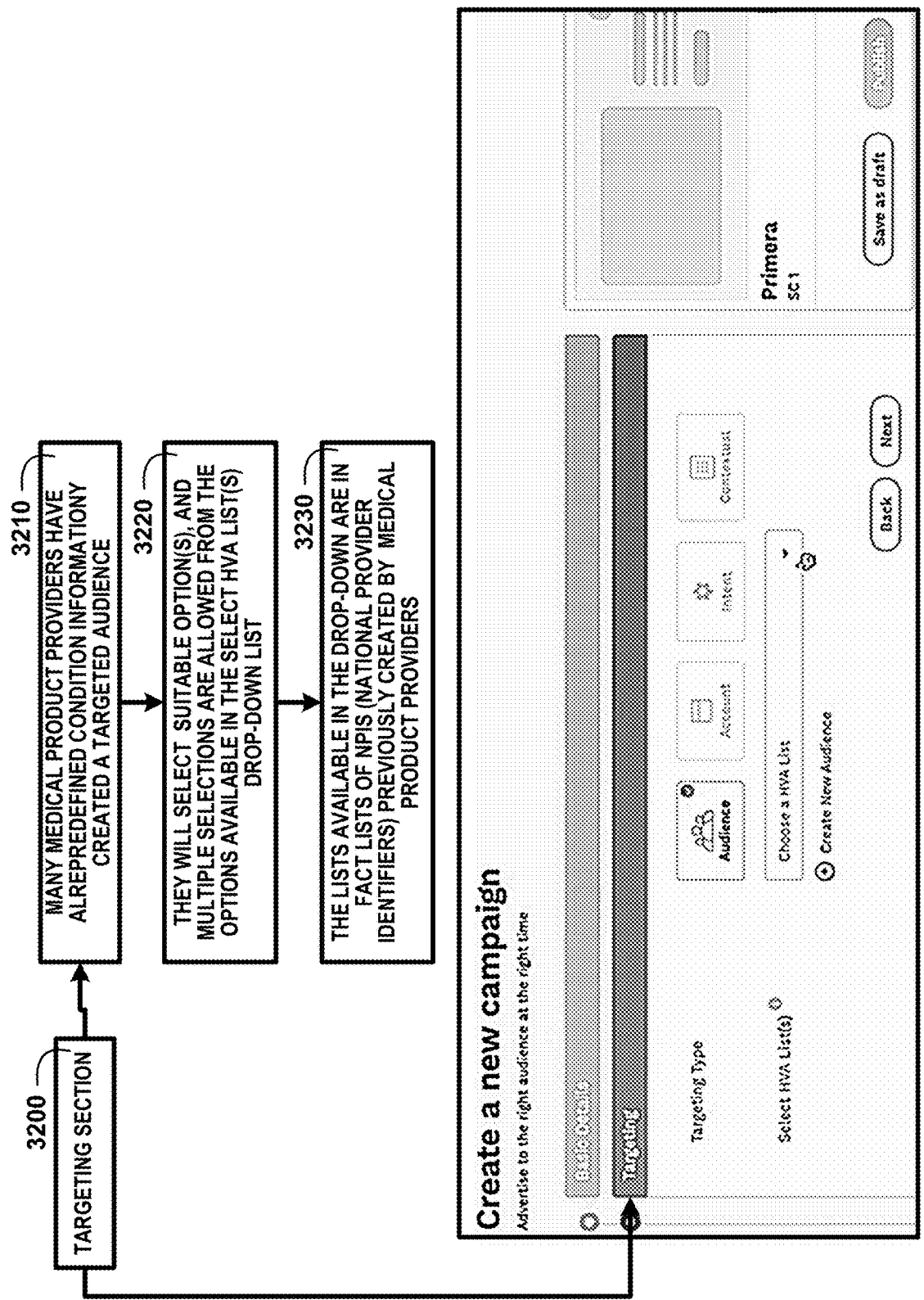
FIG. 32 shows for illustrative purposes only an example of a targeted audience of one embodiment.

Targeted Audience:

FIG. 32 shows for illustrative purposes only an example of a targeted audience of one embodiment. FIG. 32 shows a targeting section 3200. Many advertisers have already created a targeted audience 3210. They will select suitable option(s), and multiple selections are allowed from the options available in the select National Provider Identifier list(s) drop-down list 3220. The lists available in the drop-down are in fact lists of NPIS (national provider identifiers) previously created by advertisers 3230 of one embodiment.

Figure 33:
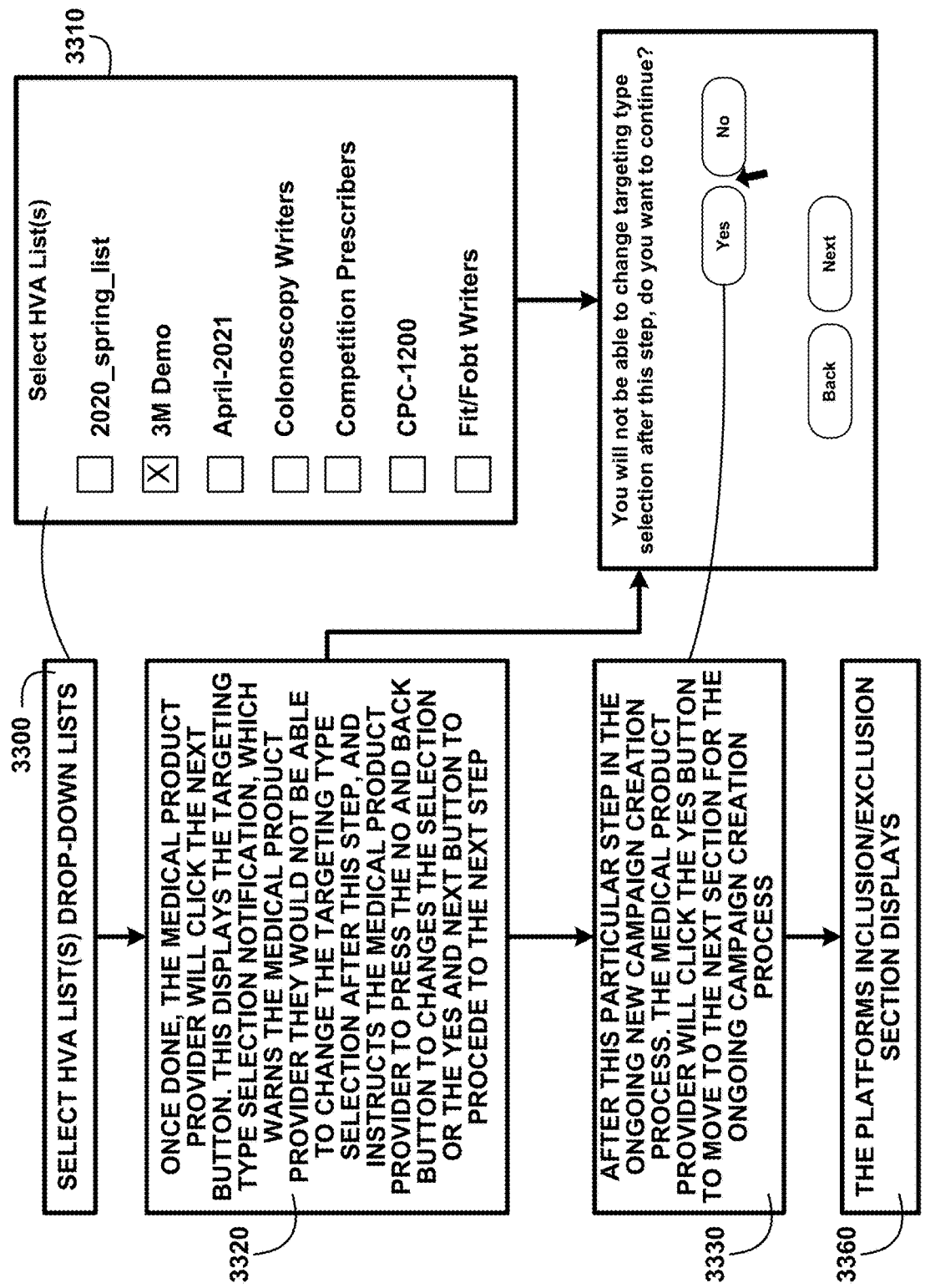
FIG. 33 shows for illustrative purposes only an example of select National Provider Identifier list(s) drop-down lists of one embodiment.

Select National Provider Identifier List(s) Drop-Down Lists:

FIG. 33 shows for illustrative purposes only an example of select National Provider Identifier list(s) drop-down lists of one embodiment. FIG. 33 shows select National Provider Identifier list(s) drop-down lists 3300. The select National Provider Identifier list(s) 3310 screen is used to designate National Provider Identifier groups the advertiser may select.

Once done, the advertiser will click the Next button. This displays the targeting type selection notification, which warns the advertiser they would not be able to change the targeting type selection after this step, and instructs the advertiser to press the No and Back buttons to change the selection or the Yes and Next buttons to proceed to the next step 3320.

After this particular step in the ongoing new campaign creation process, the advertiser will click the yes button to move to the next section for the ongoing campaign creation process 3330. The platforms inclusion/exclusion section displays 3360 next of one embodiment.

Figure 34:
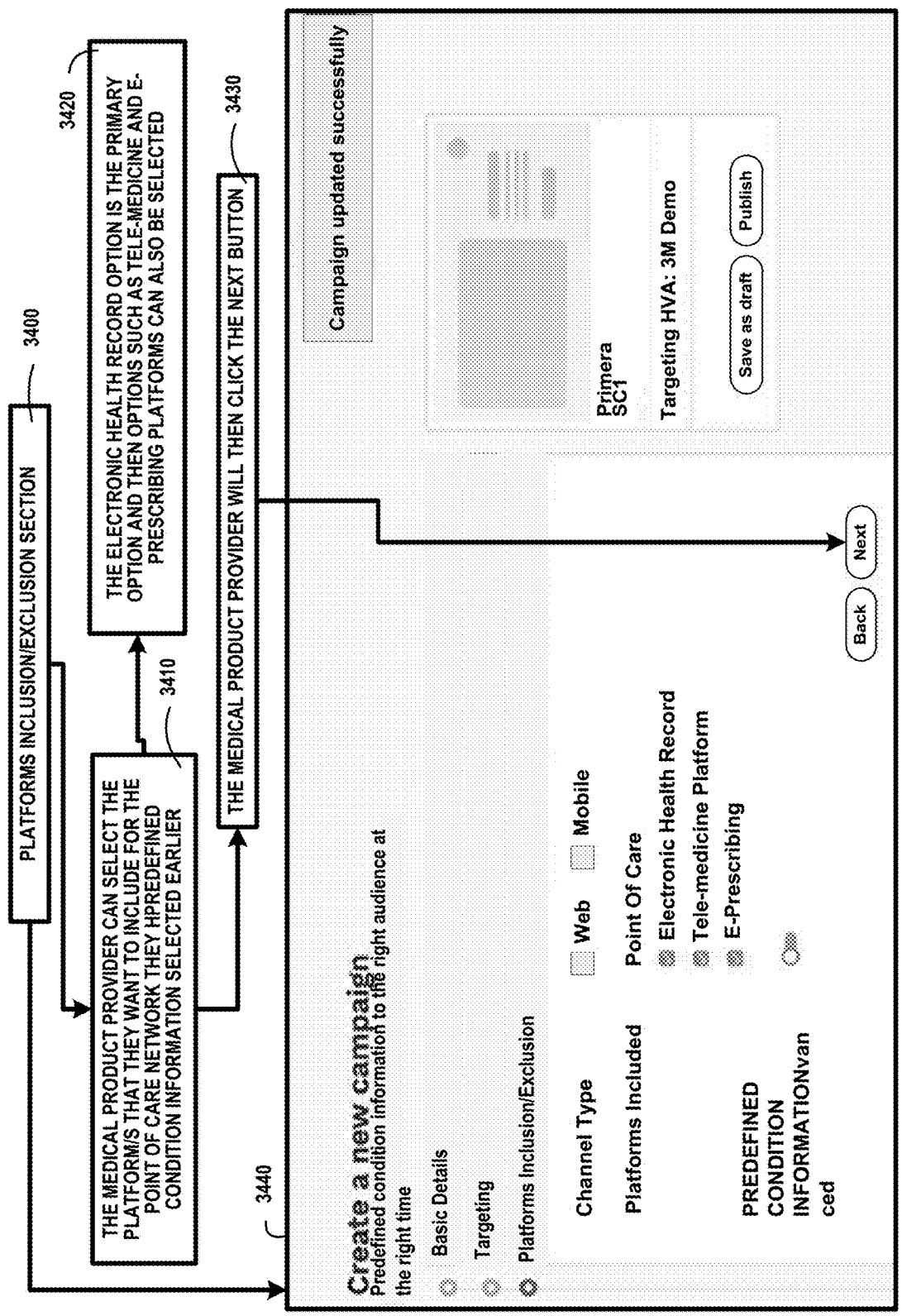
FIG. 34 shows for illustrative purposes only an example of the platforms inclusion/exclusion section of one embodiment.

Platforms Inclusion/Exclusion Section:

FIG. 34 shows for illustrative purposes only an example of the platforms inclusion/exclusion section of one embodiment. FIG. 34 shows a platform inclusion/exclusion section 3400. The advertiser can select the platform(s) that they want to include for the point of care network they had selected earlier 3410. The electronic health record option is the primary option and then options such as telemedicine and e-prescribing platforms can also be selected 3420. The advertiser will then click the next button 3430. Creating a new campaign screen is displayed 3440 of one embodiment.

Figure 35:
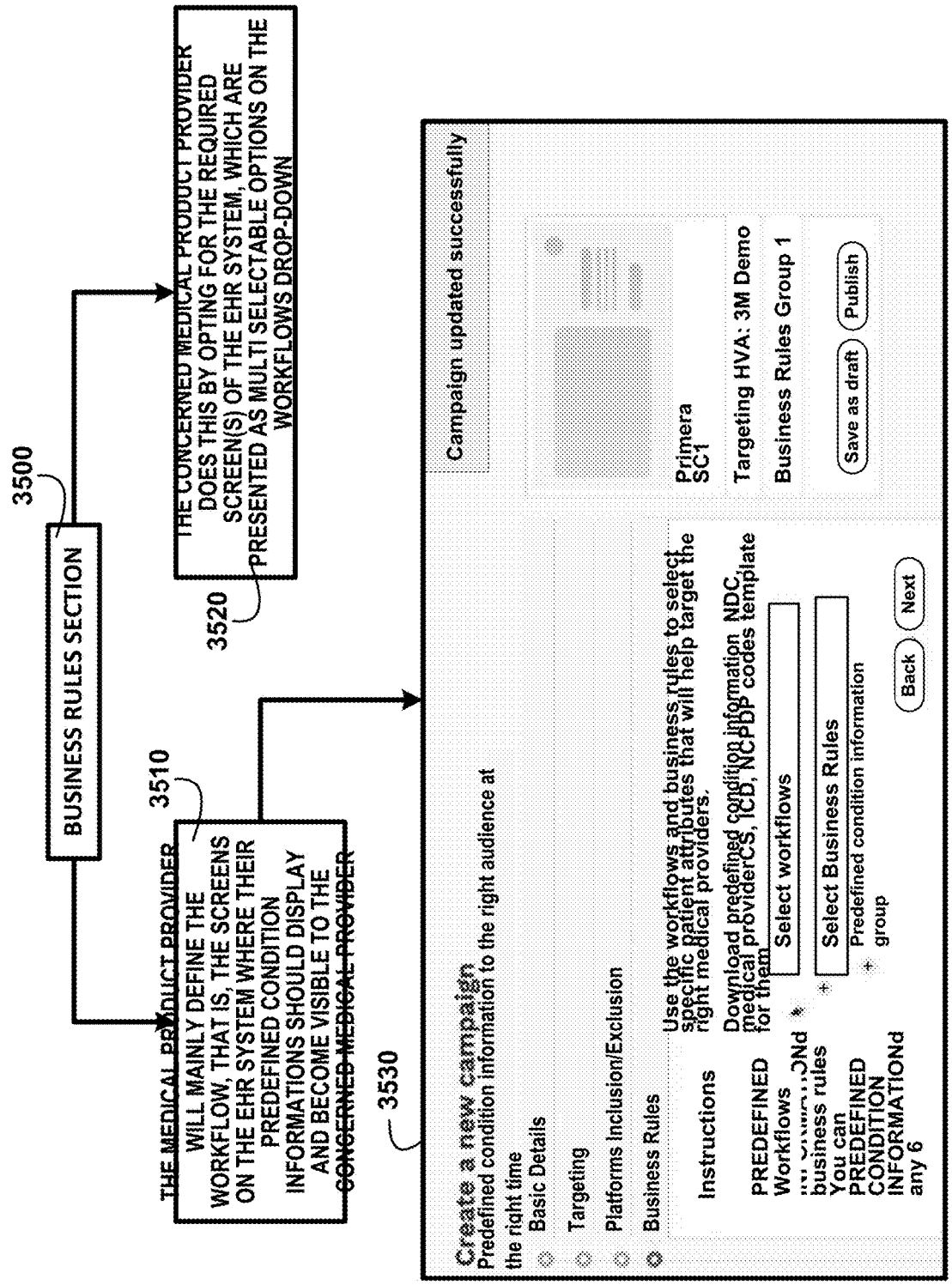
FIG. 35 shows for illustrative purposes only an example of defining the workflow of one embodiment.

Define the Workflow:

FIG. 35 shows for illustrative purposes only an example of defining the workflow of one embodiment. FIG. 35 shows the business rules section 3500. The advertiser will mainly define the workflow, that is, the screens on the EHR system where their ads should display and become visible to the concerned physician 3510. The concerned advertiser does this by opting for the required screen(s) of the EHR system, which is presented as multi-selectable options on the workflows drop-down 3520. Create a new campaign screen is displayed for the business rules section selections 3530 of one embodiment.

Figure 36:
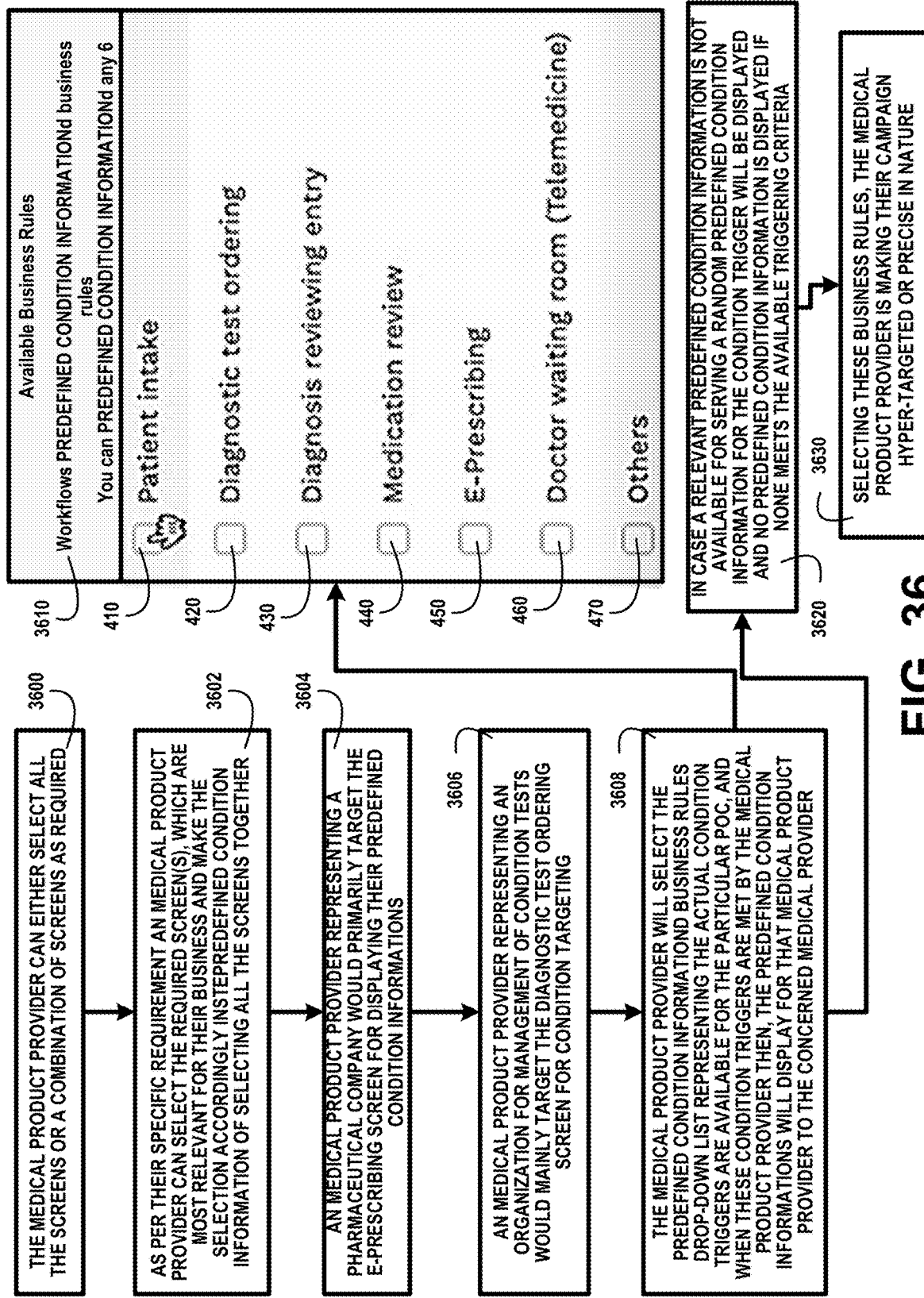
FIG. 36 shows for illustrative purposes only an example of available business rules of one embodiment.

Available Business Rules:

FIG. 36 shows for illustrative purposes only an example of available business rules of one embodiment. FIG. 36 shows the advertiser can either select all the screens or a combination of screens as required 3600. As per their specific requirement, an advertiser can select the required screen(s), which are most relevant for their business and make the selection accordingly instead of selecting all the screens together 3602. An advertiser representing a pharmaceutical company would primarily target the e-prescribing screen for displaying their ads 3604. An advertiser representing an organization for the management of clinical tests would mainly target the diagnostic test ordering screen for clinical targeting 3606.

The advertiser will select the add business rules drop-down list representing the actual clinical triggers that are available for the particular POC, and when these clinical triggers are met by the advertiser then, the ads will display for that advertiser to the concerned physician 3608.

Available business rules workflows add business rules you can add any 6 3610. Patient intake 410, Diagnostic test ordering 420, Diagnosis reviewing entry 430, Medication review 440, E-prescribing 450, Doctor waiting room (telemedicine) 460, and Others 470. In case a relevant ad is not available for serving a random ad for the clinical trigger will be displayed and no ad is displayed if none meets the available triggering criteria 3620. Selecting these business rules, the advertiser is making their campaign hyper-targeted or precise in nature 3630 of one embodiment.

A Patient Calendar

Figure 37:
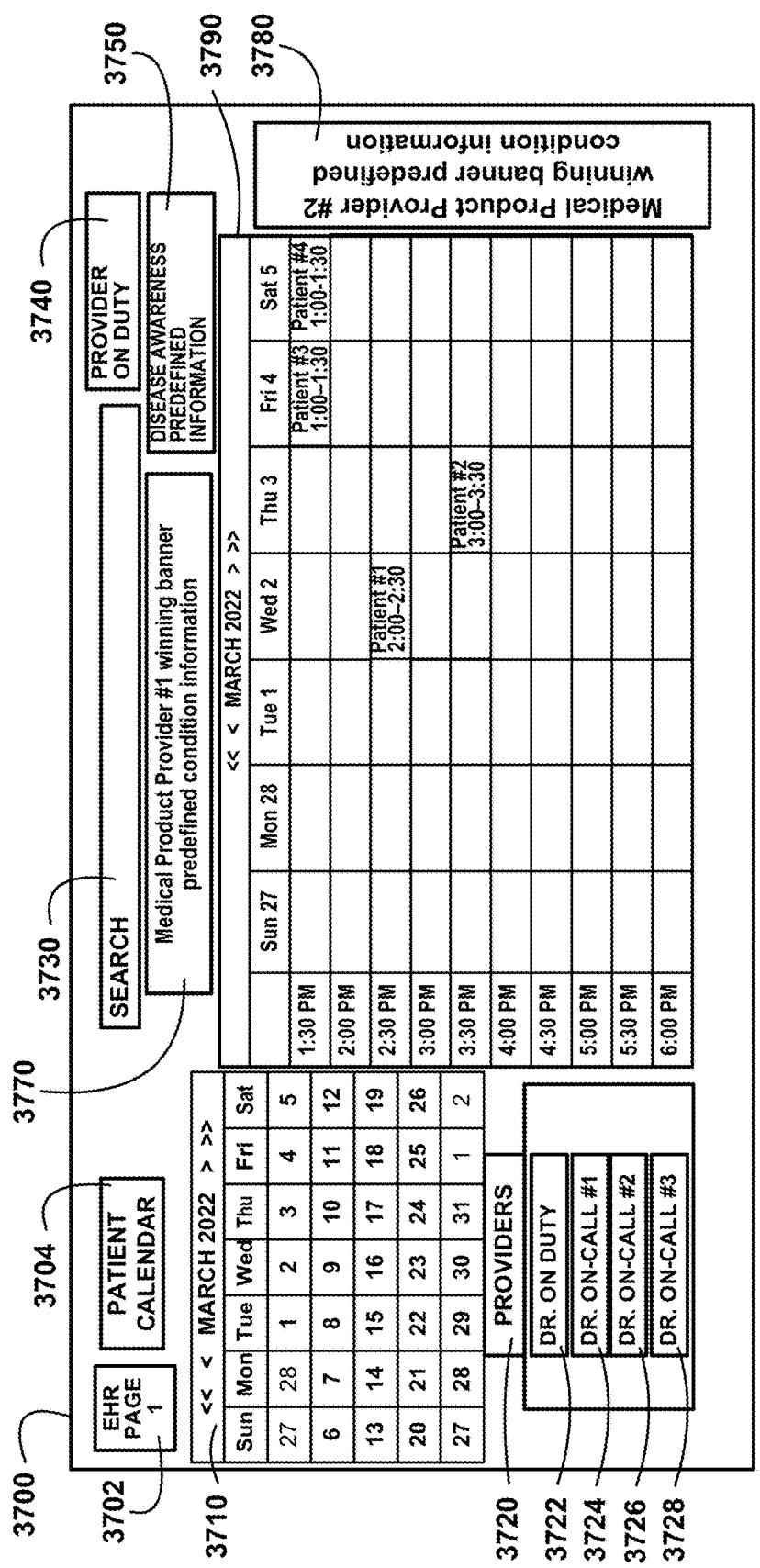
FIG. 37 shows for illustrative purposes only an example of a patient calendar of one embodiment.

FIG. 37 shows for illustrative purposes only an example of a patient calendar of one embodiment. FIG. 37 shows in one embodiment, for example, a physician-patient workflow webpage 3700. An example of a physician-patient workflow webpage 3700 is an EHR page 1 3702 displaying a patient calendar 3704. The patient calendar 3704 shows the current month calendar 3710 and a list of the point of care providers 3720 including a Physician on duty 3722, a Physician on call #1 3724, a Physician on call #2 3726, and a Physician on call #3 3728. A search 3730 tab allows the EHR system provider 540 Physician on duty 3740 to search the EHR of a patient.

In one embodiment, for example, a space on the workflow webpage displays a disease awareness message 3750 the physician can activate to get updated information on a patient's condition. The workflow webpage is also displaying a product advertiser #1 winning banner ad 3770 and a product advertiser #2 winning banner ad 3780 on the provider-patient appointment calendar 3790. The display of the ads saves the physician time by making the information on the product readily available of one embodiment.

A Patient Chart

Figure 38:
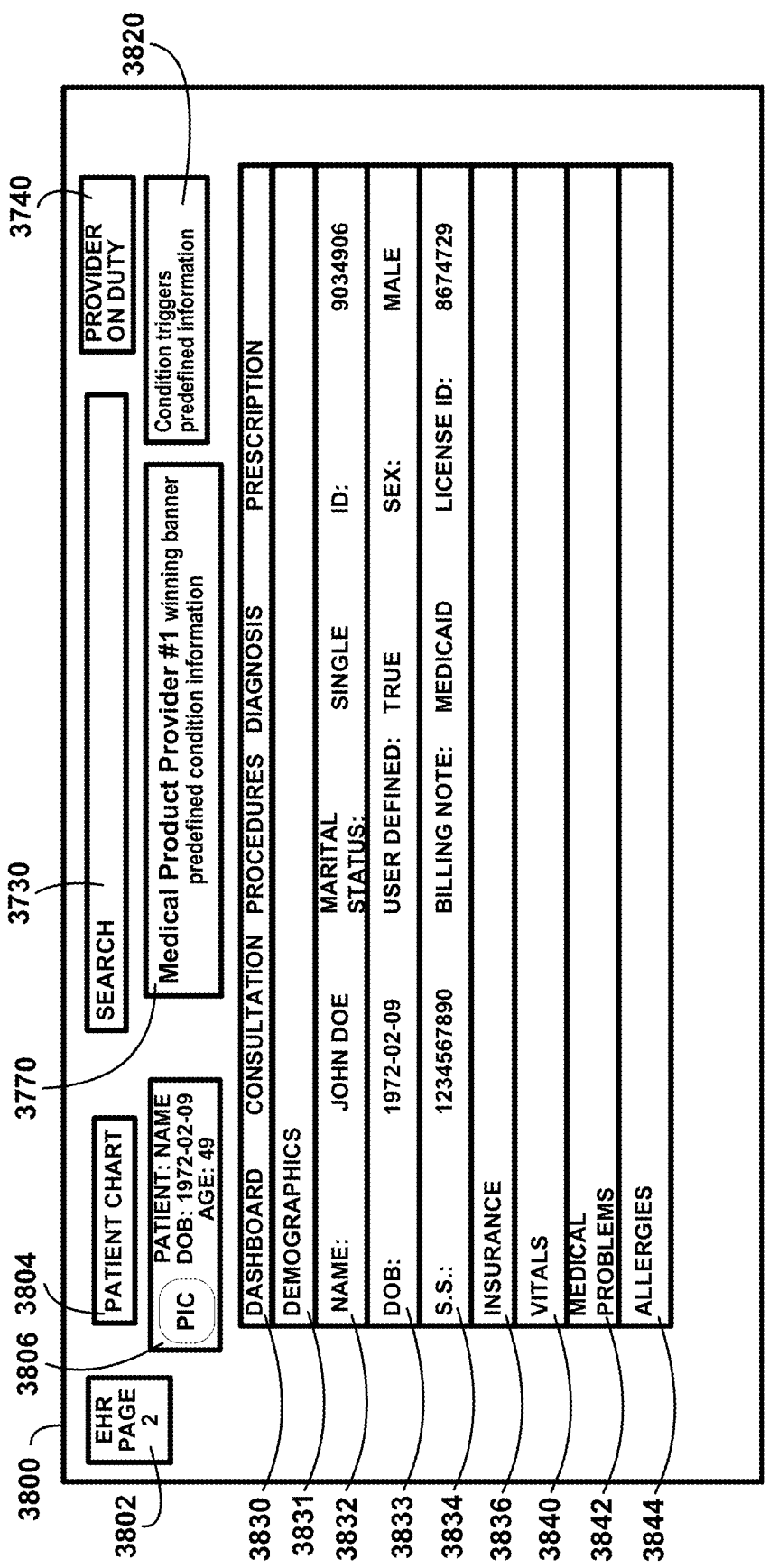
FIG. 38 shows for illustrative purposes only an example of a patient chart of one embodiment.

FIG. 38 shows for illustrative purposes only an example of a patient chart of one embodiment. FIG. 38 shows in one embodiment, for example, a physician-patient continuing workflow webpage 3800 for example EHR page 2 3802. In one embodiment, for example, the physician continues the patient check-up and makes entries on the patient chart 3804. Information associated with Clinical triggers for this specific patient is seen on the patient chart 3804 including the patient's name date of birth 1972-02-09 age 49 and a picture of the patient 3806. The search 3730 tab is used by the EHR system provider 540 Physician on duty to call up messages.

In one embodiment, for example, a Clinical triggers message 3820 lists several Clinical triggers used to select a product advertiser #1 winning banner ad 570. A workflow webpage includes a dashboard, consultation, procedures, and diagnosis; prescription 3830 displays the physician can activate any of the categories. The patient chart 3804 is displaying the patient demographics 3831 including name John Doe, marital status single, id 9034906 3832, DOB 1972-02-09, user-defined true, sex male 3833 and S.S. 1234567890, billing note Medicaid, license id 8674729 3834.

Also available to the physician and critical targeting queries are the patient insurance 3836, vitals 3840, medical problems 3842, and allergies 3844 of one embodiment.

Providing a Physician with Information

Figure 39:
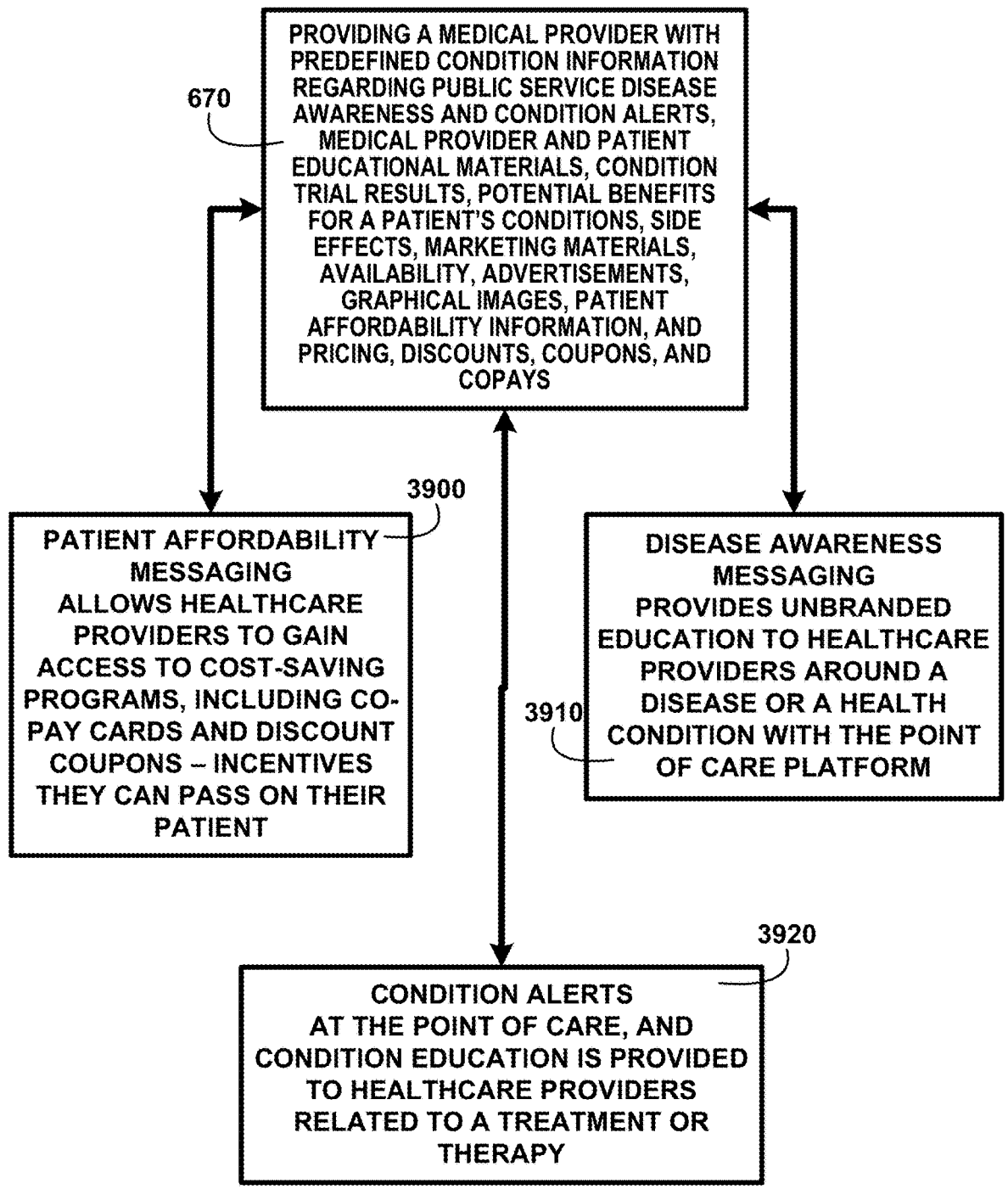
FIG. 39 shows a block diagram of an overview of providing a physician with information of one embodiment.

FIG. 39 shows a block diagram of an overview of providing a physician with information of one embodiment. FIG. 39 shows providing a physician with information regarding patient affordability messaging; disease awareness messaging and clinical alerts 670. Patient affordability messaging allows health care providers to gain access to cost-saving programs, including co-pay cards and discount coupons—incentives they can pass on to their patients 3900. Disease awareness messaging provides unbranded education to healthcare providers around a disease or a health condition with the point of care platform 3910. Clinical alerts at the point of care and clinical education are provided to health care providers related to a treatment or therapy 3920 of one embodiment.

Creation of Ad Copy in Various Formats

Figure 40:
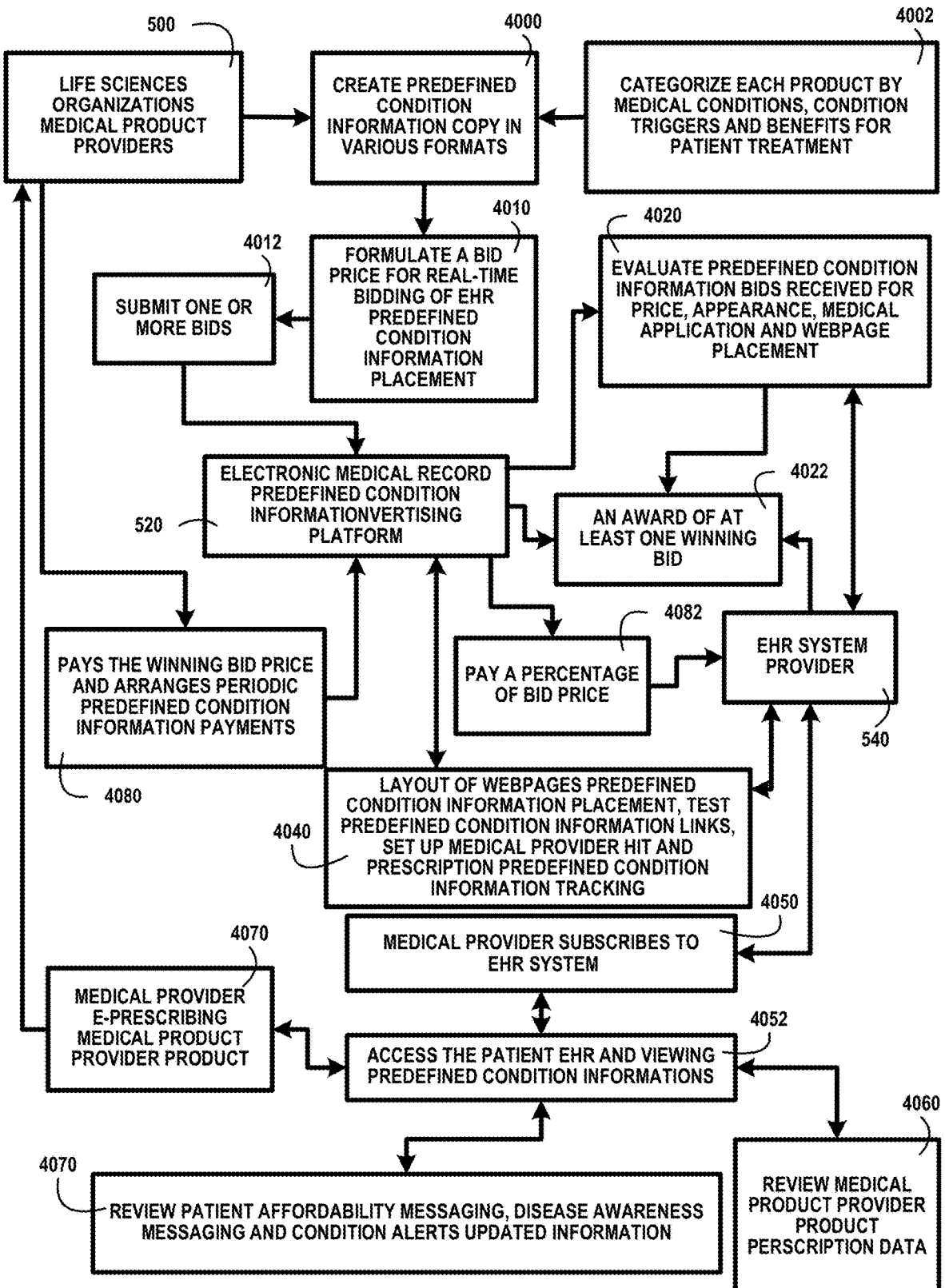
FIG. 40 shows a block diagram of an overview of the creation of ad copy in various formats of one embodiment.

FIG. 40 shows a block diagram of an overview of the creation of ad copy in various formats of one embodiment. FIG. 40 shows the life sciences organization advertisers 500 who create ad copy in various formats 4000. The life sciences organization advertisers 500 categorize each product by medical conditions, Clinical triggers, and benefits for patient treatment 4002. The advertisers formulate a bid price for real-time bidding of EHR ad placement 4010. The life sciences organization advertisers 500 submit one or more bids 4012 to the electronic medical record advertising platform 520.

The electronic medical record advertising platform 520 and EHR system provider 540 evaluate ad bids received for the price, appearance, medical application, and webpage placement 4020. After the evaluations, an award of at least one winning bid 4022 is made. The EHR system provider 540 processes the layout of webpages ad placement, test ad links, set up physician hit and prescription ad tracking 4040. A physician subscribes to EHR system 4050 to access the patient EHR and viewing ads 4052 and review advertiser product prescription data 4060.

The physician may also review patient affordability messaging, disease awareness messaging, and clinical alerts updated information 4070. The information assists the physician in e-prescribing advertiser product 870. The life sciences organization advertisers 500 pays the winning bid price and arranges periodic ad payments 4080 to the electronic medical record advertising platform 520 and the platform automatically process the payment to pay a percentage of bid price 4082 to the EHR system provider 540 of one embodiment.

Providing the Latest Medical Information to Healthcare Providers

Figure 41:
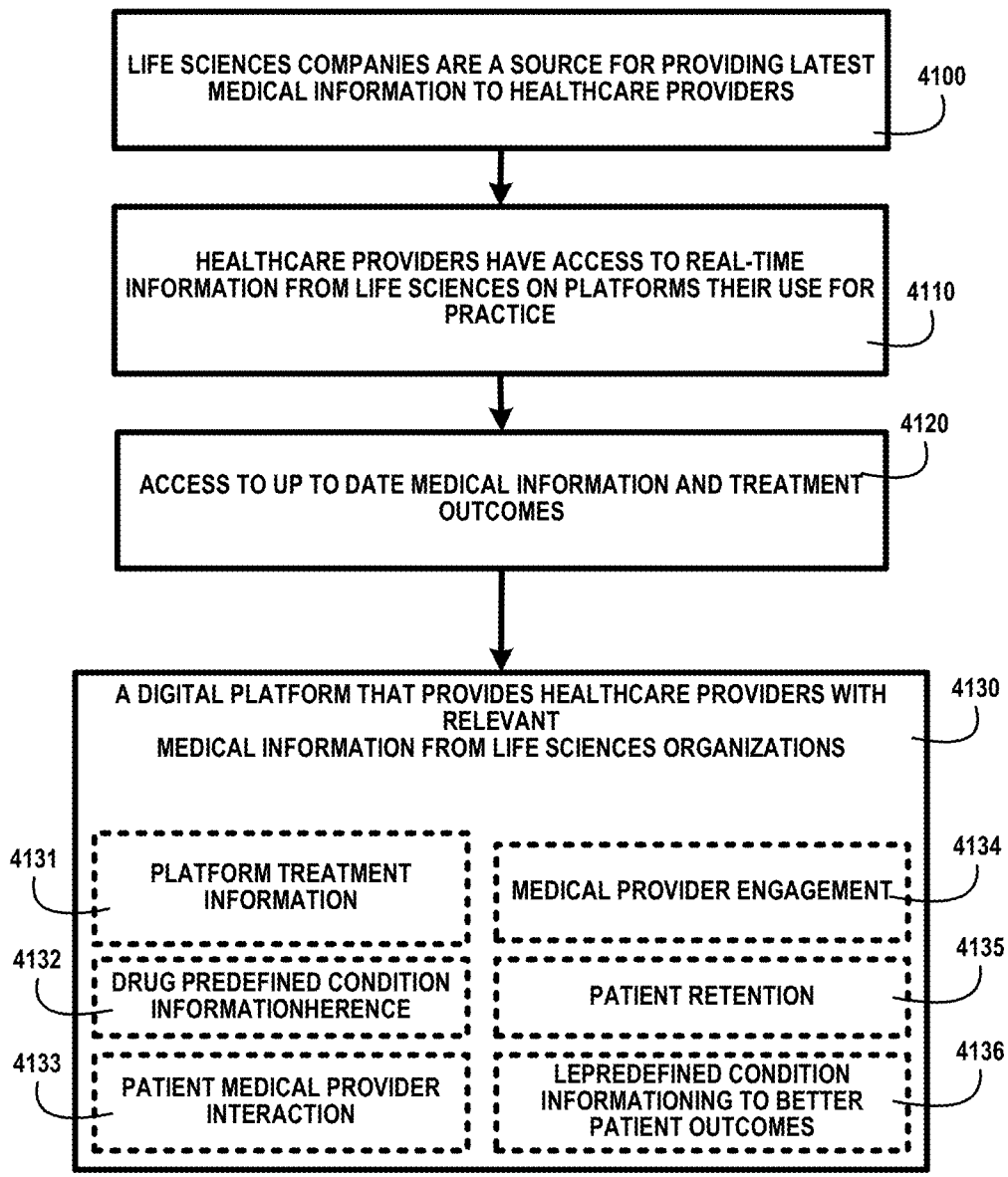
FIG. 41 shows a block diagram of an overview of providing the latest medical information to health care providers of one embodiment.

FIG. 41 shows a block diagram of an overview of providing the latest medical information to health care providers of one embodiment. FIG. 41 shows that life sciences companies are a source for providing the latest medical information to health care providers 4100. The health care providers have access to real-time information from life sciences on platforms they use for their practice 4110. The physician does not have to spend time researching data since the physician has through the EHR system, access to up-to-date medical information and treatment outcomes 4120.

The integrated physician provides a digital platform that provides health care providers with relevant medical information from life sciences organizations 4130. The life sciences information and ad integration are platform treatment information 4131, improve drug adherence 4132, add to patient-physician interaction 4133, and provide physician engagement 4134, and patient retention 4135 all leading to better patient outcomes 4136 of one embodiment.

Patient Affordability Messaging

Figure 42:
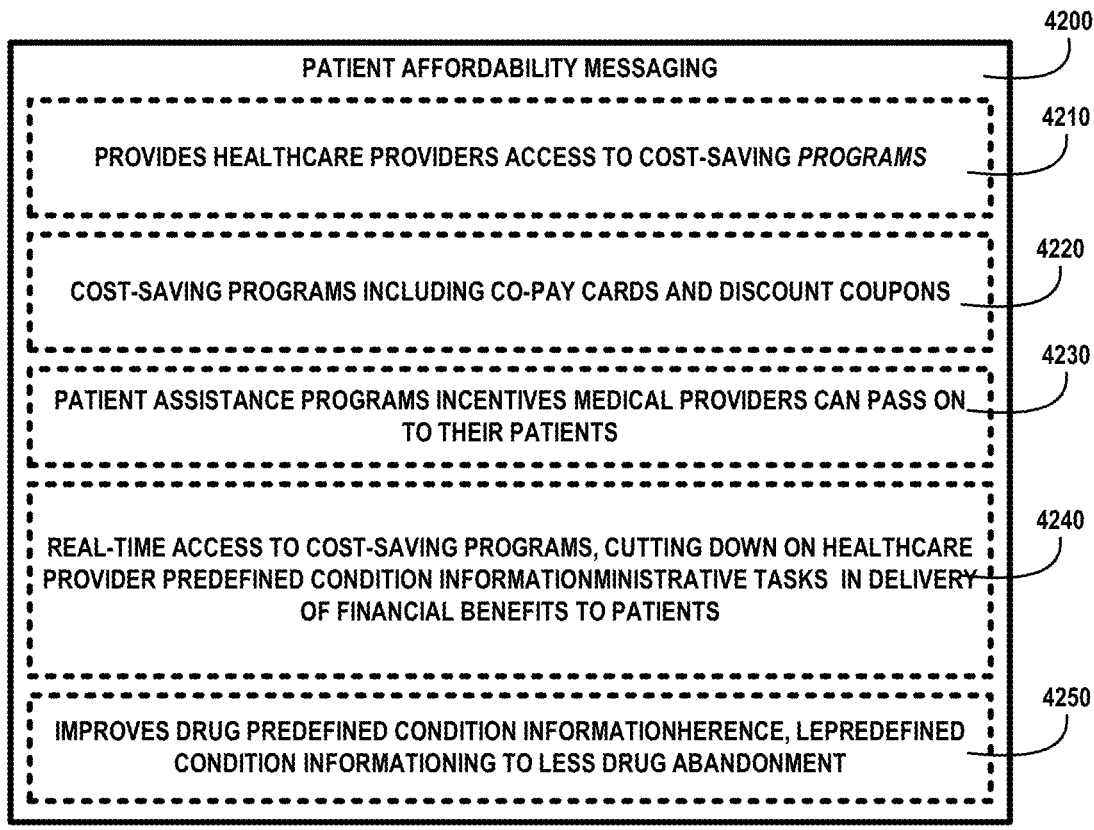
FIG. 42 shows a block diagram of an overview of patient affordability messaging of one embodiment.

FIG. 42 shows a block diagram of an overview of patient affordability messaging of one embodiment. FIG. 42 shows patient affordability messaging 4200 that provides health care providers access to cost-saving programs 4210. The cost-saving programs including co-pay cards and discount coupons 4220 are patient assistance programs incentives they can pass on to their patients 4230. Real-time access to cost-saving programs, cutting down on health care provider administrative tasks in delivery of financial benefits to patients 4240 improves drug adherence, leading to less drug abandonment 4250 of one embodiment.

Clinical Alerts

Figure 43:
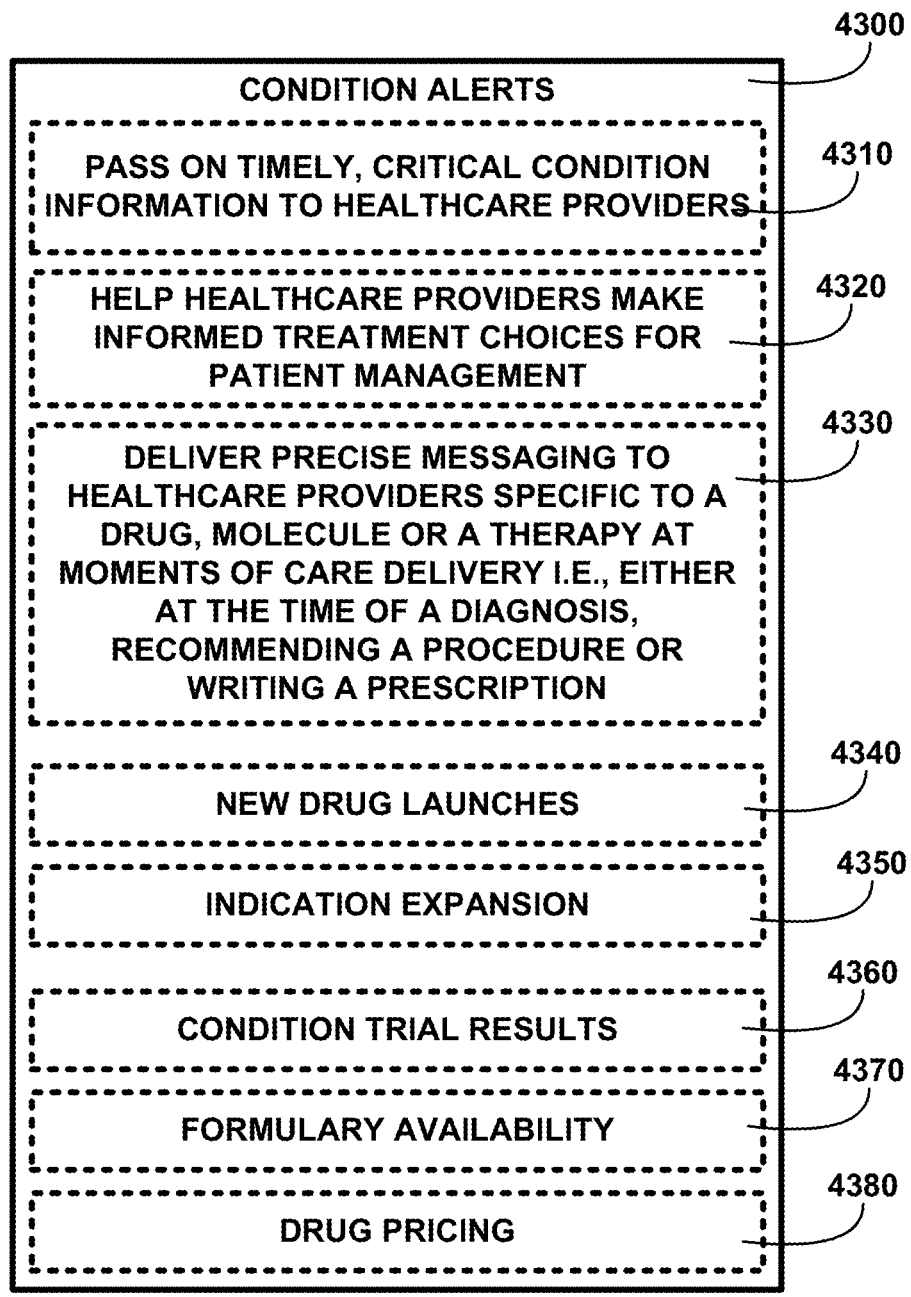
FIG. 43 shows a block diagram of an overview of clinical alerts of one embodiment.

FIG. 43 shows a block diagram of an overview of clinical alerts of one embodiment. FIG. 43 shows clinical alerts 4300 used to pass on timely, critical clinical information to health care providers 4310. The clinical alerts 4300 help healthcare providers make informed treatment choices for patient management 4320 without having to research up-to-date data. The clinical alerts 4300 deliver precise messaging to health care providers specific to a drug, molecule, or therapy at moments of care delivery i.e., either at the time of a diagnosis, recommending a procedure, or writing a prescription 4330. Physicians are kept aware of new drug launches 4340, indication expansion 4350, clinical trial results 4360, formulary availability 4370, and drug pricing 4380 of one embodiment.

Disease Awareness Messaging

Figure 44:
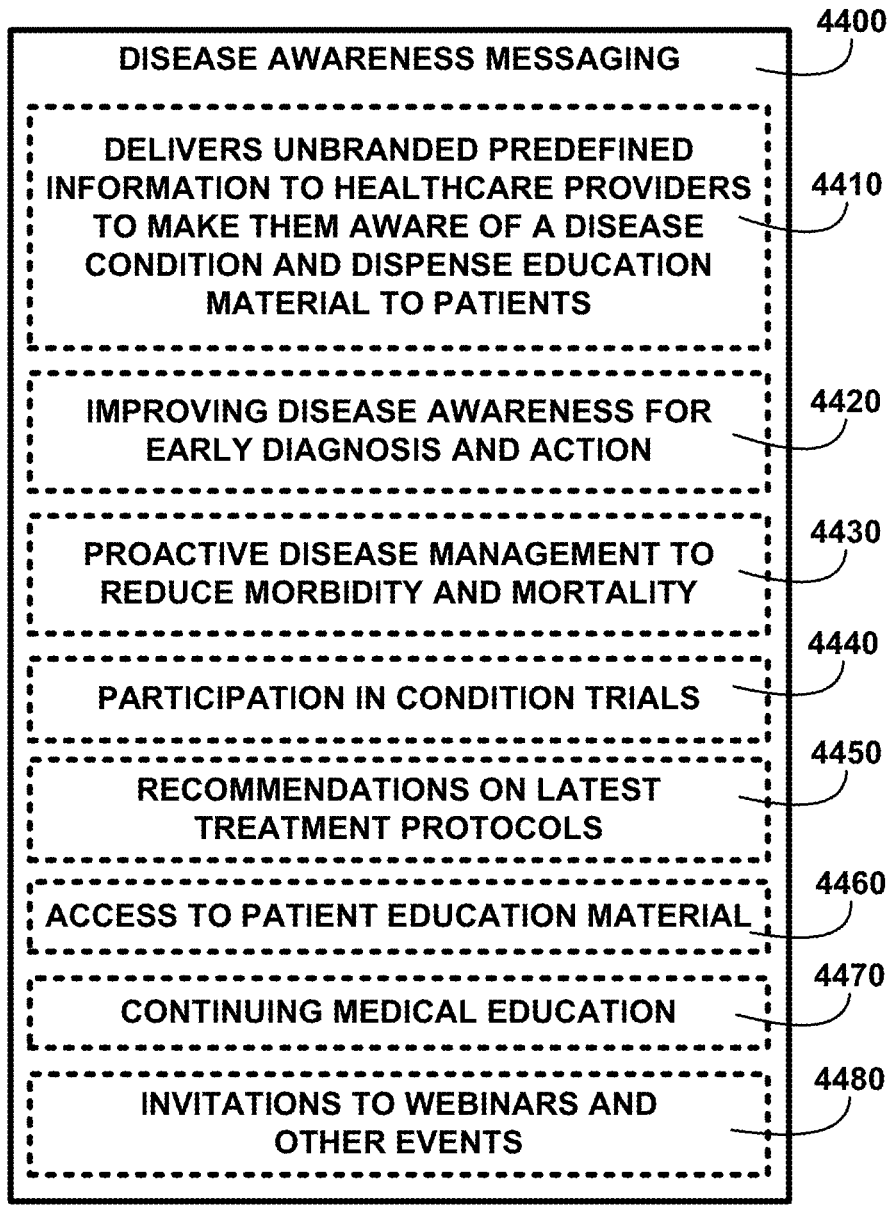
FIG. 44 shows a block diagram of an overview of disease awareness messaging of one embodiment.

FIG. 44 shows a block diagram of an overview of disease awareness messaging of one embodiment. FIG. 44 shows disease awareness messaging 4400 that delivers unbranded messages to health care providers to make them aware of a disease condition and dispense education material to patients 4410. This messaging is improving disease awareness for early diagnosis and action 4420. This messaging is proactive disease management to reduce morbidity and mortality 4430. A physician may determine this patient may be a candidate for participation in clinical trials 4440. It informs the physician of recommendations on the latest treatment protocols 4450. The patient is more engaged with the physician with access to patient education material 4460. The physician is better prepared with readily available continuing medical education 4470 and invitations to webinars and other events 4480 of one embodiment.

Ads and Information Integrated within the Practice Workflow

Figure 45:
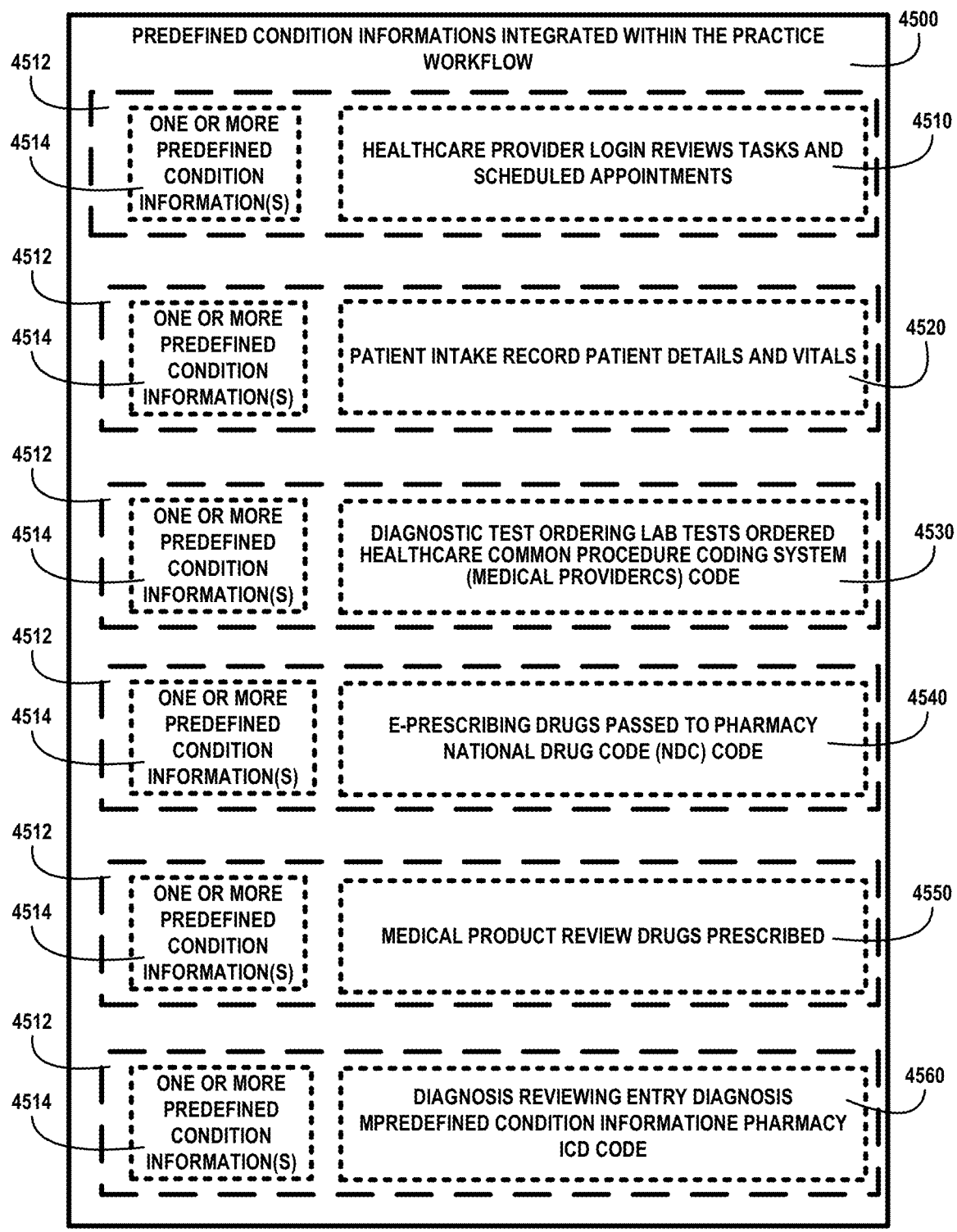
FIG. 45 shows a block diagram of an overview of ads and information integrated within the practice workflow of one embodiment.

FIG. 45 shows a block diagram of an overview of information integrated within the practice workflow of one embodiment. FIG. 45 shows ads integrated within the practice workflow 4500. An initial webpage may include when a health care provider login reviews tasks and schedules appointments 4510 on the practice workflow webpage 4512 with one or more ad(s) 4514 placed in the webpage. Patient intake records patient details and vitals 4520 on the practice workflow webpage 4512 with one or more ad(s) 4514 placed in the webpage.

Diagnostic test ordering lab tests ordered Healthcare Common Procedure Coding System (HCPCS) code 4530 on the practice workflow webpage 4512 with one or more ad(s) 4514 placed in the webpage. E-prescribing drugs passed to pharmacy National Drug Code (NDC) code 4540 on the practice workflow webpage 4512 with one or more ads) 4514 placed in the webpage. Medication review drugs prescribed 4550 on the practice workflow webpage 4512 with one or more ad(s) 4514 placed in the webpage. Diagnosis reviewing entry diagnosis made pharmacy International Classification of Diseases (ICD) code 4560 on the practice workflow webpage 4512 with one or more ad(s) 4514 placed in the webpage of one embodiment.

Selecting Precise Messages Based on the Workflow

Figure 46:
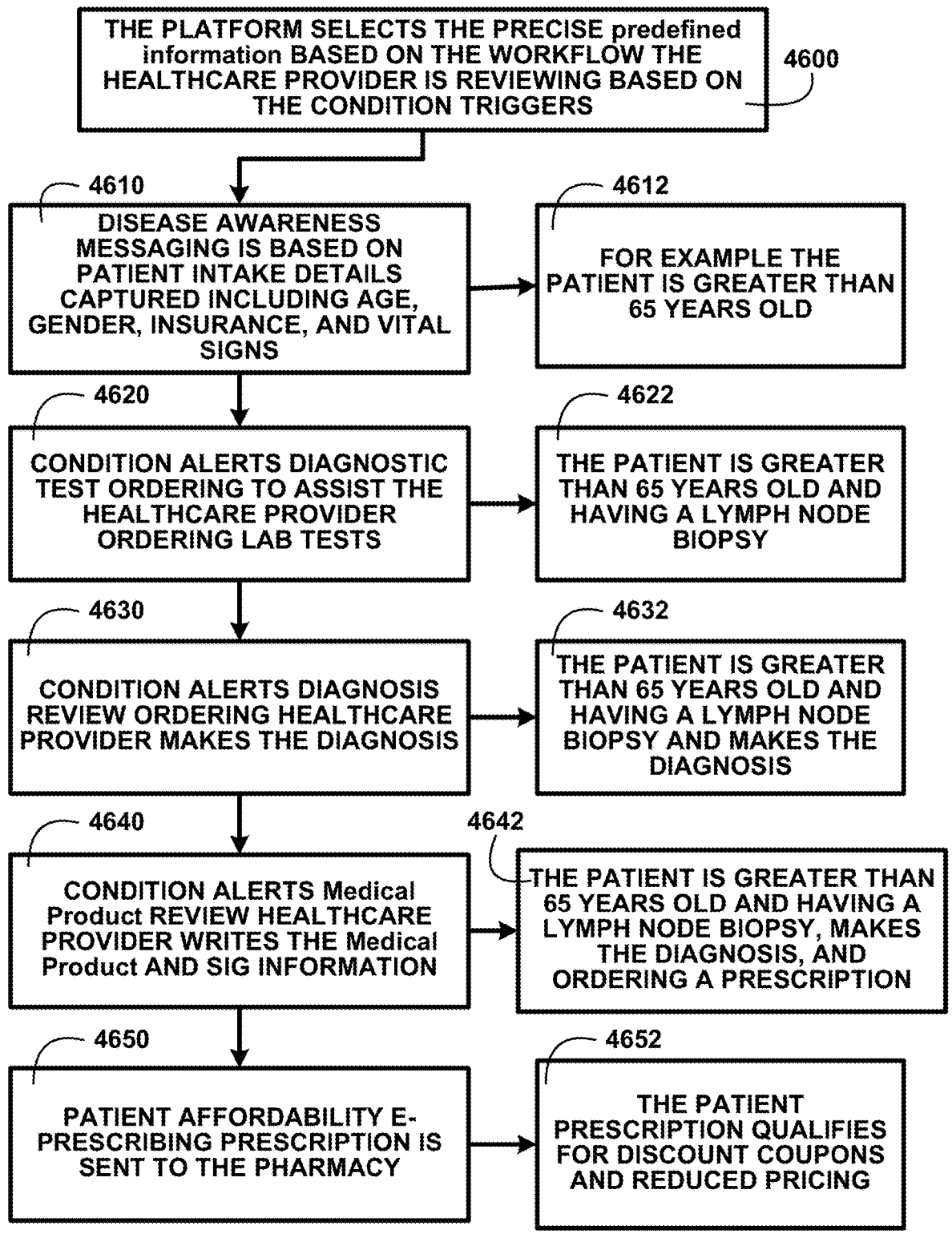
FIG. 46 shows a block diagram of an overview of selecting a precise message based on the workflow of one embodiment.

FIG. 46 shows a block diagram of an overview of selecting a precise message based on the workflow of one embodiment. FIG. 46 shows the platform selects the precise message based on the workflow the health care provider is reviewing based on the Clinical triggers 4600. In one embodiment, for example, disease awareness messaging is based on patient intake details captured including age, gender, insurance, and vital signs 4610 for example, the patient is greater than 65 years old 4612.

One workflow webpage includes clinical alerts diagnostic test ordering to assist the health care provider in ordering lab tests 4620. In one embodiment, for example, this workflow shows the patient is greater than 65 years old and has a lymph node biopsy 4622. Clinical alerts diagnosis review ordering assists the health care provider in making the diagnosis 4630. The patient is greater than 65 years old and has a lymph node biopsy which makes the diagnosis 4632. Clinical alerts medication review assists the health care provider with medication information 4640. An electronic prescription interface integrated into the at least one point-of-care platform configured to provide the health care professional with point-of-care E-prescribing of clinical triggered advertiser's medications. The patient is greater than 65 years old and has a lymph node biopsy, making the diagnosis, and ordering a prescription 4642. In one embodiment, for example, the patient affordability e-prescribing prescription is sent to pharmacy 4650. The patient prescription qualifies for discount coupons and reduced pricing 4652 of one embodiment.

Outcomes

Figure 47:
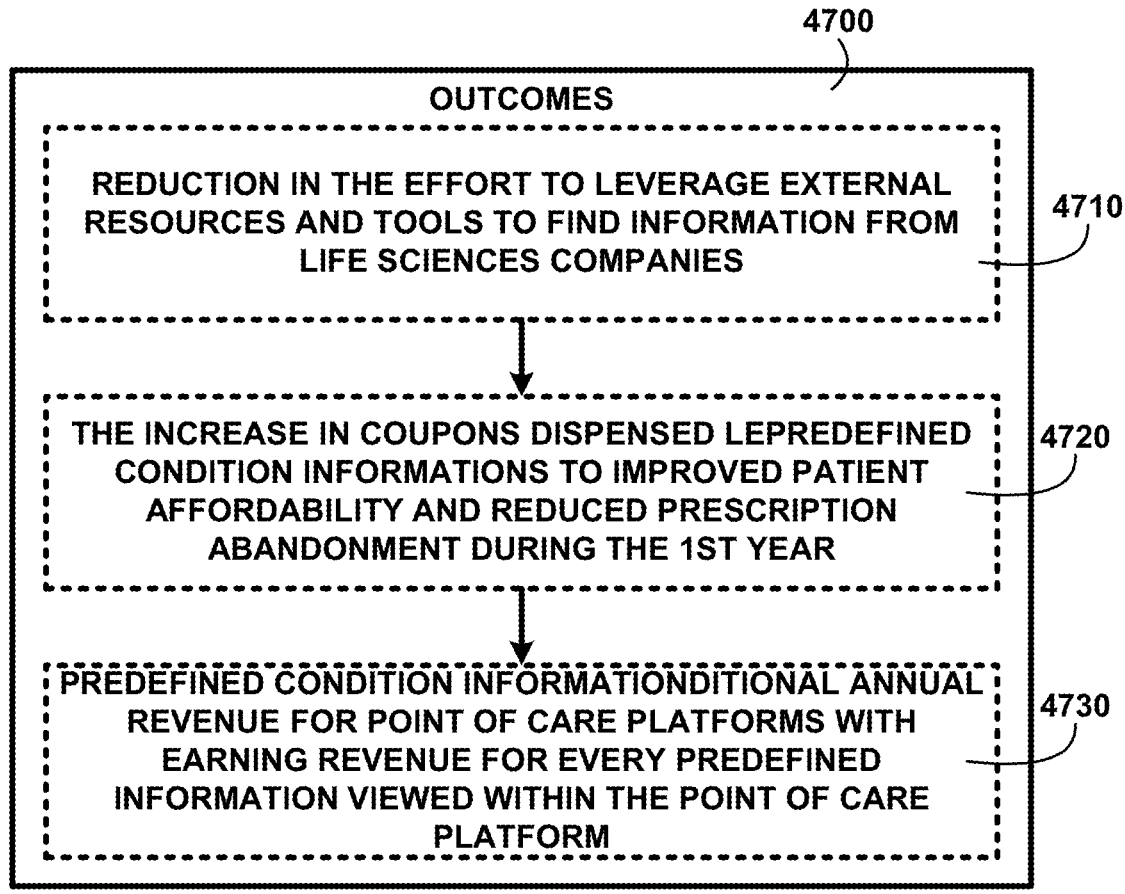
FIG. 47 shows a block diagram of an overview of the outcomes of one embodiment.

FIG. 47 shows a block diagram of an overview of the outcomes of one embodiment. FIG. 47 shows outcomes 4700 benefiting health care providers. In one embodiment, for example, a benefit is a reduction in the effort to leverage external resources and tools to find information from life sciences companies 4710. In another embodiment, for example, the increase in coupons dispensed leads to improved patient affordability and reduced prescription abandonment during the 1st year 4720. In other embodiments, for example, benefits include additional annual revenue for point-of-care platforms with earning revenue for every message viewed within the point-of-care platform 4730 of one embodiment.

HIPAA Compliance

Figure 48:
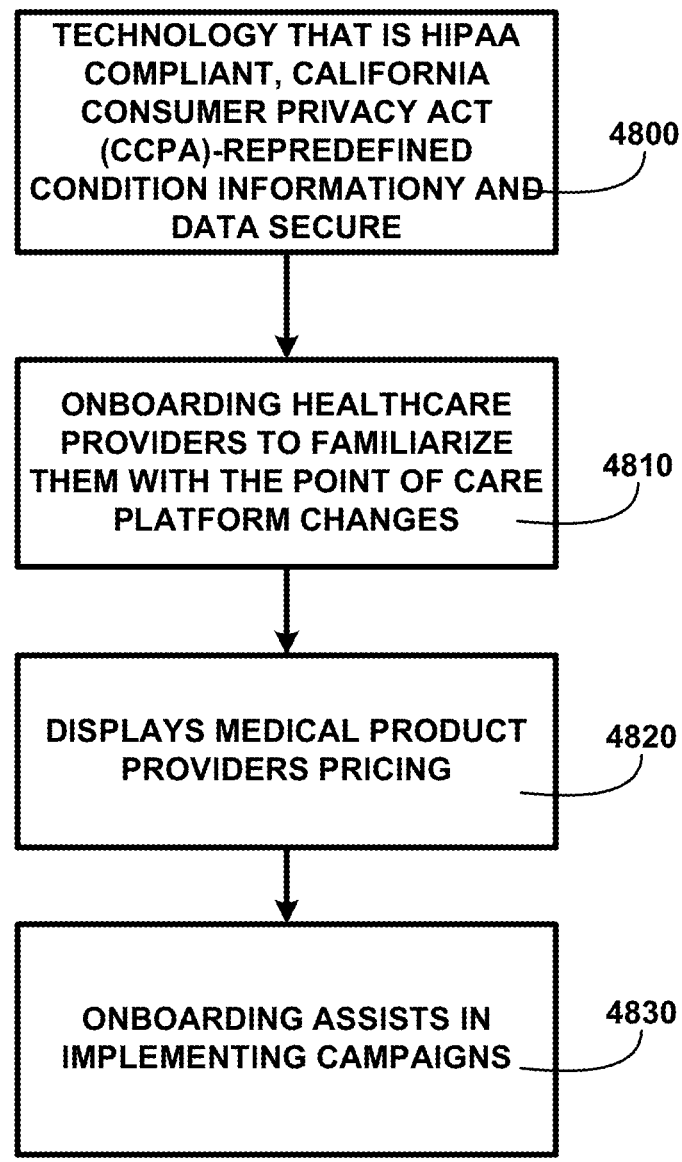
FIG. 48 shows a block diagram of an overview of HIPAA compliance of one embodiment.

FIG. 48 shows a block diagram of an overview of HIPAA compliance of one embodiment. FIG. 48 shows the technology that is HIPAA compliant, California Consumer Privacy Act (CCPA)-READY and data secure 4800. Onboarding health care providers to familiarize them with the point of care platform changes 4810. The electronic medical record advertising platform 520 of FIG. 5 displays advertisers' pricing 4820. Onboarding assists in implementing campaigns 4830 of one embodiment.

Engaging with Healthcare Providers

Figure 49:
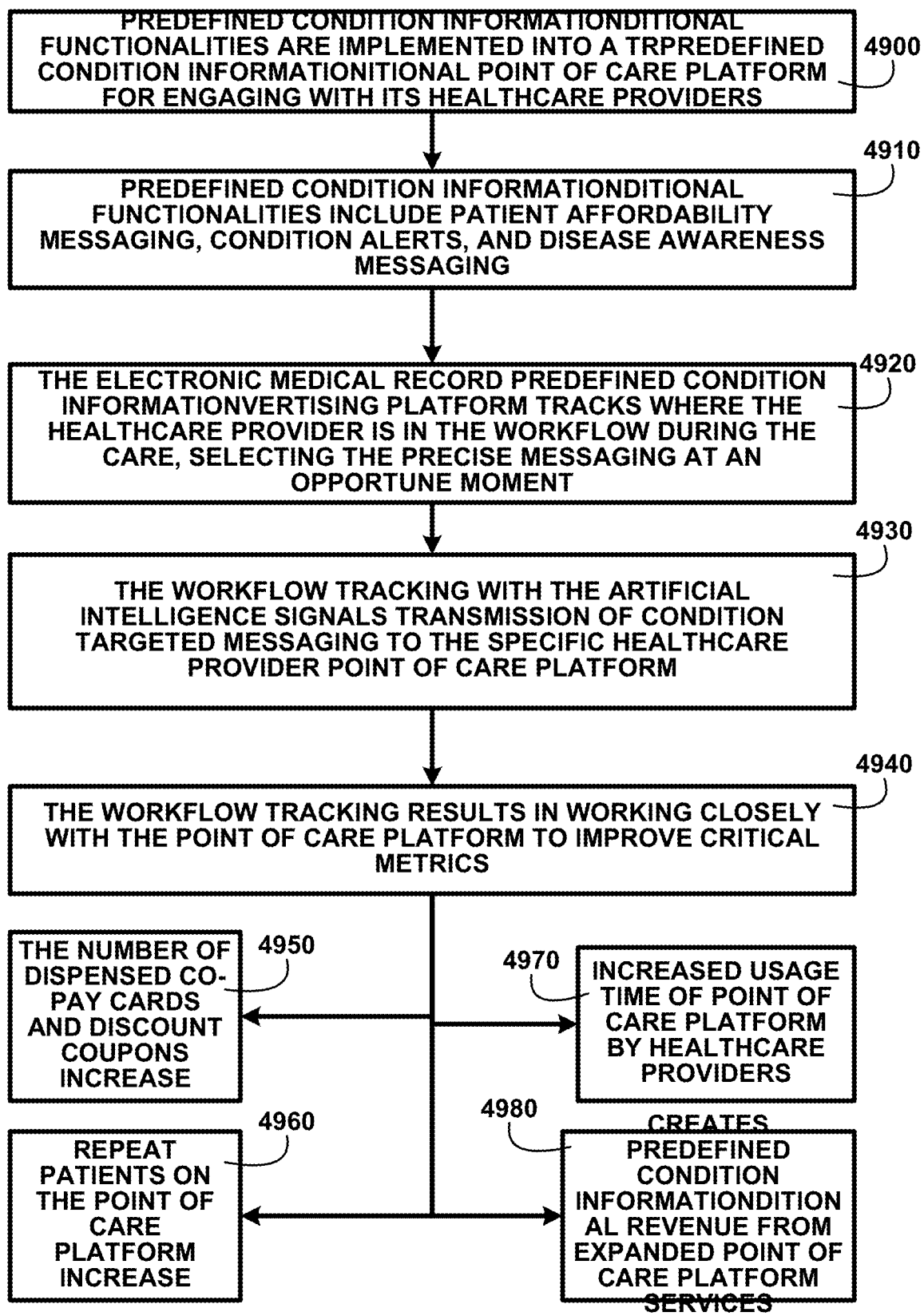
FIG. 49 shows a block diagram of an overview of engaging with health care providers of one embodiment.

FIG. 49 shows a block diagram of an overview of engaging with health care providers of one embodiment. FIG. 49 shows additional functionalities are implemented into a traditional point of care platform for engaging with its health care providers 4900. Additional functionalities include patient affordability messaging, clinical alerts, and disease awareness messaging 4910. The electronic medical record advertising platform tracks where the health care provider is in the workflow during the care, selecting the precise messaging at an opportune moment 4920.

The workflow tracking with the artificial intelligence signals transmission of clinical targeted messaging to the specific health care provider point of care platform 4930. The workflow tracking results are working closely with the point of care platform to improve critical metrics 4940. The number of dispensed co-pay cards and discount coupons increase 4950; repeat patients on the point-of-care platform increased 4960; and increased usage time of point of care platform by healthcare providers 4970 creating additional revenue from an expanded point-of-care platform services 4980 of one embodiment.

Onboarding Process

Figure 50:
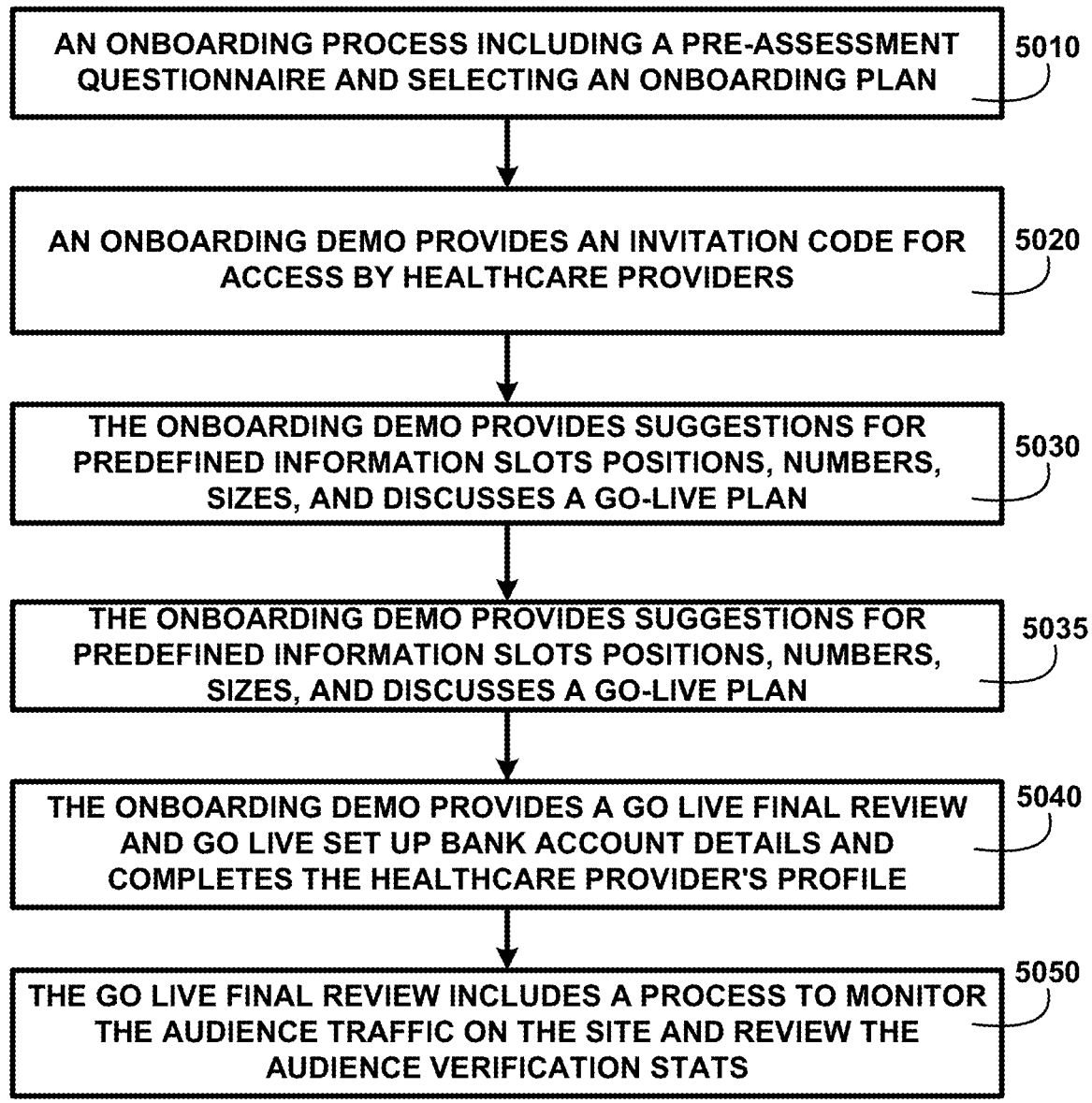
FIG. 50 shows a block diagram of an overview of the onboarding process of one embodiment.

FIG. 50 shows a block diagram of an overview of the onboarding process of one embodiment. FIG. 50 shows an onboarding process including a pre-assessment questionnaire and selecting an onboarding plan 5010. An onboarding demo provides an invitation code for access by healthcare providers 5020. The onboarding demo system test with a review of the platform onboarding 5030. The onboarding demo provides suggestions for message slot positions, numbers, and sizes, and discusses a go-live plan 5035. The onboarding demo provides a go-live final review and goes live set up bank account details and completes the healthcare provider's profile 5040. The go-live final review includes a process to monitor the audience traffic on the site and review the audience verification stats 5050 of one embodiment.

Partnering

Figure 51:
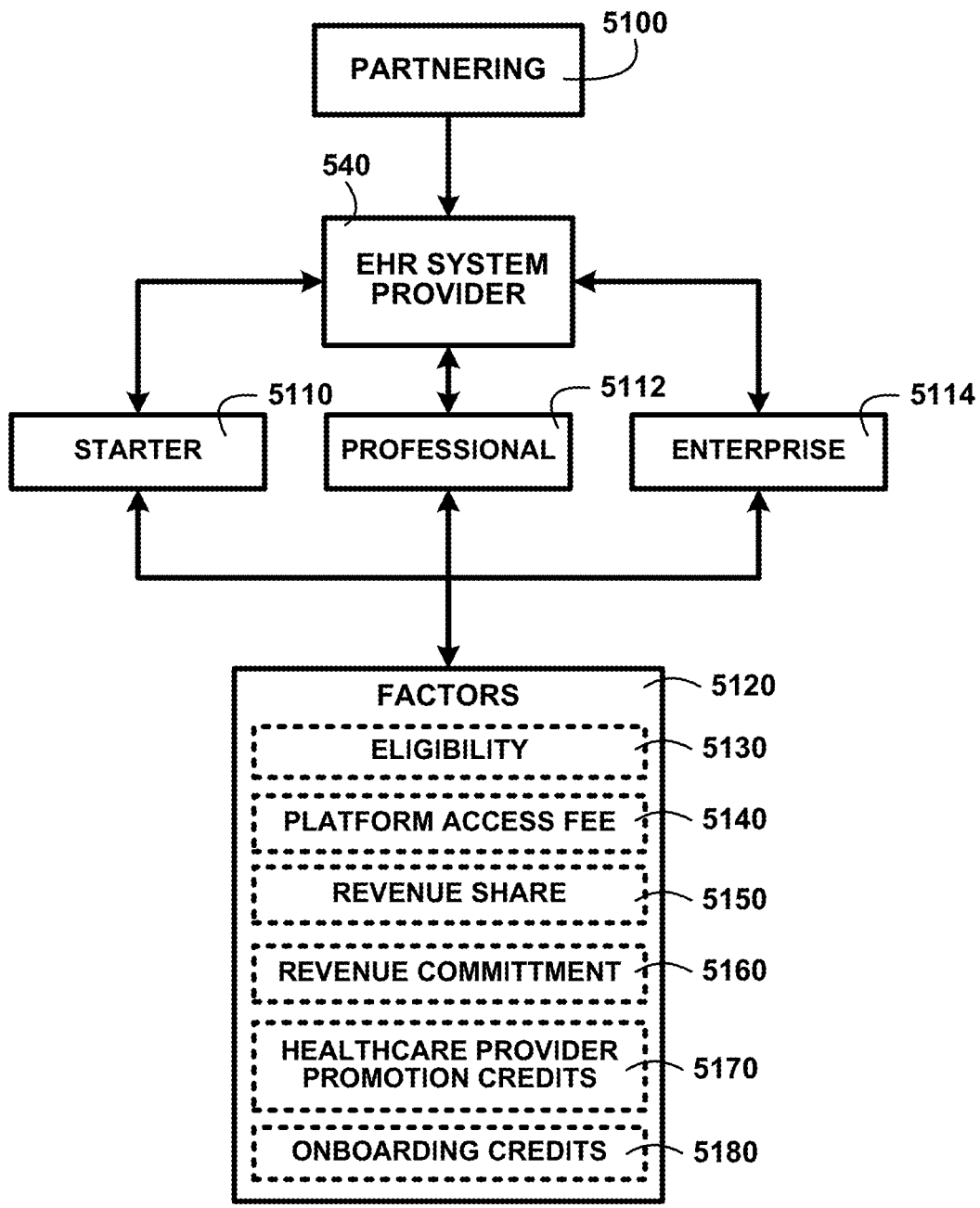
FIG. 51 shows a block diagram of an overview of the partnering of one embodiment.

FIG. 51 shows a block diagram of an overview of the partnering of one embodiment. FIG. 51 shows partnering 5100 between the electronic medical record advertising platform 520 of FIG. 5 and the EHR system provider 540. The EHR system provider 540 partnerships may be classified by the number of subscribers as a starter 5110, professional 5112, and enterprise 5114. Partnering 5100 factors 5120 are differentiated for the classification and partnering structure including eligibility 5130, platform access fee 5140, revenue share 5150, revenue commitment 5160, health care provider promotion credits 5170, and onboarding credits 5180 of one embodiment.

Targeted EHR Webpages to Bid on

Figure 52:
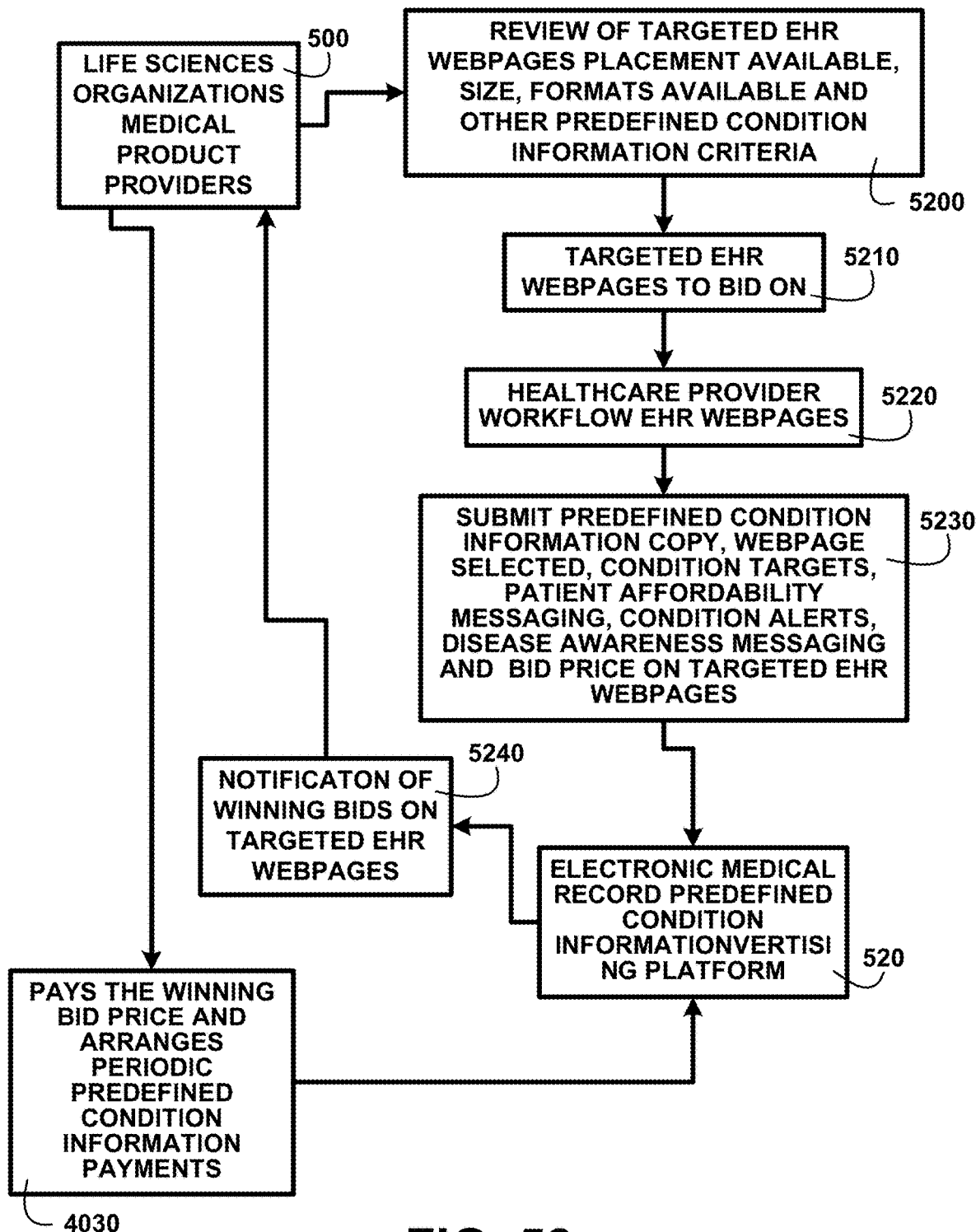
FIG. 52 shows a block diagram of an overview of targeted EHR webpages to bid on of one embodiment.

FIG. 52 shows a block diagram of an overview of targeted EHR webpages to bid on of one embodiment. FIG. 52 shows the life sciences organization advertisers 500 reviews of targeted EHR webpages placement available, size, formats available, and other ad criteria 5200 to decide which targeted EHR webpages to bid on 5210. Once the life sciences organization advertisers 500 selects one or more health care provider workflow EHR webpages 5220 they will submit ad copy, webpages selected, clinical targets, patient affordability messaging, clinical alerts, disease awareness messaging, and bid price on targeted EHR webpages 5230. The electronic medical record advertising platform 520 communicates a notification of winning bids on targeted EHR web pages 5240 to the life sciences organization advertisers 500. The winning life sciences organization advertiser 500 pays the winning bid price and arranges periodic ad payments 4030 of one embodiment.

Establishing Health Care Provider Workflow Web Pages

Figure 53:
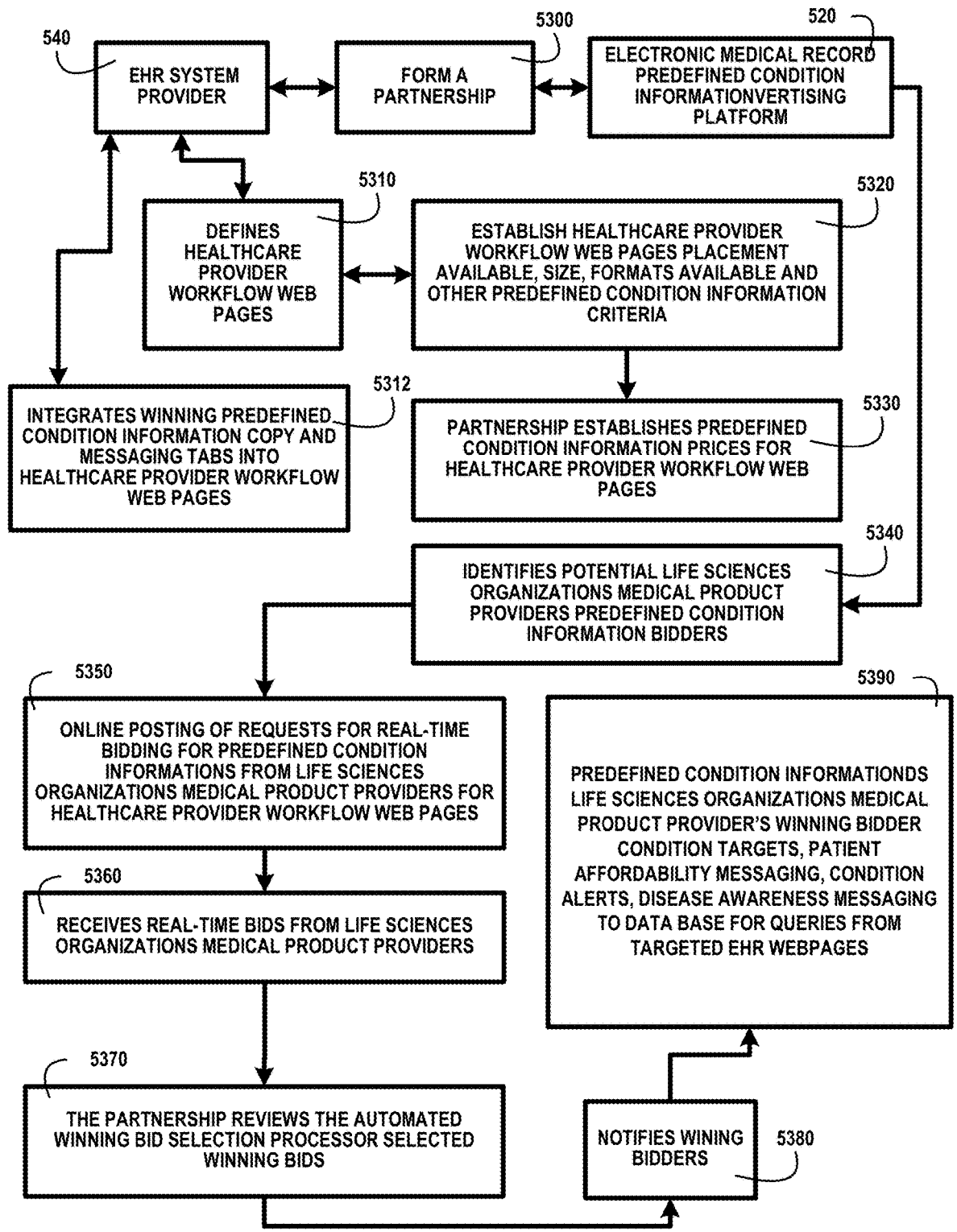
FIG. 53 shows a block diagram of an overview of establishing health care provider workflow web pages of one embodiment.

FIG. 53 shows a block diagram of an overview of establishing health care provider workflow web pages of one embodiment. FIG. 53 shows the EHR system provider 540 agrees to form a partnership 5300 with the electronic medical record advertising platform 520. The EHR system provider 540 defines health care provider workflow web pages 5310 and integrates winning ad copy and messaging tabs into health care provider workflow web pages 5312.

The EHR system provider 540 will establish health care provider workflow web pages placement available, size, formats available, and other ad criteria 5320. The partnership establishes ad prices for health care provider workflow web pages 5330. The electronic medical record advertising platform 520 identifies potential life sciences organizations advertiser ad bidders 5340 with products targeting patient conditions. The electronic medical record advertising platform 520 proceeds with online posting of requests for real-time bidding for ads from life sciences organizations advertisers for health care provider workflow web pages 5350.

The electronic medical record advertising platform 520 receives real-time bids from life sciences organizations advertisers 5360. The partnership reviews the automated winning bid selection processor and selected winning bids 5370. The electronic medical record advertising platform 520 notifies the winning bidders 5380. The partnership adds life sciences organizations advertisers winning bidder clinical targets, patient affordability messaging, clinical alerts, and disease awareness messaging to a database for queries from targeted EHR webpages 5390 of one embodiment.

Physician e-Prescribing Medication from Product Advertiser

Figure 54:
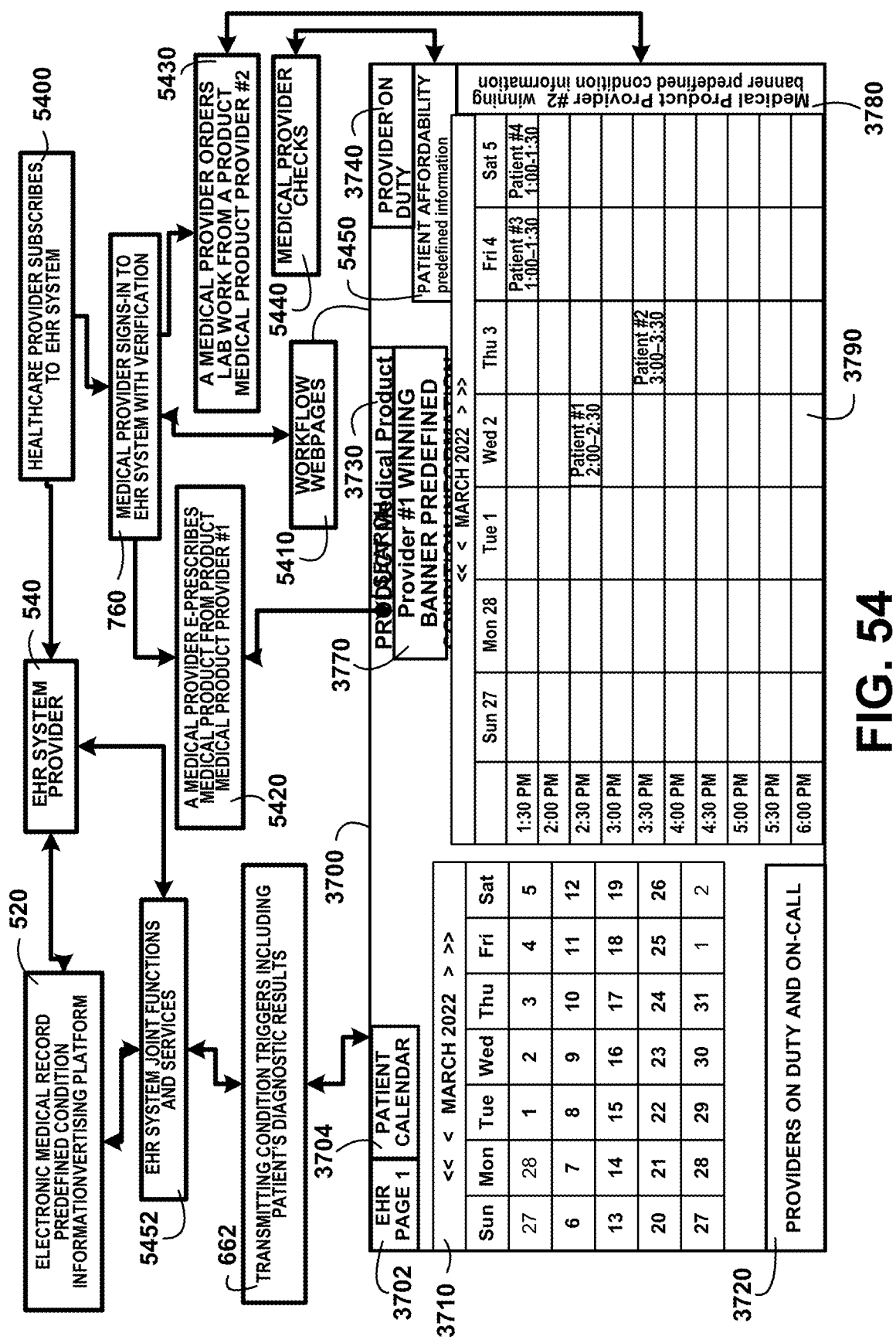
FIG. 54 shows a block diagram of an overview of physicians e-prescribing medication from product advertisers of one embodiment.

FIG. 54 shows a block diagram of an overview of physicians e-prescribing medication from product advertisers of one embodiment. FIG. 54 shows the electronic medical record advertising platform 520 and EHR system provider 540 integrated platforms provide an expanded capability for a point of care platform. A healthcare provider subscribes to EHR system 5400. The physician signs in to the EHR system physician sign-in verification device 760 with verification and begins accessing workflow webpages 5410. In one embodiment, for example, a physician e-prescribes medication from product advertiser #1 5420.

A physician orders lab work from a product advertiser #2 5430. The physician checks 5440 a patient affordability message 5450 to receive updated information on the patient's cost-saving programs. In one embodiment, for example, the physician-patient workflow webpage 3700 EHR page 1 3702 displays the patient calendar 3704, current month calendar 3710, care providers 3720, and search 3730 tabs. The provider Physician on duty 3740 can see and tap the product advertiser #1 winning banner ad 3770 and product advertiser #2 winning banner ad 3780 to learn more about those products. The provider-patient appointment calendar 3790 data is transmitting Clinical triggers including patient's diagnostic results 662 in one aspect of the EHR system joint functions and services 5452 of one embodiment.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. A medical product processing system, comprising:
   a local computer having a first graphical user interface coupled to an electronic health record platform that generates a display to a medical provider of predefined medical conditions, demographic information, gender information and International Classification of Diseases (ICD) diagnosis codes of a patient of the medical provider;
   a remote computer server coupled to the first computer and having a database for storing plural records stored therein containing predefined information relating to plural medical products related to the demographic information, gender information, ICD diagnosis codes and the predefined medical conditions;
   an advertising computer coupled to the database of the remote computer server and having a second graphical user interface that generates a display to a medical product provider of adjustable condition trigger settings, wherein the adjustable condition trigger settings are configurable by the medical product provider to associate at least one targeted advertisement with at least one of the predefined medical conditions, demographic information, gender information or ICD diagnosis codes;
   a processor of the remote computer server coupled to the database, the first graphical user interface and the second graphical user interface to activate the adjustable condition trigger settings to automatically control a selectable display of the at least one targeted advertisement to the medical provider's digital electronic device on the first graphical user interface; and
   wherein when the first graphical user interface displays the at least one targeted advertisement based on the adjustable condition trigger settings to the first graphical interface, wherein the processor automatically sends a notification to the advertising computer indication whether or not the at least one targeted advertisement has been displayed on the first graphical user interface.

2. The medical product processing system of claim 1, wherein if the medical provider selects at least one targeted advertisement, preselected product information is automatically and electronically delivered to a portable electronic device of the patient.

3. The medical product processing system of claim 1, further comprising wherein the local computer further includes a comment interface configured to allow the medical provider to send feedback about the at least one targeted advertisement to the medical product provider's digital electronic device.

4. The medical product processing system of claim 1, further comprising wherein the processor of the remote computer server analyzes the notifications to determine a return on investment of the at least one targeted advertisement.

5. The medical product processing system of claim 1, wherein the local computer further includes an e-prescribing interface to allow the medical provider to select the at least one targeted advertisement and e-prescribe a medical product automatically associated with the at least one targeted advertisement for the patient.

6. The medical product processing system of claim 1, business wherein if the medical provider selects the displayed at least one targeted advertisement, discount coupons are delivered electronically for medical products associated with the at least one targeted advertisement to a portable digital electronic device of the patient.

7. The medical product processing system of claim 1, further comprising a portable mobile device controlled by the patient that generates a display of the medical product information if the medical provider selects the displayed at least one targeted advertisement during real-time interaction between the patient and the medical provider.

8. A medical product processing system, comprising:
a local computer having a first graphical user interface coupled to an electronic health record platform and configured to display to a medical provider predefined medical conditions, demographic information, gender information and International Classification of Diseases (ICD) diagnosis codes of a patient of the medical provider;
a remote computer server coupled to the first computer and having a database with plural records stored therein containing predefined information relating to plural medical products related to the demographic information, gender information, ICD diagnosis codes and the predefined conditions;
an advertising computer coupled to the database of the remote computer server and having a second graphical user interface configured to display to a medical product provider adjustable condition trigger settings, wherein the adjustable condition trigger settings are configurable by the medical product provider to associate at least one targeted advertisement with at least one of the predefined medical conditions, demographic information, gender information or ICD diagnosis codes;
a processor of the remote computer server coupled to the database, the first graphical user interface and the second graphical user interface configured to use the adjustable condition trigger settings to automatically control a selectable display of the at least one targeted advertisement to the medical provider on the first graphical user interface;
wherein when the first graphical user interface displays the at least one targeted advertisement based on the adjustable condition trigger settings to the medical provider, the processor automatically sends a notification to the advertising computer that the at least one targeted advertisement has been displayed on the first graphical user interface based on the adjustable condition trigger setting configured by the medical product provider and has been either selected or not selected by the medical provider; and
wherein the remote computer gathers data on the either selected or not selected advertisements and sends the data to the medical product provider for analysis.

9. The medical product processing system of claim 8, wherein if the medical provider selects at least one displayed targeted advertisement, product information is automatically and electronically delivered to a portable electronic device of the patient.

10. The medical product processing system of claim 8, wherein the local computer further includes a comment interface configured to allow the medical provider to send feedback about the at least one targeted advertisement to the medical product provider's digital electronic device.

11. The medical product processing system of claim 8, wherein the remote computer server analyzes the notifications to determine a return on investment of the at least one targeted advertisement.

12. The medical product processing system of claim 8, further comprising a portable mobile device controlled by the patient to generate a display of the medical product information if the medical provider selects the displayed at least one targeted advertisement during real-time interaction with the patient and the medical provider.

13. The medical product processing system of claim 8, wherein when the medical provider selects the displayed at least one targeted advertisement, discount coupons are electronically delivered for medical products associated with the at least one targeted advertisement to a portable digital electronic device of the patient.

14. The medical product processing system of claim 8, further comprising a portable mobile device controlled by the patient that generates a display of medical product information if the medical provider selects the displayed at least one targeted advertisement during real-time interaction with the patient and the medical provider.

15. A medical product system, comprising:
a first computer having a first memory to store a plurality of patients of a medical provider in an electronic health record platform and a first processor to generate a first graphical user interface coupled to the electronic health record platform to display medical conditions, demographic information, gender information and International Classification of Diseases (ICD) diagnosis codes of each patient to the medical provider;
a remote computer server coupled to the first computer having a remote memory with plural records stored therein containing predefined information relating to plural medical advertisements and having a remote processor to generate a plurality of clinical triggers for the medical advertisements related to the medical conditions, demographic information, gender information and ICD diagnosis codes and a second memory to store the plurality of clinical triggers;
a second computer coupled to the remote computer server having a second processor to generate a second graphical user interface to display to a medical product provider selectable clinical triggers for the medical advertisements associated with at least one predefined medical condition, demographic information, gender information or at least one ICD diagnosis code;
wherein the second processor further compares the clinical triggers to the medical advertisements to suggest at least one selectable medical advertisement for the medical product provider, allows the medical product provider to select at least one medical advertisement and sends the selected medical advertisement to the first computer via the remote computer server;
wherein the first processor further receives the selected medical advertisement and generates the selected medical advertisements to be displayed on the first graphical user interface for either being selected or not selected by the medical provider;
wherein the remote processor compares when the selectable medical advertisement is either selected or not selected by the medical provider; and
wherein the remote processor automatically generates a notification to the second computer indicating analytical results of the comparison of when the selectable medical advertisement is either selected or not selected by the medical provider to recommend adjustments by the medical product provider of the one selectable medical advertisement.

16. The medical product system of claim 15, wherein when the medical provider selects at least one medical advertisement, predetermined product information is automatically and electronically delivered to a portable electronic device of the patient.

17. The medical product system of claim 15, wherein the first computer further includes a comment interface to allow the medical provider to send feedback about the at least one medical advertisement to the medical product provider's digital electronic device.

18. The medical product system of claim 15, wherein the remote processor analyzes the notifications to determine a return on investment of the at least one medical advertisement.

19. The medical product system of claim 15, wherein the first computer further includes an e-prescribing interface to allow the medical provider to select the at least one medical advertisement and automatically e-prescribe a medical product associated with the at least one medical advertisement for the patient.

20. The medical product system of claim 15, wherein when the medical provider selects the displayed at least one medical advertisement, discounts are received electronically for medical products associated with the at least one medical advertisement and are automatically and electronically delivered to a portable digital electronic device of the patient.

\* \* \* \* \*